(12) United States Patent
Tanis et al.

(10) Patent No.: US 9,562,012 B2
(45) Date of Patent: Feb. 7, 2017

(54) PPAR-SPARING COMPOUNDS FOR THE TREATMENT OF METABOLIC DISEASES

(71) Applicant: Metabolic Solutions Development Company, LLC, Kalamazoo, MI (US)

(72) Inventors: Steven P. Tanis, Carlsbad, CA (US); Scott D. Larsen, South Lyon, MI (US); Gerald D. Artman, III, Schoolcraft, MI (US); Timothy Parker, Portage, MI (US)

(73) Assignee: Metabolic Solutions Development Company, LLC, Kalamazoo, MI (US)

( * ) Notice: Subject to any disclaimer, the term of this patent is extended or adjusted under 35 U.S.C. 154(b) by 0 days.

(21) Appl. No.: 14/906,686

(22) PCT Filed: Jul. 21, 2014

(86) PCT No.: PCT/US2014/047411
§ 371 (c)(1),
(2) Date: Jan. 21, 2016

(87) PCT Pub. No.: WO2015/013187
PCT Pub. Date: Jan. 29, 2015

(65) Prior Publication Data
US 2016/0152570 A1    Jun. 2, 2016

Related U.S. Application Data

(60) Provisional application No. 61/856,850, filed on Jul. 22, 2013.

(51) Int. Cl.

| | | |
|---|---|---|
| A61K 31/085 | (2006.01) |
| A61K 31/165 | (2006.01) |
| A61K 31/33 | (2006.01) |
| C07D 213/68 | (2006.01) |
| C07C 259/06 | (2006.01) |
| C07C 309/66 | (2006.01) |
| C07C 317/22 | (2006.01) |
| C07D 213/30 | (2006.01) |
| A61K 31/44 | (2006.01) |
| A61K 31/4402 | (2006.01) |
| A61K 45/06 | (2006.01) |

(52) U.S. Cl.
CPC ............ *C07D 213/68* (2013.01); *A61K 31/085* (2013.01); *A61K 31/165* (2013.01); *A61K 31/33* (2013.01); *A61K 31/44* (2013.01); *A61K 31/4402* (2013.01); *A61K 45/06* (2013.01); *C07C 259/06* (2013.01); *C07C 309/66* (2013.01); *C07C 317/22* (2013.01); *C07D 213/30* (2013.01)

(58) Field of Classification Search
CPC .... A61K 31/085; A61K 31/165; A61K 31/33; C07D 213/68
See application file for complete search history.

(56) References Cited

U.S. PATENT DOCUMENTS

| | | |
|---|---|---|
| 8,067,450 B2 | 11/2011 | Colca et al. |
| 8,304,441 B2 | 11/2012 | Colca et al. |
| 8,389,556 B2 | 3/2013 | Colca et al. |
| 8,629,159 B2 | 1/2014 | Colca et al. |
| 8,912,335 B2 | 12/2014 | Colca et al. |
| 9,126,959 B2 | 9/2015 | Colca et al. |
| 9,155,729 B2 | 10/2015 | Colca et al. |

FOREIGN PATENT DOCUMENTS

| | | |
|---|---|---|
| EP | 0907743 | 3/1999 |
| WO | WO9962871 | 12/1999 |
| WO | WO2011075514 | 6/2011 |
| WO | WO2012177956 | 12/2012 |

OTHER PUBLICATIONS

International Search Report for PCT/US2014/047411 dated Oct. 15, 2014.

*Primary Examiner* — Yong Chong
(74) *Attorney, Agent, or Firm* — Honigman Miller Schwartz & Cohn LLP; Andrew N. Weber; Jonathan P. O'Brien

(57) ABSTRACT

The present invention relates to hydroxamate compounds and pharmaceutical compositions that are useful for treating and/or preventing metabolic inflammation mediated diseases such as diabetes, obesity, hypertension, dyslipidemia, a neurodegenerative disorder (e.g., Alzheimer's disease, Parkinson's disease, or Huntington's disease), or any combination thereof. Moreover, the present invention also provides methods of treatment for these diseases or disorders.

23 Claims, No Drawings

PPAR-SPARING COMPOUNDS FOR THE TREATMENT OF METABOLIC DISEASES

CROSS REFERENCE TO RELATED APPLICATIONS

This application is a national phase application of PCT Application No. PCT/US2014/047411, filed on Jul. 21, 2014, which claims the benefit of U.S. Provisional Application Ser. No. 61/856,850, filed on Jul. 22, 2013. The entire contents of the aforementioned applications are incorporated herein by reference.

TECHNICAL FIELD OF THE INVENTION

The present invention provides hydroxamate compounds of Formula I and pharmaceutical compositions containing these compounds for use in treating, reducing the severity of, and/or preventing metabolic mediated disorders (e.g., diabetes, obesity, dyslipidemia, and the like).

BACKGROUND OF THE INVENTION

Over the past several decades, scientists have postulated that PPARγ is the generally accepted site of action for insulin sensitizing compounds.

Peroxisome Proliferator Activated Receptors (PPARs) are members of the nuclear hormone receptor super family that are ligand-activated transcription factors regulating gene expression. PPARs have been implicated in autoimmune diseases and other diseases, i.e. diabetes mellitus, cardiovascular and gastrointestinal disease, and Alzheimer's disease.

PPARγ is a key regulator of adipocyte differentiation and lipid metabolism. PPARγ is also found in other cell types including fibroblasts, myocytes, breast cells, human bone-marrow precursors, and macrophages/monocytes. In addition, PPARγ has been found in macrophage foam cells in atherosclerotic plaques.

Thiazolidinedione compounds, developed originally for the treatment of type-2 diabetes, generally exhibit high-affinity as PPARγ ligands. The finding that thiazolidinediones might mediate their therapeutic effects through direct interactions with PPARγ helped to establish the concept that PPARγ is a key regulator of glucose and lipid homeostasis. However, compounds that involve the activation of PPARγ also trigger sodium reabsorption and other unpleasant side effects.

Brown adipose tissue (BAT) is responsible for cold- and diet-induced thermogenesis that significantly contributes to the control of body temperature and energy expenditure. Physiol Rev. 2004; 84:277-359. Literature reports indicate that BAT thermogenesis is principally dependent on the β-adrenergically mediated activation of lipolysis and subsequent degradation of fatty acids, which generates heat dependent on uncoupling protein 1 (UCP1) that uncouples mitochondrial oxidative phosphorylation to dissipate the electrochemical gradient as heat instead of ATP synthesis. Diabetes 2009; 58:1526-1531. Traditional thiazolidinediones such as pioglitazone can increase differentiation of BAT and increase BAT stores in mammals. Biochemical Pharmacology 1996; 52:639-701. However, many thiazolidinediones evaluated for clinical development were shown to activate PPARγ, which ultimately resulted in the transcription of genes favoring sodium reabsorption, fluid retention, and weight gain in patients. Guan, Y. et al., Nat. Med. (2005) 11:861-866. It is generally believed that this PPARγ agonism is also responsible for the biological activity of these compounds including the differentiation of BAT. Petrovic et al., Am. J. Physiol. Endocrinol. Meta. (2008) 295: E287-E296. Recent studies indicate that these BAT stores are inversely proportional to body mass index, which is an index of obesity. N. Engl. J. Med., 2009; 360:1500-1508.

SUMMARY OF THE INVENTION

The present invention relates to compounds that have reduced binding and/or activation of the nuclear transcription factor PPARγ. Contrary to the teachings of the literature, PPARγ sparing compounds of the present invention are able to stimulate the differentiation of BAT and increase the amount of UCP1 protein.

The compounds of this invention have reduced binding and/or activation of the nuclear transcription factor PPARγ, do not augment sodium re-absorption, and are useful in treating, reducing the severity, or delaying the onset of one or more metabolic diseases (e.g., diabetes, obesity, dyslipidemia, or any combination thereof). Advantageously, the compounds having lower PPARγ activity exhibit fewer side effects than compounds having higher levels of PPARγ activity.

One aspect of the present invention provides a compound of Formula I:

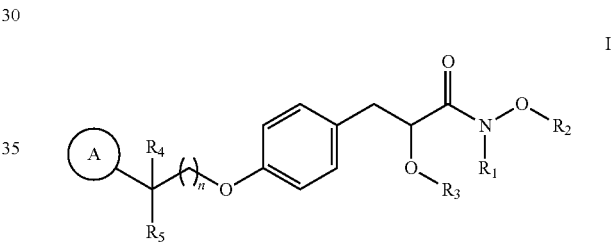

or a pharmaceutically acceptable salt thereof, wherein

Each of $R_1$ and $R_2$ is independently selected from —H, —$C_{1-6}$alkyl, aryl, 5-10 membered heteroaryl, —$C_{3-6}$cycloaliphatic, 3-8 membered heterocycloaliphatic, —$CH_2$-aryl, —$CH_2$-5-10 membered heteroaryl, —$CH_2$—$C_{3-6}$cycloaliphatic, —$CH_2$-3-8 membered heterocycloaliphatic, each of which is optionally substituted with 1-3 groups selected from halo, —OH, or phenyl, or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;

$R_3$ is —$C_{1-6}$ alkyl optionally substituted with 1-3 groups selected from halo, —OH, or phenyl;

each of $R_4$ and $R_5$ is independently selected from —H, —OH, —$NH_2$, —NHC(O)$R_7$, —NHC(O)O$R_7$, —NHS(O)$_2R_7$, —C(O)$R_7$, —C(O)O$R_7$, —$CH_2$O$R_7$, —$CH_2$N($R_7$)$_2$, —$C_{1-6}$ alkyl, each of which is optionally substituted with 1-3 groups selected from halo or —OH, or $R_4$ and $R_5$ together form oxo or =N—O—$R_7$;

Ring A is a 5-8 membered saturated, partially unsaturated, or fully unsaturated ring having 0-3 heteroatoms independently selected from N, O, or S, wherein ring A is optionally substituted with 1-3 of $R_6$;

each $R_6$ is independently halo, —H, —CN, —OR$_7$, —NO$_2$, —$C_{1-6}$ alkyl, aryl, 5-10 membered heteroaryl, —S(O)₂R₇, or —C(O)R₇, each of which is optionally substituted with 1-3 groups selected from halo or —OH;

each R₇ is independently —H, —C₁₋₆alkyl, —C₃₋₈ cycloalkyl, or phenyl; and n is 0 or 1.

In some embodiments, R₁ is —H or —C₁₋₆ alkyl. For example, R₁ is —H, methyl, ethyl, propyl, or isopropyl.

In some embodiments, R₂ is —H, —C₁₋₆alkyl, aryl, 5-10 membered heteroaryl, —C₃₋₆ cycloaliphatic, or 3-8 membered heterocycloaliphatic, each of which is optionally substituted with 1-3 groups selected from halo, —OH, or phenyl. For example, R₂ is —H or —C₁₋₆ alkyl. In other examples, R₂ is —H, methyl, ethyl, propyl, or isopropyl.

In some embodiments, R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R₃ is —C₁₋₃alkyl optionally substituted with 1-3 groups selected from halo, —OH, or phenyl. For example, R₃ is methyl or ethyl.

In some embodiments, n is 1. For example, n is 1, and one of R₄ and R₅ is H and the other is independently selected from —H or —OH, or R₄ and R₅ together form oxo.

In some embodiments, n is 0. For example, n is 0, and both of R₄ and R₅ are —H.

In some embodiments, ring A is a 6-membered, saturated, partially unsaturated, or fully unsaturated ring having 0-3 heteroatoms independently selected from N, O, and S, optionally substituted with 1-3 of R₆. For example, ring A is phenyl optionally substituted with 1-3 of R₆. In other examples, ring A is phenyl optionally substituted with halo, —OR₇, or —C₁₋₆alkyl.

In some embodiments, ring A is pyrimidinyl or pyridinyl, either of which is optionally substituted with 1-3 of R₆. For example, ring A is pyridine-2-yl optionally substituted with 1-3 of R₆. In other examples, ring A is pyridine-2-yl optionally substituted with halo, —OR₇, or —C₁₋₆alkyl.

In some embodiments, R₇ is methyl, ethyl, or propyl.

In some embodiments, R₆ is methyl, ethyl, or propyl.

Another aspect of the present invention provides a compound of Formula II:

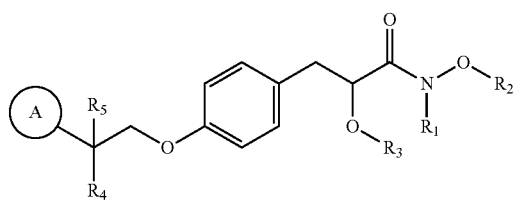

II or a pharmaceutically acceptable salt thereof, wherein:

Each of R₁ and R₂ is independently selected from —H, —C₁₋₆ alkyl, aryl, 5-10 membered heteroaryl, —C₃₋₆ cycloaliphatic, 3-8 membered heterocycloaliphatic, —CH₂— aryl, —CH₂-5-10 membered heteroaryl, —CH₂—C₃₋₆cycloaliphatic, —CH₂-3-8 membered heterocycloaliphatic, each of which is optionally substituted with 1-3 groups selected from halo, —OH, or phenyl, or R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S;

R₃ is —C₁₋₆alkyl optionally substituted with 1-3 groups selected from halo, —OH, or phenyl;

each of R₄ and R₅ is independently selected from —H, —OH, —NH₂, —NHC(O)R₇, —NHC(O)OR₇, —NHS(O)₂R₇, —C(O)R₇, —C(O)OR₇, —CH₂OR₇, —CH₂N(R₇)₂, —C₁₋₆alkyl, each of which is optionally substituted with 1-3 groups selected from halo or —OH, or R₄ and R₅ together form oxo or =N—O—R₇;

Ring A is a 5-8 membered saturated, partially unsaturated, or fully unsaturated ring having 0-3 heteroatoms independently selected from N, O, or S, wherein ring A is optionally substituted with 1-3 of R₆;

each R₆ is independently halo, —H, —CN, —OR₇, —NO₂, —C₁₋₆ alkyl, aryl, 5-10 membered heteroaryl, —S(O)₂R₇, or —C(O)R₇, each of which is optionally substituted with 1-3 groups selected from halo or —OH; and each R₇ is independently —H, —C₁₋₆alkyl, —C₃₋₈cycloalkyl, or phenyl.

In some embodiments, R₁ is —H or —C₁₋₆alkyl. For example, R₁ is —H, methyl, ethyl, propyl, or isopropyl.

In some embodiments, R₂ is —H, —C₁₋₆ alkyl, aryl, 5-10 membered heteroaryl, —C₃₋₆cycloaliphatic, or 3-8 membered heterocycloaliphatic, each of which is optionally substituted with 1-3 groups selected from halo, —OH, or phenyl. For example, R₂ is —H or —C₁₋₆alkyl. For example, R₂ is —H, methyl, ethyl, propyl, or isopropyl.

In some embodiments, R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R₃ is —C₁₋₃ alkyl optionally substituted with 1-3 groups selected from halo, —OH, or phenyl. For example, R₃ is methyl or ethyl.

In some embodiments, one of R₄ and R₅ is H and the other is independently selected from —H or —OH, or R₄ and R₅ together form oxo. For example, both of R₄ and R₅ are —H.

In some embodiments, ring A is a 6-membered, saturated, partially unsaturated, or fully unsaturated ring having 0-3 heteroatoms independently selected from N, O, and S, optionally substituted with 1-3 of R₆. For example, ring A is phenyl optionally substituted with 1-3 of R₆. In other examples, ring A is phenyl optionally substituted with halo, —OR₇, or —C₁₋₆ alkyl.

In some embodiments, ring A is pyrimidinyl or pyridinyl, either of which is optionally substituted with 1-3 of R₆. For example, ring A is pyridine-2-yl optionally substituted with 1-3 of R₆. In other examples, ring A is pyridine-2-yl optionally substituted with halo, —OR₇, or —C₁₋₆ alkyl.

In some embodiments, R₇ is methyl, ethyl, or propyl.

In some embodiments, R₆ is methyl, ethyl, or propyl.

Another aspect of the present invention provides a compound of Formula IIa:

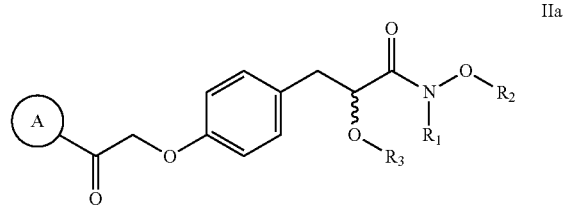

IIa or a pharmaceutically acceptable salt thereof, wherein R₁, R₂, R₃, and ring A are as defined above in the compound of Formula I, and R₄ₐ Is independently selected from —OH, —NH₂, —NHC(O)R₇, —NHC(O)OR₇, —NHS(O)₂R₇, —C(O)R₇, —C(O)OR₇, —CH₂OR₇, —CH₂N(R₇)₂, —C₁₋₆ alkyl, each of which is optionally substituted with 1-3 groups selected from halo or —OH.

In some embodiments, R₄ₐ is —OH.

Another aspect of the present invention provides a compound of Formula IIa-1:

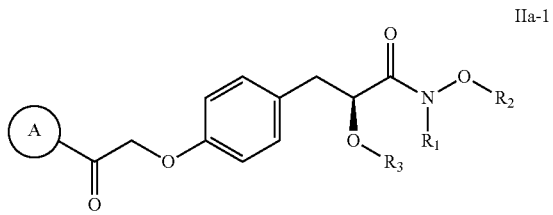

IIa-1 or a pharmaceutically acceptable salt thereof, wherein $R_1$, $R_2$, $R_3$, and ring A are as defined above in the compound of Formula I.

In some embodiments, the compound of Formula II is a compound of Formula IIa-2:

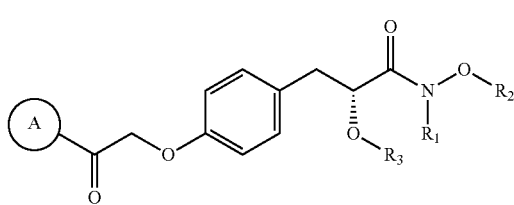

IIa-2 or a pharmaceutically acceptable salt thereof, wherein $R_1$, $R_2$, $R_3$, and ring A are as defined above in the compound of Formula I.

Another aspect of the present invention provides a compound of Formula IIb:

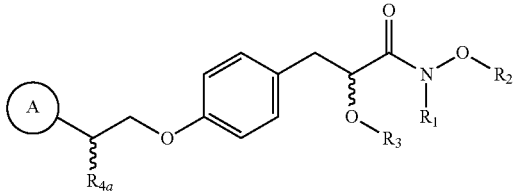

IIb or a pharmaceutically acceptable salt thereof, wherein $R_1$, $R_2$, $R_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

In some embodiments, the compound of Formula II is a compound of Formula IIb-1:

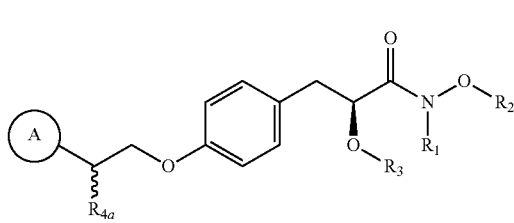

IIb-1 or a pharmaceutically acceptable salt thereof, wherein $R_1$, $R_2$, $R_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

In some embodiments, the compound of Formula IIb-1 is a compound of Formula IIb-1a, IIb-1c, or IIb-1d:

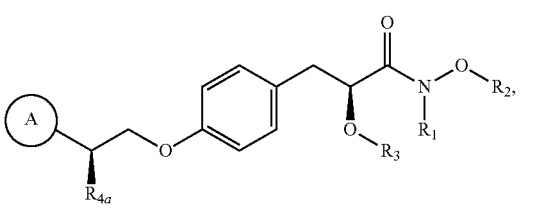

IIb-1a

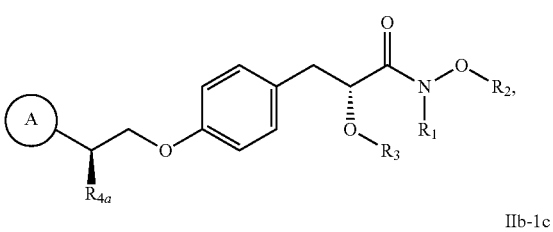

IIb-1b

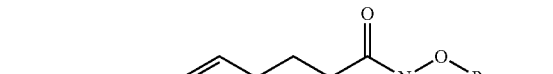

IIb-1c

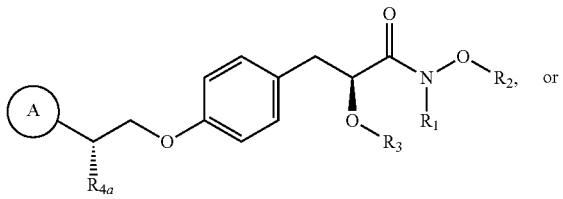

IIb-1d or a pharmaceutically acceptable salt thereof, wherein $R_1$, $R_2$, $R_3$, and ring A are as defined above in the compound of Formula I and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_h$ is —OH.

In some embodiments, the compound of Formula II is a compound of Formula IIb-2:

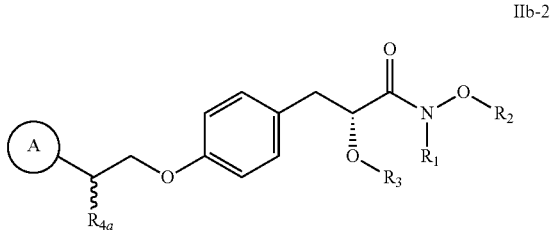

IIb-2 or a pharmaceutically acceptable salt thereof, wherein $R_1$, $R_2$, $R_3$, and ring A are as defined above in the compound of Formula I and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$alkyl, each of which is optionally substituted with 1-3 groups selected from halo or —OH.

In some embodiments, $R_{4a}$ is —OH.

In some embodiments, the compound of Formula II is a compound of Formula IIb-3:

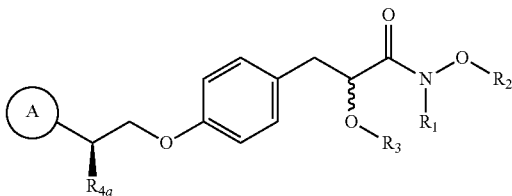

IIb-3 or a pharmaceutically acceptable salt thereof, wherein R$_1$, R$_2$, R$_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$alkyl, each of which is optionally substituted with 1-3 groups selected from halo or —OH.

In some embodiments, $R_{4a}$ is —OH.

In some embodiments, the compound of Formula II is a compound of Formula IIb-4:

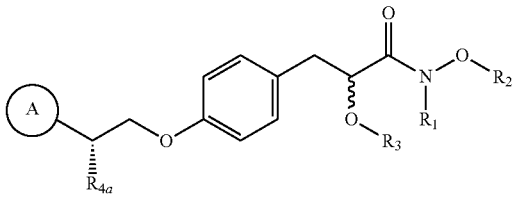

IIb-4 or a pharmaceutically acceptable salt thereof, wherein R$_1$, R$_2$, R$_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

Another aspect of the present invention provides a compound of Formula III:

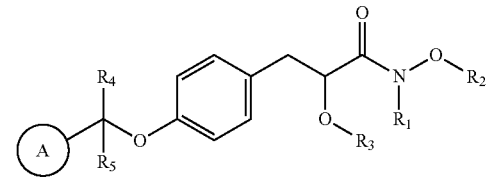

III or a pharmaceutically acceptable salt thereof, wherein:

Each of R$_1$ and R$_2$ is independently selected from —H, —C$_{1-6}$alkyl, aryl, 5-10 membered heteroaryl, —C$_{3-6}$cycloaliphatic, 3-8 membered heterocycloaliphatic, —CH$_2$-aryl, —CH$_2$-5-10 membered heteroaryl, —CH$_2$—C$_{3-8}$cycloaliphatic, —CH$_2$-3-8 membered heterocycloaliphatic, each of which is optionally substituted with 1-3 groups selected from halo, —OH, or phenyl, or R$_1$ and R$_2$ together with the atoms to which they are attached form an optionally substituted 5-8 membered saturated or partially unsaturated heterocyclic ring that includes an N atom, an O atom, and up to 1 additional heteroatom selected from N, O, or S;

R$_3$ is —C$_{1-6}$ alkyl optionally substituted with 1-3 groups selected from halo, —OH, or phenyl;

each of R$_4$ and R$_5$ is independently selected from —H, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH;

Ring A is a 5-8 membered saturated, partially unsaturated, or fully unsaturated ring having 0-3 heteroatoms independently selected from N, O, or S, wherein ring A is optionally substituted with 1-3 of R$_6$;

each R$_6$ is independently halo, —H, —CN, —OR$_7$, —NO$_2$, —C$_{1-6}$ alkyl, aryl, 5-10 membered heteroaryl, —S(O)$_2$R$_7$, or —C(O)R$_7$, each of which is optionally substituted with 1-3 groups selected from halo or —OH; and each R$_7$ is independently —H, —C$_{1-6}$ alkyl, —C$_{3-8}$ cycloalkyl, or phenyl.

In some embodiments, R$_1$ is —H or —C$_{1-6}$alkyl. For example, R$_1$ is —H, methyl, ethyl, propyl, or isopropyl.

In some embodiments, R$_2$ is —H, —C$_{1-6}$ alkyl, aryl, 5-10 membered heteroaryl, —C$_{3-6}$ cycloaliphatic, or 3-8 membered heterocycloaliphatic, each of which is optionally substituted with 1-3 groups selected from halo, —OH, or phenyl. For example, R$_2$ is —H or —C$_{1-6}$ alkyl. In other examples, R$_2$ is —H, methyl, ethyl, propyl, or isopropyl.

In some embodiments, R$_1$ and R$_2$ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R$_3$ is —C$_{1-3}$ alkyl optionally substituted with 1-3 groups selected from halo, —OH, or phenyl. For example, R$_3$ is methyl or ethyl.

In some embodiments, one of R$_4$ and R$_5$ is H and the other is independently selected from —H or —OH. For example, both of R$_4$ and R$_5$ are —H.

In some embodiments, ring A is a 6-membered, saturated, partially unsaturated, or fully unsaturated ring having 0-3 heteroatoms independently selected from N, O, and S, optionally substituted with 1-3 of R$_6$. For example, ring A is phenyl optionally substituted with 1-3 of R$_6$. In other examples, ring A is phenyl optionally substituted with halo, —OR$_7$, or —C$_{1-6}$ alkyl.

In some embodiments, ring A is pyrimidinyl or pyridinyl, either of which is optionally substituted with 1-3 of R$_6$. For example, ring A is pyridine-2-yl optionally substituted with 1-3 of R$_6$. In other examples, ring A is pyridine-2-yl optionally substituted with halo, —OR$_7$, or —C$_{1-6}$ alkyl.

In some embodiments, R$_7$ is methyl, ethyl, or propyl.

In some embodiments, R$_6$ is methyl, ethyl, or propyl.

In some embodiments, the compound of Formula III is a compound of Formula IIIa:

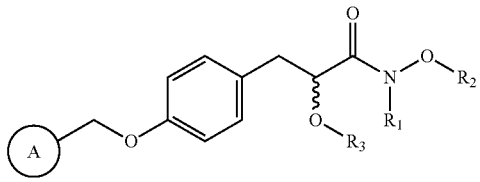

IIIa or a pharmaceutically acceptable salt thereof, wherein $R_1$, $R_2$, $R_3$, and ring A are as defined above in the compound of Formula I.

In some embodiments, the compound of Formula III is a compound of Formula IIIb-1:

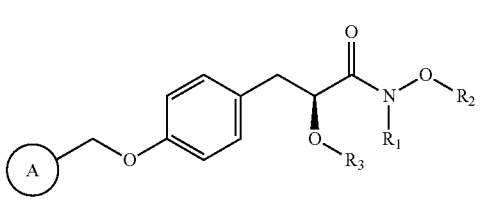

IIIb-1 or a pharmaceutically acceptable salt thereof, wherein $R_1$, $R_2$, $R_3$, and ring A are as defined above in the compound of Formula I.

In some embodiments, the compound of Formula III is a compound of Formula IIIb-2:

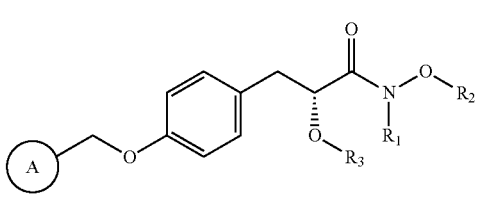

IIIb-2 or a pharmaceutically acceptable salt thereof, wherein $R_1$, $R_2$, $R_3$, and ring A are as defined above in the compound of Formula I.

Another aspect of the present invention provides a compound selected from Table 1, below.

Another aspect of the present invention provides a pharmaceutical composition comprising a compound as described herein.

Another aspect of the present invention provides a method of delaying the onset, reducing the symptoms, or treating a metabolic mediated disorder comprising administering to a patient in need thereof a compound, as described herein, or a pharmaceutical composition, as described herein.

In some implementations, the metabolic mediated disorder is selected from diabetes mellitus, obesity, dyslipidemia, hypertension, or any combination thereof.

Some methods further comprise administering to the patient in need thereof a co-therapy selected from metformin, sitagliptin, vildagliptin, atorvastatin, cerivastatin, fluvastatin, lovastatin, mevastatin, simvastatin, rosuvastatin, pravastatin, or any pharmaceutically acceptable combination thereof.

DETAILED DESCRIPTION OF THE INVENTION

The present invention provides hydroxamate compounds and pharmaceutical compositions that are useful for delaying the onset, reducing the severity of symptoms, or treating a metabolic mediated disorder.

I. DEFINITIONS

As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-3, 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic) alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzo fused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl) aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (aralphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (aralphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (aralphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfonyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (aralphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (aralphatic)carbonylamino, (heterocycloaliphatic)carbonylamino, ((heterocycloaliphatic) aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (aralphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocycloaliphatic ring system or bicyclic cycloaliphatic ring system in which the rings are bridged. Examples of bridged bicyclic ring systems include, but are not limited to, adamantanyl, norbomanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—, respectively. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S—when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic (amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$— where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, R$_3$, R$_4$, R$_{4a}$, R$_5$, R$_6$, R$_7$ and other variables and groups (e.g., ring A) contained in Formula I, described herein, encompass specific groups, such as alkyl and aryl. Unless otherwise noted, each of the specific groups for the variables R$_1$, R$_2$, R$_3$, R$_4$, R$_{4a}$, R$_5$, R$_6$, R$_7$ and other variables contained therein and groups (e.g., ring A) can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl) carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C-$ or $^{14}C-$ enriched carbon are within the scope of this invention. Such compounds are useful, for example, as analytical tools or probes in biological assays, or as therapeutic agents.

As used herein, an "adrenergic agonist" refers to any compound having agonistic activity toward any adrenergic receptor (e.g., $\beta_1$, $\beta_2$, $\beta_3$). Note that the terms "beta-adrenergic" and "β-adrenergic" are used interchangeably. This usage also applies to sub-types of beta agonists, (e.g., 'beta-1-adrenergic agonist' is used interchangeable with 'β1-adrenergic agonist' and/or '$\beta_1$-adrenergic agonist').

As used herein, the term "delaying the onset" of a disease (e.g., diabetes, obesity, a neurodegenerative disease, or any combination thereof) refers to a delay of symptoms of a disease, wherein the delay is caused by the administration of a therapeutic agent (e.g., compound, compound salt, or pharmaceutical composition). The delay of symptoms need not last for the duration of the patient's life, although the delay may last for this duration.

Chemical structures and nomenclature are derived from ChemDraw, version 11.0.1, Cambridge, Mass.

II. Abbreviations

The following abbreviations are used herein:
Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
MeOH methanol
MTBE methyl tert-butyl ether
DMF N,N-dimethylformamide
DMA N,N-dimethylacetamide
DMSO dimethyl sulfoxide
HOAc acetic acid
TFA trifluoroacetic acid
$Et_3N$ triethylamine
DIPEA diisopropylethylamine
DIEA diisopropylethylamine
$K_2CO_3$ dipotassium carbonate
$Na_2CO_3$ disodium carbonate
NaOH sodium hydroxide
$K_3PO_4$ tripotassium phosphate
HPLC high performance liquid chromtagraphy
Hr or h hours
atm atmospheres
rt or RT room temperature
HCl hydrochloric acid
HBr hydrobromic acid
$H_2O$ water
NaOAc sodium acetate
$H_2SO_4$ sulfuric acid
$N_2$ nitrogen gas
$H_2$ hydrogen gas
$Br_2$ bromine
n-BuLi n-butyl lithium
$Pd(OAc)_2$ palladium(II)acetate
$PPh_3$ triphenylphosphine
rpm revolutions per minute
Equiv. equivalents
Ts tosyl
IPA isopropyl alcohol As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

III. Compounds And Compositions

Compounds of the present invention are uniquely effective in treating, reducing the severity of, or delaying the onset of one or more metabolic mediated disorders including diabetes, obesity, dyslipidemia, or any combination thereof and possess a reduced interaction with PPARγ. Accordingly, these compounds demonstrate reduced side effects related to PPARγ interaction than PPARγ activating compounds such as pioglitazine and rosiglitazone.

The present invention is directed to a compound of Formula I:

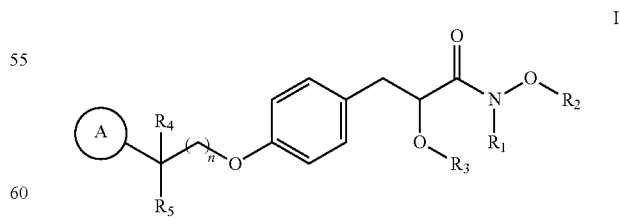

or a pharmaceutically acceptable salt thereof, wherein
Each of $R_1$ and $R_2$ is independently selected from —H, —$C_{1-6}$alkyl, aryl, 5-10 membered heteroaryl, —$C_{3-6}$cycloaliphatic, 3-8 membered heterocycloaliphatic, —$CH_2$-aryl, —$CH_2$-5-10 membered heteroaryl, —$CH_2$—$C_{3-6}$cycloaliphatic, —CH₂-3-8 membered heterocycloaliphatic, each of which is optionally substituted with 1-3 groups selected from halo, —OH, or phenyl, or R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S;

R₃ is —C₁₋₆alkyl optionally substituted with 1-3 groups selected from halo, —OH, or phenyl;

each of R₄ and R₅ is independently selected from —H, —OH, —NH₂, —NHC(O)R₇, —NHC(O)OR₇, —NHS(O)₂R₇, —C(O)R₇, —C(O)OR₇, —CH₂OR₇, —CH₂N(R₇)₂, —C₁₋₆ alkyl, each of which is optionally substituted with 1-3 groups selected from halo or —OH, or R₄ and R₅ together form oxo or =N—O—R₇;

Ring A is a 5-8 membered saturated, partially unsaturated, or fully unsaturated ring having 0-3 heteroatoms independently selected from N, O, or S, wherein ring A is optionally substituted with 1-3 of R₆;

each R₆ is independently halo, —H, —CN, —OR₇, —NO₂, —C₁₋₆alkyl, aryl, 5-10 membered heteroaryl, —S(O)₂R₇, or —C(O)R₇, each of which is optionally substituted with 1-3 groups selected from halo or —OH;

each R₇ is independently —H, —C₁₋₆alkyl, —C₃₋₈cycloalkyl, or phenyl; and n is 0 or 1.

In some embodiments, R₁ is —H or —C₁₋₆alkyl. For example, R₁ is —H, methyl, ethyl, propyl, or isopropyl.

In some embodiments, R₂ is —H, —C₁₋₆alkyl, aryl, 6 membered heteroaryl, —C₃₋₆ cycloaliphatic, 3-8 membered heterocycloaliphatic, —CH₂-aryl, —CH₂-6 membered heteroaryl, —CH₂—C₃₋₆cycloaliphatic, or —CH₂-3-8 membered heterocycloaliphatic, each of which is optionally substituted with 1-3 groups selected from halo, —OH, or phenyl. For example, R₂ is —H or —C₁₋₆alkyl. In other examples, R₂ is —H, methyl, ethyl, or propyl.

In other embodiments, R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R₁ and R₂ together with the atoms to which they are attached form a ring selected from

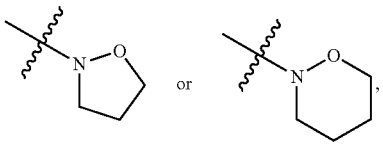 [SMILES: *N1CCCO1 ; *N1CCCCO1]

wherein either ring is optionally substituted.

In some embodiments, R₃ is —C₁₋₃alkyl. For example, R₃ is methyl, ethyl, or propyl.

In some embodiments, n is 1.

In some embodiments, R₄ and R₅ together form oxo.

In some embodiments, R₄ and R₅ together form =N—O—R₇. For example, R₄ and R₅ together form =N—O—C₁₋₄alkyl, =N—O—C₃₋₆cycloalkyl, =N—O-phenyl, =N—O-6 membered heteroaryl, or =N—O-3-8 membered heterocycle.

In other embodiments, n is 0.

In some embodiments, both of R₄ and R₅ are —H.

In some embodiments, one of R₄ and R₅ is H and the other is selected from —H or —OH.

In some embodiments, ring A is a 6-membered, saturated, partially unsaturated, or fully unsaturated ring having 0-3 heteroatoms independently selected from N, O, and S, optionally substituted with 1-3 of R₆. In some examples, ring A is a 6-membered fully unsaturated ring having 0-3 heteroatoms independently selected from N, O, and S, optionally substituted with 1-3 of R₆. For example, ring A is phenyl optionally substituted with 1-3 of R₆.

In some embodiments, ring A is pyrimidinyl or pyridinyl, either of which is optionally substituted with 1-3 of R₆. For example, ring A is pyridine-2-yl optionally substituted with 1-3 of R₆.

In some embodiments, ring A is substituted with 1 of R₆.

In some embodiments, R₆ is C₁₋₆ alkyl or —OR₇, wherein R₇ is H or alkyl.

In some embodiments, R₆ is methoxy, ethoxy, or propoxy.

In some embodiments, R₆ is methyl, ethyl, or propyl.

In some embodiments, ring A is a 6-membered, saturated, partially unsaturated, or fully unsaturated ring having 0-3 heteroatoms independently selected from N, O, and S, optionally substituted with 1-3 of R₆. For example, ring A is phenyl optionally substituted with 1-3 of R₆. In other examples, ring A is phenyl optionally substituted with halo, —OR₇, or —C₁₋₆ alkyl.

In some embodiments, ring A is pyrimidinyl or pyridinyl, either of which is optionally substituted with 1-3 of R₆. For example, ring A is pyridine-2-yl optionally substituted with 1-3 of R₆. In other examples, ring A is pyridine-2-yl optionally substituted with halo, —OR₇, or —C₁₋₆alkyl.

In some embodiments, R₇ is methyl, ethyl, or propyl.

In some embodiments, R₆ is methyl, ethyl, or propyl.

Another aspect is directed to a compound of Formula II:

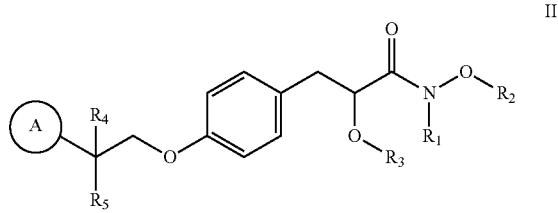

II or a pharmaceutically acceptable salt thereof, wherein:

Each of R₁ and R₂ is independently selected from —H, —C₁₋₄ alkyl, aryl, 5-10 membered heteroaryl, —C₃₋₆cycloaliphatic, 3-8 membered heterocycloaliphatic, —CH₂-aryl, —CH₂-5-10 membered heteroaryl, —CH₂—C₃₋₆ cycloaliphatic, —CH₂-3-8 membered heterocycloaliphatic, each of which is optionally substituted with 1-3 groups selected from halo, —OH, or phenyl, or R₁ and R₂ together with the atoms to which they are attached form an optionally substituted 5-8 membered saturated or partially unsaturated heterocyclic ring that includes an N atom, an O atom, and up to 1 additional heteroatom selected from N, O, or S;

R₃ is —C₁₋₆alkyl optionally substituted with 1-3 groups selected from halo, —OH, or phenyl;

each of R₄ and R₅ is independently selected from —H, —OH, —NH₂, —NHC(O)R₇, —NHC(O)OR₇, —NHS(O)₂R₇, —C(O)R₇, —C(O)OR₇, —CH₂OR₇, —CH₂N(R₇)₂, —C₁₋₆ alkyl, each of which is optionally substituted with 1-3 groups selected from halo or —OH, or R₄ and R₅ together form oxo or =N—O—R₇;

Ring A is a 5-8 membered saturated, partially unsaturated, or fully unsaturated ring having 0-3 heteroatoms independently selected from N, O, or S, wherein ring A is optionally substituted with 1-3 of R₆;

each R₆ is independently halo, —H, —CN, —OR₇, —NO₂, —C₁₋₆alkyl, aryl, 5-10 membered heteroaryl, —S(O)$_2$R$_7$, or —C(O)R$_7$, each of which is optionally substituted with 1-3 groups selected from halo or —OH; and
each R$_7$ is independently —H, —C$_{1-6}$alkyl, —C$_{3-8}$cycloalkyl, or phenyl.

In some embodiments, R$_1$ is —H or —C$_{1-6}$alkyl. For example, R$_1$ is —H, methyl, ethyl, propyl, or isopropyl.

In some embodiments, R$_2$ is —H, —C$_{1-6}$alkyl, aryl, 6-membered heteroaryl, —C$_{3-6}$ cycloaliphatic, 3-8 membered heterocycloaliphatic, —CH$_2$-aryl, —CH$_2$-6 membered heteroaryl, —CH$_2$—C$_{3-6}$cycloaliphatic, or —CH$_2$-3-8 membered heterocycloaliphatic, each of which is optionally substituted with 1-3 groups selected from halo, —OH, or phenyl. For example, R$_2$ is —H or —C$_{1-6}$alkyl. In other examples, R$_2$ is —H, methyl, ethyl, or propyl.

In other embodiments, R$_1$ and R$_2$ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R$_3$ is —C$_{1-3}$ alkyl. For example, R$_3$ is methyl, ethyl, or propyl.

In some embodiments, n is 1.
In some embodiments, R$_4$ and R$_5$ together form oxo.
In other embodiments, n is 0.
In some embodiments, both of R$_4$ and R$_5$ are —H.
In some embodiments, one of R$_4$ and R$_5$ is H and the other is selected from —H or —OH.

In some embodiments, ring A is a 6-membered, saturated, partially unsaturated, or fully unsaturated ring having 0-3 heteroatoms independently selected from N, O, and S, optionally substituted with 1-3 of R$_6$. For example, ring A is phenyl optionally substituted with 1-3 of R$_6$.

In some embodiments, ring A is pyrimidinyl or pyridinyl, either of which is optionally substituted with 1-3 of R$_6$. For example, ring A is pyridine-2-yl optionally substituted with 1-3 of R$_6$.

In some embodiments, ring A is substituted with 1 R$_6$.
In some embodiments, R$_6$ is C$_{1-6}$ alkyl or —OR$_7$, wherein R$_7$ is —H or C$_{1-6}$alkyl.
In some embodiments, R$_6$ is methoxy, ethoxy, or propoxy.
In some embodiments, R$_6$ is methyl, ethyl, or propyl.

In some embodiments, ring A is a 6-membered, saturated, partially unsaturated, or fully unsaturated ring having 0-3 heteroatoms independently selected from N, O, and S, optionally substituted with 1-3 of R$_6$. For example, ring A is phenyl optionally substituted with 1-3 of R$_6$. In other examples, ring A is phenyl optionally substituted with halo, —OR$_7$, or —C$_{1-6}$alkyl.

In some embodiments, ring A is pyrimidinyl or pyridinyl, either of which is optionally substituted with 1-3 of R$_6$. For example, ring A is pyridine-2-yl optionally substituted with 1-3 of R$_6$. In other examples, ring A is pyridine-2-yl optionally substituted with halo, —OR$_7$, or —C$_{1-6}$alkyl.

In some embodiments, R$_7$ is methyl, ethyl, or propyl.
In some embodiments, R$_6$ is methyl, ethyl, or propyl.

Another aspect of the present invention provides a compound of Formula IIa:

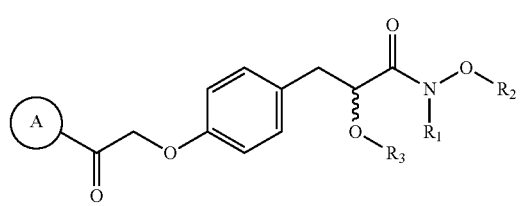

IIa or a pharmaceutically acceptable salt thereof, wherein R$_1$, R$_2$, R$_3$, and ring A are as defined above in the compound of Formula I.

In some embodiments, R$_1$ is —H or —C$_{1-6}$alkyl. For example, R$_1$ is —H, methyl, ethyl, propyl, or isopropyl. In other examples, R$_1$ is —H, methyl, or ethyl.

In some embodiments, R$_2$ is —H or —C$_{1-6}$alkyl.
In some embodiments, R$_3$ is methyl, ethyl, or propyl.
In some embodiments, ring A is phenyl optionally substituted with 1-2 of R$_6$.
In some embodiments, ring A is pyridine-2-yl optionally substituted with 1-2 of R$_6$.

Another aspect of the present invention provides a compound of Formula IIa-1:

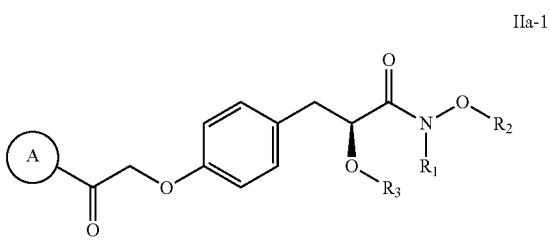

IIa-1 or a pharmaceutically acceptable salt thereof, wherein R$_1$, R$_2$, R$_3$, and ring A are as defined above in the compound of Formula I.

Another aspect of the present invention provides a compound of Formula IIb:

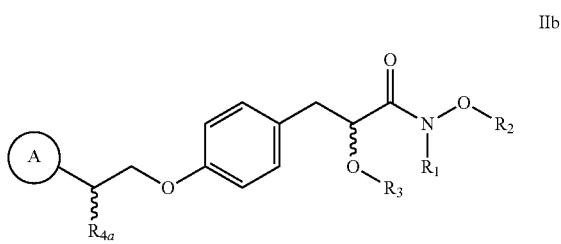

IIb or a pharmaceutically acceptable salt thereof, wherein R$_1$, R$_2$, R$_3$, and ring A are as defined above in the compound of Formula I, and R$_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, R$_{4a}$ is —OH.

Another aspect of the present invention provides a compound of Formula IIb-1:

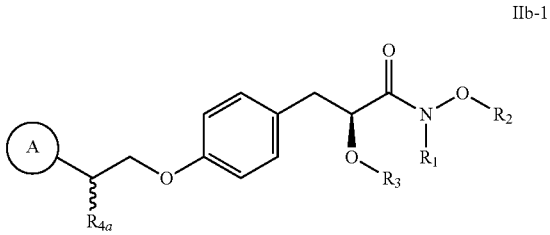

IIb-1 or a pharmaceutically acceptable salt thereof, wherein R$_1$, R$_2$, R$_3$, and ring A are as defined above in the compound of Formula I, and R$_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

In some embodiments, the compound of Formula IIb-1 is a compound of Formula IIb-1a, IIb-1b, IIb-1c, or IIb-1d:

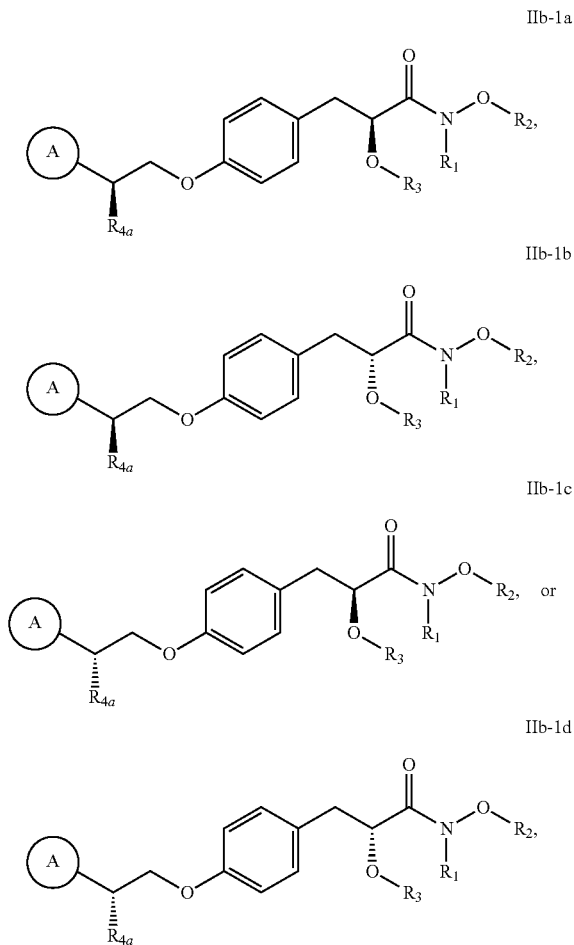

IIb-1a

IIb-1b

IIb-1c

IIb-1d or a pharmaceutically acceptable salt thereof, wherein $R_1$, $R_2$, $R_3$, and ring A are as defined above in the compound of Formula I and $R_{4a}$ is independently selected from —OH, —NH), —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

Another aspect of the present invention provides a compound of Formula IIb-2:

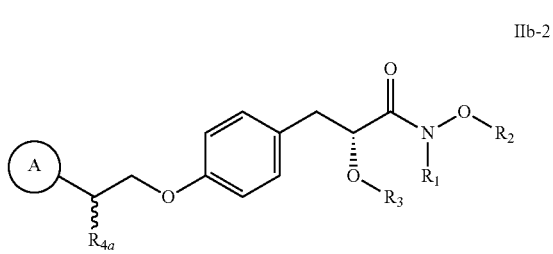

IIb-2 or a pharmaceutically acceptable salt thereof, wherein $R_1$, $R_2$, $R_3$, and ring A are as defined above in the compound of Formula I and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

Another aspect of the present invention provides a compound of Formula IIb-3:

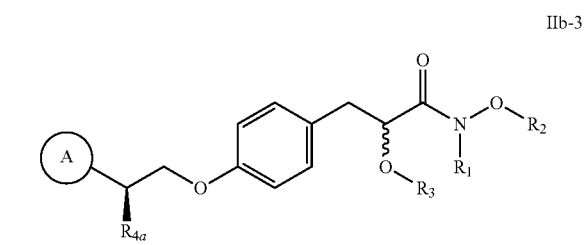

IIb-3 or a pharmaceutically acceptable salt thereof, wherein $R_1$, $R_2$, $R_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

Another aspect of the present invention provides a compound of Formula IIb-4:

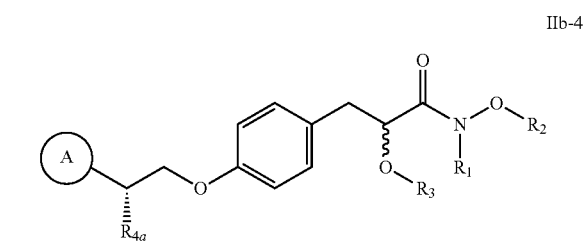

IIb-4 or a pharmaceutically acceptable salt thereof, wherein $R_1$, $R_2$, $R_3$, and ring A are as defined above in the compound of Formula I, and $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

In some embodiments, $R_{4a}$ is —OH.

Another aspect of the present invention provides a compound of Formula III:

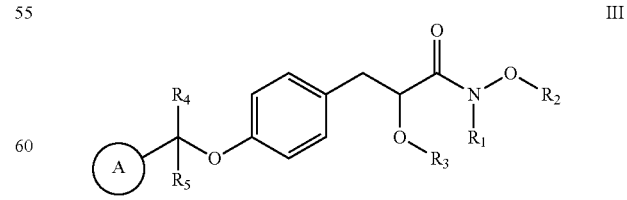

III or a pharmaceutically acceptable salt thereof, wherein:

Each of $R_1$ and $R_2$ is independently selected from —H, —C$_{1-6}$alkyl, aryl, 5-10 membered heteroaryl, —C$_{3-6}$cycloaliphatic, 3-8 membered heterocycloaliphatic, —CH$_2$-aryl, —CH$_2$-5-10 membered heteroaryl, —CH$_2$—C$_{3-6}$ cycloaliphatic, —CH$_2$-3-8 membered heterocycloaliphatic, each of which is optionally substituted with 1-3 groups selected from halo, —OH, or phenyl, or R$_1$ and R$_2$ together with the atoms to which they are attached form an optionally substituted 5-8 membered saturated or partially unsaturated heterocyclic ring that includes an N atom, an O atom, and up to 1 additional heteroatom selected from N, O, or S;

R$_3$ is —C$_{1-6}$ alkyl optionally substituted with 1-3 groups selected from halo, —OH, or phenyl;

each of R$_4$ and R$_5$ is independently selected from —H, —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$alkyl, each of which is optionally substituted with 1-3 groups selected from halo or —OH, or R$_4$ and R$_5$ together form oxo or =N—O—R$_7$;

Ring A is a 5-8 membered saturated, partially unsaturated, or fully unsaturated ring having 0-3 heteroatoms independently selected from N, O, or S, wherein ring A is optionally substituted with 1-3 of R$_6$;

each R$_6$ is independently halo, —H, —CN, —OR$_7$, —NO$_2$, —C$_{1-6}$alkyl, aryl, 5-10 membered heteroaryl, —S(O)$_2$R$_7$, or —C(O)R$_7$, each of which is optionally substituted with 1-3 groups selected from halo or —OH; and each R$_7$ is independently —H, —C$_{1-6}$alkyl, —C$_{3-8}$ cycloalkyl, or phenyl.

In some embodiments, R$_1$ is —H or —C$_{1-6}$alkyl. For example, R$_1$ is —H, methyl, ethyl, propyl, or isopropyl.

In some embodiments, R$_2$ is —H, —C$_{1-6}$alkyl, aryl, 5-10 membered heteroaryl, —C$_{3-6}$ cycloaliphatic, or 3-8 membered heterocycloaliphatic, each of which is optionally substituted with 1-3 groups selected from halo, —OH, or phenyl. For example, R$_2$ is —H or —C$_{1-6}$alkyl. In other examples, R$_2$ is —H, methyl, ethyl, propyl, or isopropyl.

In some embodiments, R$_1$ and R$_2$ together with the atoms to which they are attached form an optionally substituted 5-8 membered saturated or partially unsaturated heterocyclic ring that includes an N atom, an O atom, and up to 1 additional heteroatom selected from N, O, or S.

In some embodiments, R$_3$ is —C$_{1-3}$ alkyl optionally substituted with 1-3 groups selected from halo, —OH, or phenyl. For example, R$_3$ is methyl or ethyl.

In some embodiments, one of R$_4$ and R$_5$ is H and the other is independently selected from —H or —OH. For example, both of R$_4$ and R$_5$ are —H.

In some embodiments, ring A is a 6-membered, saturated, partially unsaturated, or fully unsaturated ring having 0-3 heteroatoms independently selected from N, O, and S, optionally substituted with 1-3 of R$_6$. For example, ring A is phenyl optionally substituted with 1-3 of R$_6$. In other examples, ring A is phenyl optionally substituted with halo, —OR$_7$, or —C$_{1-6}$ alkyl.

In some embodiments, ring A is pyrimidinyl or pyridinyl, either of which is optionally substituted with 1-3 of R$_6$. For example, ring A is pyridine-2-yl optionally substituted with 1-3 of R$_6$. In other examples, ring A is pyridine-2-yl optionally substituted with halo, —OR$_7$, or —C$_{1-6}$ alkyl.

In some embodiments, R$_7$ is methyl, ethyl, or propyl.
In some embodiments, R$_6$ is methyl, ethyl, or propyl.

Another aspect of the present invention provides a compound of Formula IIIa:

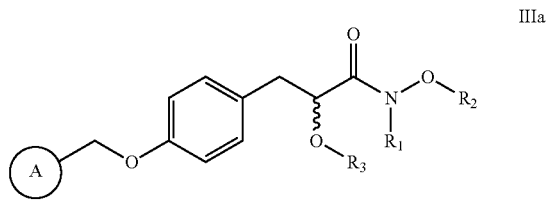

IIIa or a pharmaceutically acceptable salt thereof, wherein R$_1$, R$_2$, R$_3$, and ring A are as defined above in the compound of Formula I.

Another aspect of the present invention provides a compound of Formula IIIb-1:

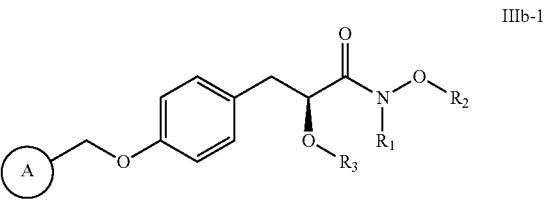

IIIb-1 or a pharmaceutically acceptable salt thereof, wherein R$_1$, R$_2$, R$_3$, and ring A are as defined above in the compound of Formula I.

Another aspect of the present invention provides a compound of Formula IIIb-2:

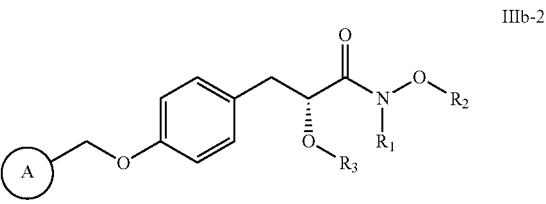

IIIb-2 or a pharmaceutically acceptable salt thereof, wherein R$_1$, R$_2$, R$_3$, and ring A are as defined above in the compound of Formula I.

In some embodiments, the compound of Formula I is selected from the compounds described in Table 1:

TABLE 1

Examples of Compounds of Formula I.

| Compound | Structure |
|---|---|
| 1 | 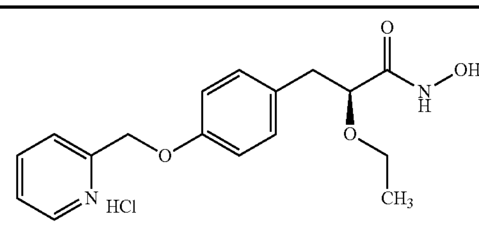 |

TABLE 1-continued

Examples of Compounds of Formula I.

| Compound | Structure |
|---|---|
| 2 | 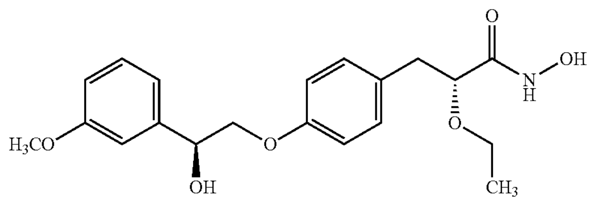 [SMILES: CCO[C@H](Cc1ccc(OC[C@@H](O)c2cccc(OC)c2)cc1)C(=O)NO] |
| 3 | 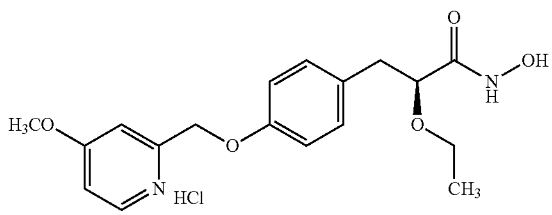 [SMILES: CCO[C@@H](Cc1ccc(OCc2cc(OC)ccn2)cc1)C(=O)NO ; Cl] |
| 4 | 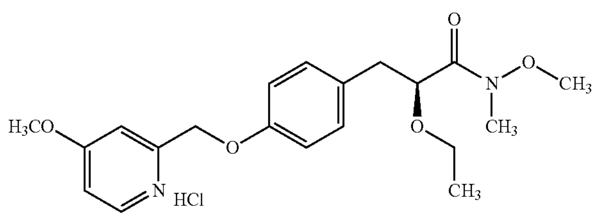 [SMILES: CCO[C@@H](Cc1ccc(OCc2cc(OC)ccn2)cc1)C(=O)N(C)OC ; Cl] |
| 5 | 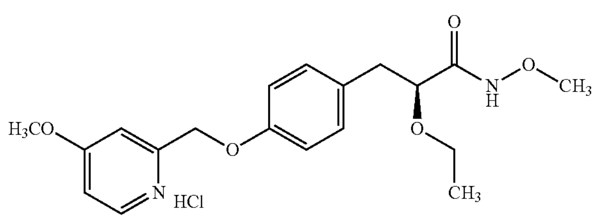 [SMILES: CCO[C@@H](Cc1ccc(OCc2cc(OC)ccn2)cc1)C(=O)NOC ; Cl] |
| 6 | 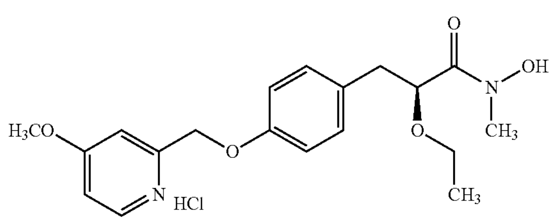 [SMILES: CCO[C@@H](Cc1ccc(OCc2cc(OC)ccn2)cc1)C(=O)N(C)O ; Cl] |
| 7 | 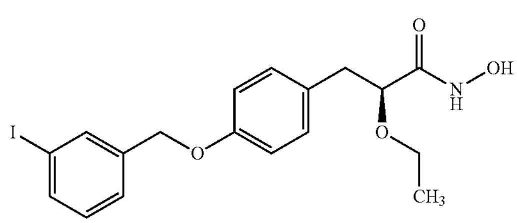 [SMILES: CCO[C@@H](Cc1ccc(OCc2cccc(I)c2)cc1)C(=O)NO] |
| 8 | 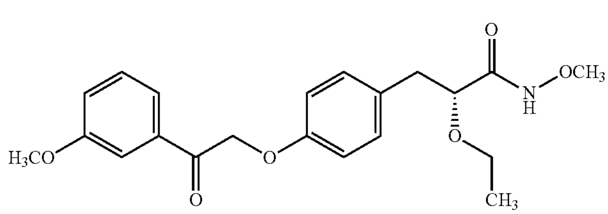 [SMILES: CCO[C@H](Cc1ccc(OCC(=O)c2cccc(OC)c2)cc1)C(=O)NOC] |

TABLE 1-continued

Examples of Compounds of Formula I.

| Compound | Structure |
|---|---|
| 9 | 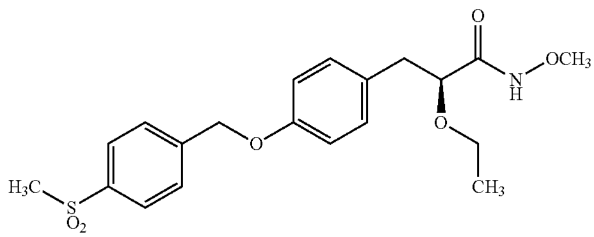 [SMILES: CCO[C@@H](Cc1ccc(OCc2ccc(S(C)(=O)=O)cc2)cc1)C(=O)NOC] |
| 10 | 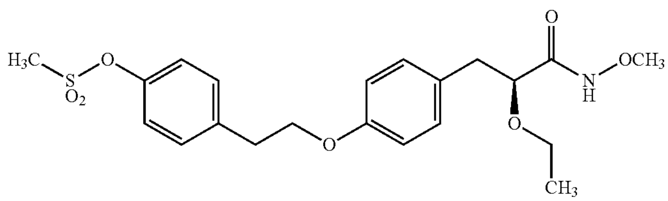 [SMILES: CCO[C@@H](Cc1ccc(OCCc2ccc(OS(C)(=O)=O)cc2)cc1)C(=O)NOC] |
| 11 | 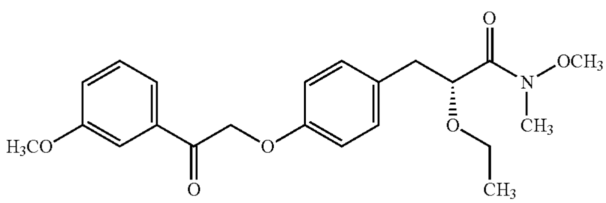 [SMILES: CCO[C@H](Cc1ccc(OCC(=O)c2cccc(OC)c2)cc1)C(=O)N(C)OC] |
| 12 | 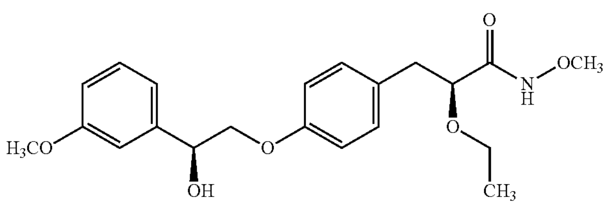 |
| 13 | 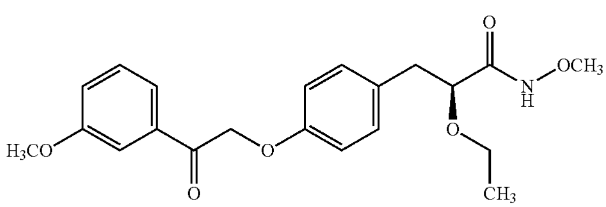 [SMILES: CCO[C@@H](Cc1ccc(OCC(=O)c2cccc(OC)c2)cc1)C(=O)NOC] |
| 14 | 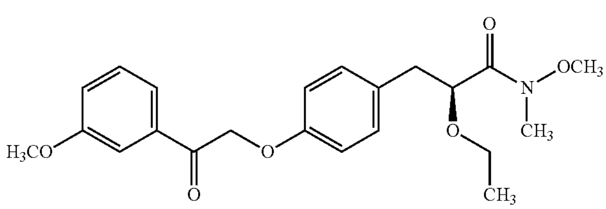 [SMILES: CCO[C@@H](Cc1ccc(OCC(=O)c2cccc(OC)c2)cc1)C(=O)N(C)OC] |
| 15 | 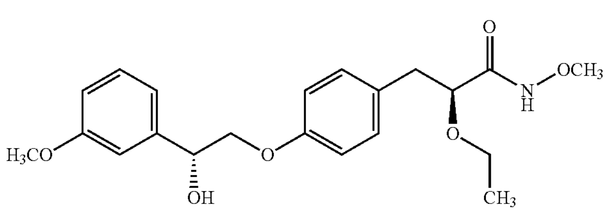 [SMILES: CCO[C@@H](Cc1ccc(OC[C@H](O)c2cccc(OC)c2)cc1)C(=O)NOC] |

TABLE 1-continued

Examples of Compounds of Formula I.

| Compound | Structure |
|---|---|
| 16 | 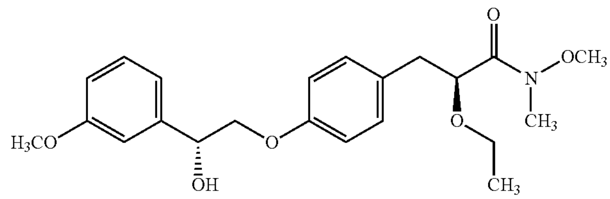 [SMILES: CCO[C@@H](Cc1ccc(OC[C@H](O)c2cccc(OC)c2)cc1)C(=O)N(C)OC] |
| 17 | 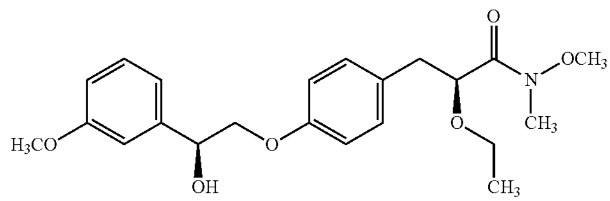 [SMILES: CCO[C@@H](Cc1ccc(OC[C@@H](O)c2cccc(OC)c2)cc1)C(=O)N(C)OC] |
| 18 | 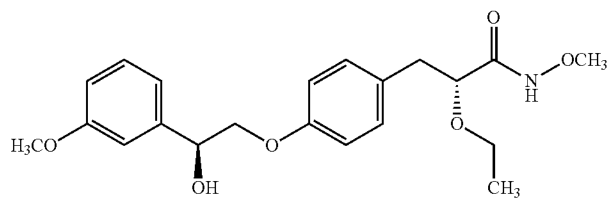 [SMILES: CCO[C@H](Cc1ccc(OC[C@@H](O)c2cccc(OC)c2)cc1)C(=O)NOC] |
| 19 | 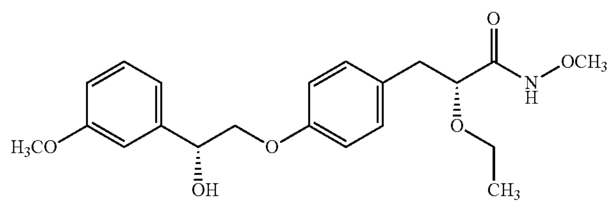 [SMILES: CCO[C@H](Cc1ccc(OC[C@H](O)c2cccc(OC)c2)cc1)C(=O)NOC] |
| 20 | 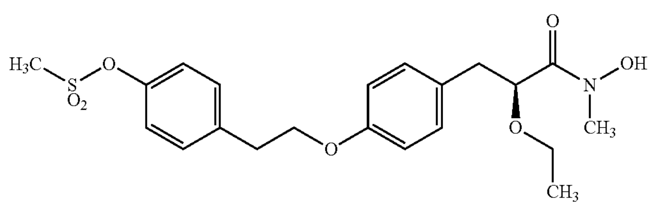 [SMILES: CCO[C@@H](Cc1ccc(OCCc2ccc(OS(C)(=O)=O)cc2)cc1)C(=O)N(C)O] |
| 21 | 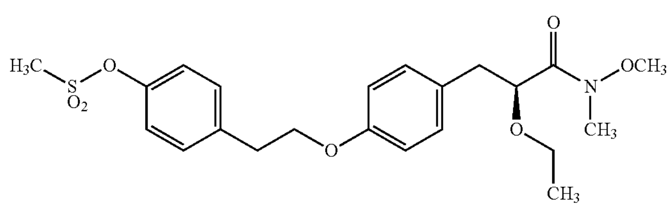 [SMILES: CCO[C@@H](Cc1ccc(OCCc2ccc(OS(C)(=O)=O)cc2)cc1)C(=O)N(C)OC] |

In some embodiments, the compound of Formula I, II, IIa, IIa-1, IIa-2, IIb, IIb-1, IIb-2, IIb-3, IIb-4, III, IIIa, IIIb-1, or IIIb-2 is provided as a salt (e.g., an acid salt or a metal salt (e.g., an alkali metal salt). For example, the compound of formula IIb is provided as a sodium salt, a potassium salt, or a hydrogen chloride salt.

Another aspect of the present invention provides a pharmaceutical composition comprising a compound of Formula I, II, IIa, IIa-1, IIa-2, IIb, IIb-1, IIb-2, IIb-3, IIb-4, III, IIIa, IIIb-1, or a salt thereof (e.g., a sodium salt, a potassium salt, or a HCl salt), and a pharmaceutically acceptable carrier.

In some embodiments, the pharmaceutical composition further comprises a dipeptidyl peptidase IV (DPP-4) inhibitor (e.g., sitagliptin, vildagliptin, or the like); a HMG-CoA reductase inhibitor (e.g., a statin (e.g., atorvastatin, cerivastatin, fluvastatin, lovastatin, mevastatin, simvastatin, rosuvastatin, pravastatin, or any combination thereof)); a GLP-1 or GLP-2 agonist; or any combination thereof.

In some embodiments, the pharmaceutical composition further comprises a β-adrenergic agonist (e.g., a β1-adrenergic agonist, a β2-adrenergic agonist, a β3-adrenergic agonist, or any combination thereof). Non-limiting examples of β-adrenergic agonists include noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or any combination thereof.

In other embodiments, the pharmaceutical composition further comprises a phosphodiesterase inhibitor. Examples of phosphodiesterase inhibitors useful in pharmaceutical compositions of the present invention comprise non-selective inhibitors or selective inhibitors. For instance, the phosphodiesterase inhibitor comprises a non-selective inhibitor selected from caffeine (1,3,7-trimethylxanthine), theobromine (3,7-dimethyl-2,3,6,7-tetrahydro-1H-purine-2,6-dione), theophylline (1,3-dimethyl-7H-purine-2,6-dione), IBMX (3-isobutyl-1-methylxanthine), or any combination thereof. In other examples, the phosphodiesterase inhibitor comprises a selective inhibitor selected from Milrinone (2-methyl-6-oxo-1,6-dihydro-3,4'-bipyridine-5-carbonitrile), Cilostazol (6-[4-(1-cyclohexyl-1H-tetrazol-5-yl)butoxy]-3,4-dihydro-2(1H)-quinolinone), Cilomilast (4-cyano-4-(3-cyclopentyloxy-4-methoxyphenyl)cyclohexane-1-carboxylic acid), Rolipram (4-(3-cyclopentyloxy-4-methoxy-phenyl)pyrrolidin-2-one), Roflumilast (3-(cyclopropylmethoxy)-N-(3,5-dichloropyridin-4-yl)-4-(difluoromethoxy)benzamide), or any combination thereof.

In other embodiments, the pharmaceutical composition further comprises a weight loss drug. Non-limiting examples of weight loss drugs include appetite suppressants (e.g., Meridia, or the like), fat absorption inhibitors (e.g., Xenical, or the like), or compounds that augment sympathomimetic activity such as ephedrine or its various salts.

Pharmaceutical compositions of the present invention can also comprise one or more additional pharmaceutical agents or other drugs. In some embodiments, the pharmaceutical composition further comprises a diuretic, such as hydrochlorothiazide, chlorothaladone, chlorothiazide, or combinations thereof. In some embodiments, the pharmaceutical composition further comprises one or more agents that limit the activity of the rennin-angiotensin system such as angiotensin concerting enzyme inhibitors, i.e. ACE inhibitors, e.g. ramipril, captopril, enalapril, or the like, and/or angiotensin II receptor blockers, i.e. ARBs, e.g., candesartan, losartan, olmesartan, or the like; and/or rennin inhibitors. In other embodiments, the pharmaceutical composition further comprises a compound that limits hypertension by alternate means including β-adrenergic receptor blockers, and calcium channel blockers, e.g., amlodipine. In some embodiments, the pharmaceutical composition further comprises one or more statins, i.e., HMG-CoA reductase inhibitor, e.g., atorvastatin, cerivastatin, fluvastatin, lovastatin, mevastatin, simvastatin, rosuvastatin, pravastatin, or any pharmaceutically acceptable combination thereof.

In another embodiment, the pharmaceutical composition further comprises a GLP analogue such as Exenatide (e.g., Exendin-4), Liraglutide, Taspoglutide, or any combination thereof.

In some embodiments, the pharmaceutical composition further comprises a DPP4 inhibitor such as sitagliptin, vildagliptin, saxagliptin, linagliptin, dutogliptin, gemigliptin, alogliptin, Berberine, or any combination thereof.

In alternative embodiments, the pharmaceutical composition further comprises a phosphodiesterase inhibitor in combination with a beta-adrenergic agonist and at least one additional weight loss drug. Non-limiting examples of other weight loss drugs include appetite suppressants (e.g., Meridia, or the like), fat absorption inhibitors (e.g., Xenical, or the like), or compounds that augment sympathomimetic activity such as ephedrine or its various salts.

Exemplary pharmaceutical compositions according to the present invention include a single unit dosage form having about 1 mg to about 250 mg (e.g., about 10 mg to about 200 mg, about 20 mg to about 150 mg, or about 25 mg to about 125 mg) of a compound of Formula I, II, IIa, IIa-1, IIa-2, IIb, IIb-1, IIb-2, IIb-3, IIb-4, III, IIIa, IIIb-1, or IIIb-2, or a salt thereof.

IV. Methods

Another aspect of the present invention provides a method of treating, reducing the severity of, or delaying the onset of one or more metabolic inflammation mediated diseases comprising administering to a patient in need thereof a compound of Formula I, II, IIa, IIa-1, IIa-2, IIb, IIb-1, IIb-2, IIb-3, IIb-4, III, IIIa, IIIb-1, or IIIb-2, or a pharmaceutically acceptable salt thereof.

As used herein, delaying the onset, reducing the symptoms, or treating a metabolic inflammation mediated disease (e.g., diabetes (e.g., type 1 or type 2 diabetes), hypertension, Alzheimer's disease, Parkinson's disease, Huntington's disease, or dimensia (e.g., early onset dimensia)) includes treating the symptoms of a metabolic inflammation mediated disease or treating the disease itself.

One aspect of the present invention provides a method of treating diabetes (e.g., type 1 or type 2 diabetes) in a patient comprising administering to the patient in need thereof a compound of Formula I:

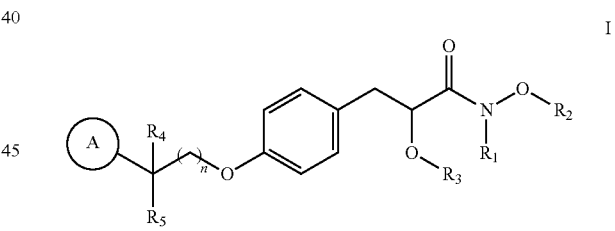

or a pharmaceutically acceptable salt thereof, wherein

Each of $R_1$ and $R_2$ is independently selected from —H, —$C_{1-6}$ alkyl, aryl, 5-10 membered heteroaryl, —$C_{3-6}$ cycloaliphatic, 3-8 membered heterocycloaliphatic, —$CH_2$-aryl, —$CH_2$-5-10 membered heteroaryl, —$CH_2$—$C_{3-6}$ cycloaliphatic, —$CH_2$-3-8 membered heterocycloaliphatic, each of which is optionally substituted with 1-3 groups selected from halo, —OH, or phenyl, or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;

$R_3$ is —$C_{1-6}$alkyl optionally substituted with 1-3 groups selected from halo, —OH, or phenyl;

each of $R_4$ and $R_5$ is independently selected from —H, —OH, —$NH_2$, —$NHC(O)R_7$, —$NHC(O)OR_7$, —NHS(O)$_2R_7$, —$C(O)R_7$, —$C(O)OR_7$, —$CH_2OR_7$, —$CH_2N(R_7)_2$, —$C_{1-6}$alkyl, each of which is optionally substituted with 1-3 groups selected from halo or —OH, or $R_4$ and $R_5$ together form oxo or =N—O—$R_7$;

Ring A is a 5-8 membered saturated, partially unsaturated, or fully unsaturated ring having 0-3 heteroatoms independently selected from N, O, or S, wherein ring A is optionally substituted with 1-3 of $R_6$;

each $R_6$ is independently halo, —H, —CN, —NO$_2$, —$C_{1-6}$ alkyl, aryl, 5-10 membered heteroaryl, —S(O)$_2$R$_7$, or —C(O)R$_7$, each of which is optionally substituted with 1-3 groups selected from halo or —OH;

each $R_7$ is independently —H, —$C_{1-6}$ alkyl, —$C_{3-8}$ cycloalkyl, or phenyl; and n is 0 or 1.

In some methods, the compound of Formula I is selected from the compounds described in Table 1.

In some methods, the compound of Formula I is provided as a salt (e.g., an HCl salt or a metal salt). For example, the compound of Formula I is provided as a sodium salt, a potassium salt, or a hydrogen chloride (HCl) salt.

In some methods, the patient is administered a pharmaceutical composition comprising a compound of Formula I, II, IIa, IIa-1, IIa-2, IIb, IIb-1, IIb-2, IIb-3, IIb-4, III, IIIa, IIIb-1, or IIIb-2, wherein said compound has a purity of about 70 e.e. % or greater (e.g., 80 e.e. % or greater, 90 e.e. % or greater, 95 e.e. % or greater, or 99 e.e. % or greater).

Some methods further comprise the administration of a beta-adrenergic agonist to the patient. For example, the beta-adrenergic agonist comprises a beta-1-adrenergic agonist, a beta-2-adrenergic agonist, a beta-3-adrenergic agonist, or any combination thereof. In other examples, the beta-adrenergic agonist comprises noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or any combination thereof.

Some methods further comprise the administration of a phosphodiesterase inhibitor to the patient. Examples of phosphodiesterase inhibitors comprise non-selective inhibitors or selective inhibitors. For instance, the phosphodiesterase inhibitor comprises a non-selective inhibitor selected from caffeine (1,3,7-trimethylxanthine), theobromine (3,7-dimethyl-2,3,6,7-tetrahydro-1H-purine-2,6-dione), theophylline (1,3-dimethyl-7H-purine-2,6-dione), IBMX (3-isobutyl-1-methylxanthine), or any combination thereof. In other examples, the phosphodiesterase inhibitor comprises a selective inhibitor selected from Milrinone (2-methyl-6-oxo-1,6-dihydro-3,4'-bipyridine-5-carbonitrile), Cilostazol (6-[4-(1-cyclohexyl-1H-tetrazol-5-yl)butoxy]-3,4-dihydro-2(1 H)-quinolinone), Cilomilast (4-cyano-4-(3-cyclopentyloxy-4-methoxyphenyl)cyclohexane-1-carboxylic acid), Rolipram (4-(3-cyclopentyloxy-4-methoxy-phenyl)pyrrolidin-2-one), Roflumilast (3-(cyclopropylmethoxy)-N-(3,5-dichloropyridin-4-yl)-4-(difluoromethoxy)benzamide), or any combination thereof.

Some methods further comprise the administration of one or more additional pharmaceutical agents including, without limitation, a diuretic (e.g., hydrochlorothiazide, chlorthalidone, chlorthiazide, or combinations thereof), an ACE inhibitor (e.g., ramipril, captopril, enalapril, or combinations thereof), an angiotensin II receptor blocker (ARB) (e.g., candesartan, losartan, olmesartan, or combinations thereof), a rennin inhibitor, or any combination thereof. Other methods further comprise the administration of a compound that limits hypertension by alternate means including β-adrenergic receptor blockers and calcium channel blockers (e.g., amlodipine). In some methods, the patient is further administered one or more statins (e.g., atorvastatin, cerivastatin, fluvastatin, lovastatin, mevastatin, simvastatin, rosuvastatin, pravastatin, or any combination thereof).

Some methods further comprise administering to the patient a GLP analogue such as Exenatide (e.g., Exendin-4), Liraglutide, Taspoglutide, or any combination thereof.

Some methods further comprise administering to the patient a DPP4 inhibitor (e.g., sitagliptin, vildagliptin, saxagliptin, linagliptin, dutogliptin, gemigliptin, alogliptin, Berberine, or any combination thereof).

Some methods further comprise administering to the patient a phosphodiesterase inhibitor in combination with a beta-adrenergic agonist and at least one additional weight loss drug. Non-limiting examples of other weight loss drugs include appetite suppressants (e.g., Meridia, or the like), fat absorption inhibitors (e.g., Xenical, or the like), or compounds that augment sympathomimetic activity such as ephedrine or its various salts.

In those methods that include the administration of one or more additional drugs (e.g., phosphodiesterase inhibitors and/or beta-adrenergic agonists), the one or more additional drugs may be administered concurrently with the compound or composition of the present invention or sequentially.

Another aspect of the present invention provides a method of treating or reducing the severity of hypertension or dyslipidemia in a patient comprising administering to the patient in need thereof a compound of Formula I:

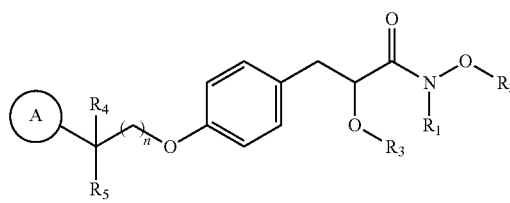

or a pharmaceutically acceptable salt thereof, wherein

Each of $R_1$ and $R_2$ is independently selected from —H, —$C_{1-6}$ alkyl, aryl, 5-10 membered heteroaryl, —$C_{3-6}$cycloaliphatic, 3-8 membered heterocycloaliphatic, —CH$_2$-aryl, —CH$_2$-5-10 membered heteroaryl, —CH$_2$—$C_{3-6}$ cycloaliphatic, —CH$_2$-3-8 membered heterocycloaliphatic, each of which is optionally substituted with 1-3 groups selected from halo, —OH, or phenyl, or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;

$R_3$ is —$C_{1-6}$ alkyl optionally substituted with 1-3 groups selected from halo, —OH, or phenyl;

each of $R_4$ and $R_5$ is independently selected from —H, —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —$C_{1-6}$alkyl, each of which is optionally substituted with 1-3 groups selected from halo or —OH, or $R_4$ and $R_5$ together form oxo or =N—O—$R_7$;

Ring A is a 5-8 membered saturated, partially unsaturated, or fully unsaturated ring having 0-3 heteroatoms independently selected from N, O, or S, wherein ring A is optionally substituted with 1-3 of $R_6$;

each $R_6$ is independently halo, —H, —CN, —$OR_7$, —$NO_2$, —$C_{1-6}$alkyl, aryl, 5-10 membered heteroaryl, —$S(O)_2R_7$, or —$C(O)R_7$, each of which is optionally substituted with 1-3 groups selected from halo or —OH;

each $R_7$ is independently —H, —$C_{1-6}$alkyl, —$C_{3-8}$ cycloalkyl, or phenyl; and n is 0 or 1.

In some methods, the compound of Formula I is selected from the compounds described in Table 1.

In some methods, the compound of Formula I is provided as a salt (e.g., an HCl salt or a metal salt). For example, the compound of Formula I is provided as a sodium salt, a potassium salt, or a hydrogen chloride salt.

In some methods, the patient is administered a pharmaceutical composition comprising a compound of Formula I, II, IIa, IIa-1, IIa-2, IIb, IIb-1, IIb-2, IIb-3, IIb-4, III, IIIa, IIIb-1, or IIIb-2, wherein said compound has a purity of about 70 e.e. % or greater (e.g., 80 e.e. % or greater, 90 e.e. % or greater, 95 e.e. % or greater, or 99 e.e. % or greater).

Some methods further comprise the administration of a beta-adrenergic agonist to the patient. For example, the beta-adrenergic agonist comprises a beta-1-adrenergic agonist, a beta-2-adrenergic agonist, a beta-3-adrenergic agonist, or any combination thereof. In other examples, the beta-adrenergic agonist comprises noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or any combination thereof.

Some methods further comprise the administration of a phosphodiesterase inhibitor to the patient. Examples of phosphodiesterase inhibitors comprise non-selective inhibitors or selective inhibitors. For instance, the phosphodiesterase inhibitor comprises a non-selective inhibitor selected from caffeine (1,3,7-trimethylxanthine), theobromine (3,7-dimethyl-2,3,6,7-tetrahydro-1H-purine-2,6-dione), theophylline (1,3-dimethyl-7H-purine-2,6-dione), IBMX (3-isobutyl-1-methylxanthine), or any combination thereof. In other examples, the phosphodiesterase inhibitor comprises a selective inhibitor selected from Milrinone (2-methyl-6-oxo-1,6-dihydro-3,4'-bipyridine-5-carbonitrile), Cilostazol (6-[4-(1-cyclohexyl-1H-tetrazol-5-yl)butoxy]-3,4-dihydro-2(1 H)-quinolinone), Cilomilast (4-cyano-4-(3-cyclopentyloxy-4-methoxyphenyl)cyclohexane-1-carboxylic acid), Rolipram (4-(3-cyclopentyloxy-4-methoxy-phenyl)pyrrolidin-2-one), Roflumilast (3-(cyclopropylmethoxy)-N-(3,5-dichloropyridin-4-yl)-4-(difluoromethoxy)benzamide), or any combination thereof.

Some methods further comprise the administration of one or more additional pharmaceutical agents including, without limitation, a diuretic (e.g., hydrochlorothiazide, chlorothalidone, chlorothiazide, or combinations thereof), an ACE inhibitor (e.g., ramipril, captopril, enalapril, or combinations thereof), an angiotensin II receptor blocker (ARB) (e.g., candesartan, losartan, olmesartan, or combinations thereof), a rennin inhibitor, or any combination thereof. Other methods further comprise the administration of a compound that limits hypertension by alternate means including β-adrenergic receptor blockers and calcium channel blockers (e.g., amlodipine). In some methods, the patient is further administered one or more statins (e.g., atorvastatin, cerivastatin, fluvastatin, lovastatin, mevastatin, simvastatin, rosuvastatin, pravastatin, or any combination thereof).

Some methods further comprise administering to the patient a GLP analogue such as Exenatide (e.g., Exendin-4), Liraglutide, Taspoglutide, or any combination thereof.

Some methods further comprise administering to the patient a DPP4 inhibitor (e.g., sitagliptin, vildagliptin, saxagliptin, linagliptin, dutogliptin, gemigliptin, alogliptin, Berberine, or any combination thereof).

Some methods further comprise administering to the patient a phosphodiesterase inhibitor in combination with a beta-adrenergic agonist and at least one additional weight loss drug. Non-limiting examples of other weight loss drugs include appetite suppressants (e.g., Meridia, or the like), fat absorption inhibitors (e.g., Xenical, or the like), or compounds that augment sympathomimetic activity such as ephedrine or its various salts.

In those methods that include the administration of one or more additional drugs (e.g., phosphodiesterase inhibitors and/or beta-adrenergic agonists), the one or more additional drugs may be administered concurrently with the compound of the present invention or sequentially.

Another aspect of the present invention provides a method of treating, reducing the severity of, or delaying the onset of obesity (e.g., central obesity) in a patient comprising administering to the patient in need thereof a compound of Formula I:

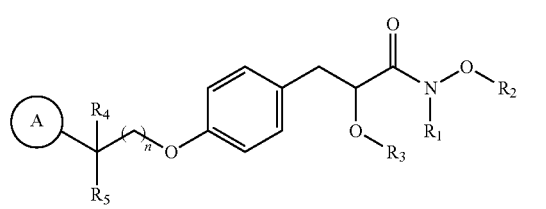

or a pharmaceutically acceptable salt thereof, wherein

Each of $R_1$ and $R_2$ is independently selected from —H, —$C_{1-6}$alkyl, aryl, 5-10 membered heteroaryl, —$C_{3-6}$cycloaliphatic, 3-8 membered heterocycloaliphatic, —$CH_2$-aryl, —$CH_2$-5-10 membered heteroaryl, —$CH_2$—$C_{3-6}$cycloaliphatic, —$CH_2$-3-8 membered heterocycloaliphatic, each of which is optionally substituted with 1-3 groups selected from halo, —OH, or phenyl, or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;

$R_3$ is —$C_{1-6}$alkyl optionally substituted with 1-3 groups selected from halo, —OH, or phenyl;

each of $R_4$ and $R_5$ is independently selected from —H, —OH, —$NH_2$, —$NHC(O)R_7$, —$NHC(O)OR_7$, —$NHS(O)_2R_7$, —$C(O)R_7$, —$C(O)OR_7$, —$CH_2OR_7$, —$CH_2N(R_7)_2$, —$C_{1-6}$alkyl, each of which is optionally substituted with 1-3 groups selected from halo or —OH, or $R_4$ and $R_5$ together form oxo or =N—O—$R_7$;

Ring A is a 5-8 membered saturated, partially unsaturated, or fully unsaturated ring having 0-3 heteroatoms independently selected from N, O, or S, wherein ring A is optionally substituted with 1-3 of $R_6$;

each $R_6$ is independently halo, —H, —CN, —OR$_7$, —NO$_2$, —C$_{1-6}$alkyl, aryl, 5-10 membered heteroaryl, —S(O)$_2$R$_7$, or —C(O)R$_7$, each of which is optionally substituted with 1-3 groups selected from halo or —OH;

each $R_7$ is independently —H, —C$_{1-6}$alkyl, —C$_{3-8}$cycloalkyl, or phenyl; and n is 0 or 1.

In some methods, the compound of Formula I is selected from the compounds described in Table 1.

In some methods, the compound of Formula I is provided as a salt (e.g., an HCl salt or a metal salt). For example, the compound of Formula I is provided as a sodium salt, a potassium salt, or a hydrogen chloride salt.

In some methods, the patient is administered a pharmaceutical composition comprising a compound of Formula I, II, IIa, IIa-1, IIa-2, IIb, IIb-1, IIb-2, IIb-3, IIb-4, III, IIIa, or IIIb-2, wherein said compound has a purity of about 70 e.e. % or greater (e.g., 80 e.e. % or greater, 90 e.e. % or greater, 95 e.e. % or greater, or 99 e.e. % or greater).

Some methods further comprise the administration of a beta-adrenergic agonist to the patient. For example, the beta-adrenergic agonist comprises a beta-1-adrenergic agonist, a beta-2-adrenergic agonist, a beta-3-adrenergic agonist, or any combination thereof. In other examples, the beta-adrenergic agonist comprises noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or any combination thereof.

Some methods further comprise the administration of a phosphodiesterase inhibitor to the patient. Examples of phosphodiesterase inhibitors comprise non-selective inhibitors or selective inhibitors. For instance, the phosphodiesterase inhibitor comprises a non-selective inhibitor selected from caffeine (1,3,7-trimethylxanthine), theobromine (3,7-dimethyl-2,3,6,7-tetrahydro-1H-purine-2,6-dione), theophylline (1,3-dimethyl-7H-purine-2,6-dione), IBMX (3-isobutyl-1-methylxanthine), or any combination thereof. In other examples, the phosphodiesterase inhibitor comprises a selective inhibitor selected from Milrinone (2-methyl-6-oxo-1,6-dihydro-3,4'-bipyridine-5-carbonitrile), Cilostazol (6-[4-(1-cyclohexyl-1H-tetrazol-5-yl)butoxy]-3,4-dihydro-2(1 H)-quinolinone), Cilomilast (4-cyano-4-(3-cyclopentyloxy-4-methoxyphenyl)cyclohexane-1-carboxylic acid), Rolipram (4-(3-cyclopentyloxy-4-methoxy-phenyl)pyrrolidin-2-one), Roflumilast (3-(cyclopropylmethoxy)-N-(3,5-dichloropyridin-4-yl)-4-(difluoromethoxy)benzamide), or any combination thereof.

Some methods further comprise the administration of one or more additional pharmaceutical agents including, without limitation, a diuretic (e.g., hydrochlorothiazide, chlorthalidone, chlorothiazide, or combinations thereof), an ACE inhibitor (e.g., ramipril, captopril, enalapril, or combinations thereof), an angiotensin II receptor blocker (ARB) (e.g., candesartan, losartan, olmesartan, or combinations thereof), a rennin inhibitor, or any combination thereof. Other methods further comprise the administration of a compound that limits hypertension by alternate means including β-adrenergic receptor blockers and calcium channel blockers (e.g., amlodipine). In some methods, the patient is further administered one or more statins (e.g., atorvastatin, cerivastatin, fluvastatin, lovastatin, mevastatin, simvastatin, rosuvastatin, pravastatin, or any combination thereof).

Some methods further comprise administering to the patient a GLP analogue such as Exenatide (e.g., Exendin-4), Liraglutide, Taspoglutide, or any combination thereof.

Some methods further comprise administering to the patient a DPP4 inhibitor (e.g., sitagliptin, vildagliptin, saxagliptin, linagliptin, dutogliptin, gemigliptin, alogliptin, Berberine, or any combination thereof).

Some methods further comprise administering to the patient a phosphodiesterase inhibitor in combination with a beta-adrenergic agonist and at least one additional weight loss drug. Non-limiting examples of other weight loss drugs include appetite suppressants (e.g., Meridia, or the like), fat absorption inhibitors (e.g., Xenical, or the like), or compounds that augment sympathomimetic activity such as ephedrine or its various salts.

In those methods that include the administration of one or more additional drugs (e.g., phosphodiesterase inhibitors and/or beta-adrenergic agonists), the one or more additional drugs may be administered concurrently with the compound of the present invention or sequentially.

Some embodiments further comprise restricting the diet of the patient.

Some embodiments further comprise increasing the duration or intensity of the patient's physical activity.

Another aspect of the present invention provides a method of treating, reducing the severity of, or delaying the onset of a neurodegenerative disorder (e.g., Alzheimer's disease, Parkinson's disease, or Huntingon's disease) in a patient comprising administering to the patient in need thereof a compound of Formula I:

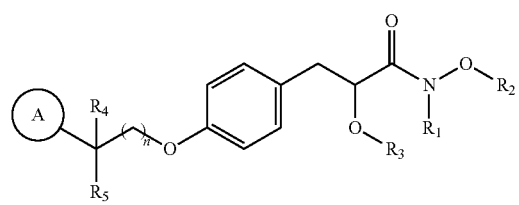

or a pharmaceutically acceptable salt thereof, wherein

Each of $R_1$ and $R_2$ is independently selected from —H, —C$_{1-6}$alkyl, aryl, 5-10 membered heteroaryl, —C$_{3-6}$cycloaliphatic, 3-8 membered heterocycloaliphatic, —CH$_2$-aryl, —CH$_2$-5-10 membered heteroaryl, —CH$_2$—C$_{3-6}$ cycloaliphatic, —CH$_2$-3-8 membered heterocycloaliphatic, each of which is optionally substituted with 1-3 groups selected from halo, —OH, or phenyl, or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;

$R_3$ is —C$_{1-6}$ alkyl optionally substituted with 1-3 groups selected from halo, —OH, or phenyl;

each of $R_4$ and $R_5$ is independently selected from —H, —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$alkyl, each of which is optionally substituted with 1-3 groups selected from halo or —OH, or $R_4$ and $R_5$ together form oxo or =N—O—R$_7$;

Ring A is a 5-8 membered saturated, partially unsaturated, or fully unsaturated ring having 0-3 heteroatoms independently selected from N, O, or S, wherein ring A is optionally substituted with 1-3 of R$_6$;

each $R_6$ is independently halo, —H, —CN, —OR$_7$, —NO$_2$, —C$_{1-6}$ alkyl, aryl, 5-10 membered heteroaryl, —S(O)$_2$R$_7$, or —C(O)R$_7$, each of which is optionally substituted with 1-3 groups selected from halo or —OH;

each $R_7$ is independently —H, —C$_{1-6}$alkyl, —C$_{3-8}$cycloalkyl, or phenyl; and n is 0 or 1.

Reducing the symptoms or treating Alzheimer's disease may be demonstrated when a patient shows an improvement from baseline in one or more cognitive tests (e.g., ADAS cognitive testing, Clinician Interview Based Impression of Change, or Severe Impairment Battery). Additionally, reducing the symptoms or treating Alzheimer's disease may be demonstrated when a patient shows a reduction from baseline in one or more biomarkers associated with Alzheimer's disease (e.g., CSF Aβ or CSF AT).

Reducing the symptoms or treating Parkinson's disease may be demonstrated when a patient shows an improvement from baseline in one or more testes including the Unified PD Rating Scale. Delaying the onset of Parkinson's disease may be demonstrated when a patient shows an improved "time to emergence" or time to dopaminergic therapy when compared with an untreated patient population or a patient population treated with an alternative therapy.

V. Uses, Formulations And Administrations

As discussed above, the present invention provides compounds that are useful as treatments for treating metabolic inflammation mediated diseases such as diabetes, obesity, hypertension, dyslipidemia, or any combination thereof.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition; according to the judgment of the formulator.

According to the invention an "effective amount" of the compound or pharmaceutically acceptable composition is that amount effective for treating, preventing, or lessening the severity of metabolic diseases (e.g., obesity, diabetes, hypertension, dyslipidemia, neurodegenerative diseases (e.g., Alzheimer's disease, dementia, or the like), or any combination thereof).

The pharmaceutical compositions, according to the method of the present invention, may be administered using any amount and any route of administration effective for treating or lessening the severity of obesity and/or obesity related diseases.

The exact amount required will vary from subject to subject, depending on the species, age, and general condition of the subject, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, and more specifically a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the compounds of the invention may be administered orally or parenterally at dosage levels of between 10 mg/kg and about 120 mg/kg.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as treatments for metabolic diseases.

The activity, or more importantly, reduced PPARγ activity of a compound utilized in this invention as a treatment of obesity and/or reducing bodyweight may be assayed according to methods described generally in the art and in the examples provided herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121, each of which is incorporated by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to treating metabolic diseases in a biological sample or a patient (e.g., in vitro or in vivo), which method comprises administering to the patient, or contacting said biological sample with a pharmaceutical composition comprising a compound of Formula I, II, IIa, IIa-1, IIa-2, IIb, IIb-1, IIb-2, IIb-3, IIb-4, III, IIIa, IIIb-1, or IIIb-2. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

VI. Generic Synthetic Schemes

The compounds of Formula I may be readily synthesized from commercially available or known starting materials. Exemplary synthetic routes to produce compounds of Formula I are provided in the schemes below.

Scheme 1:

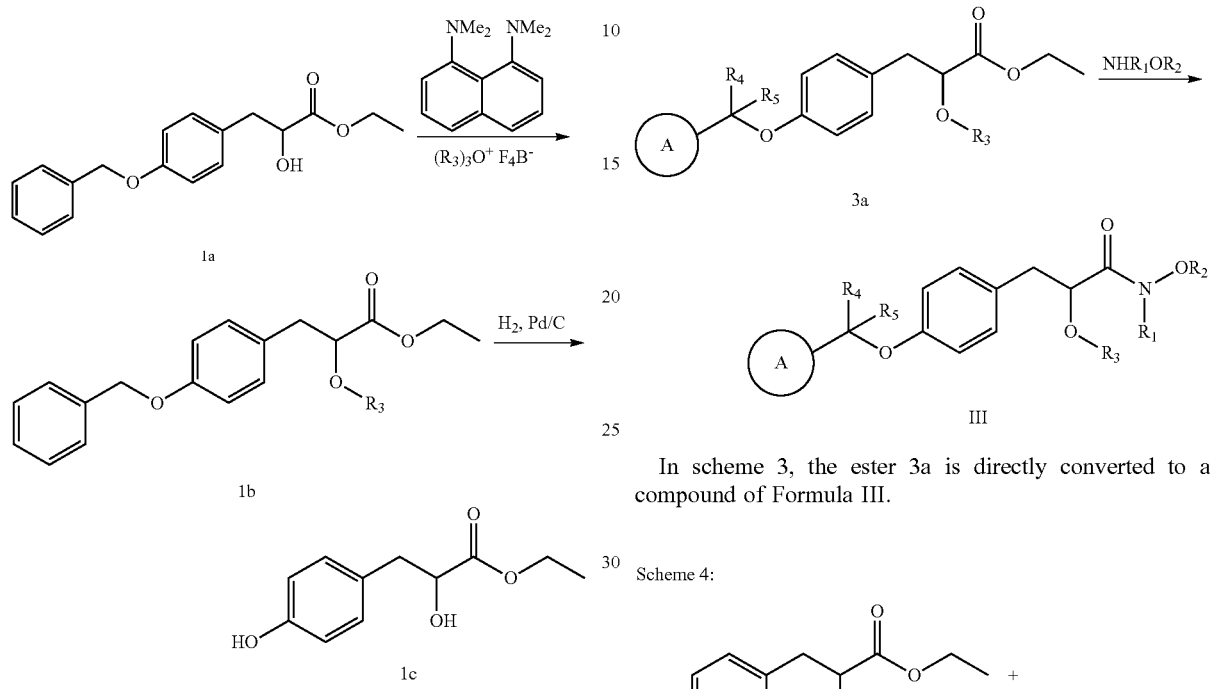

1a

1b

1c

In scheme 1, starting material 1a undergoes alkylation to generate intermediate 1b, which undergoes hydrogenation to generate intermediate 1c.

Scheme 2:

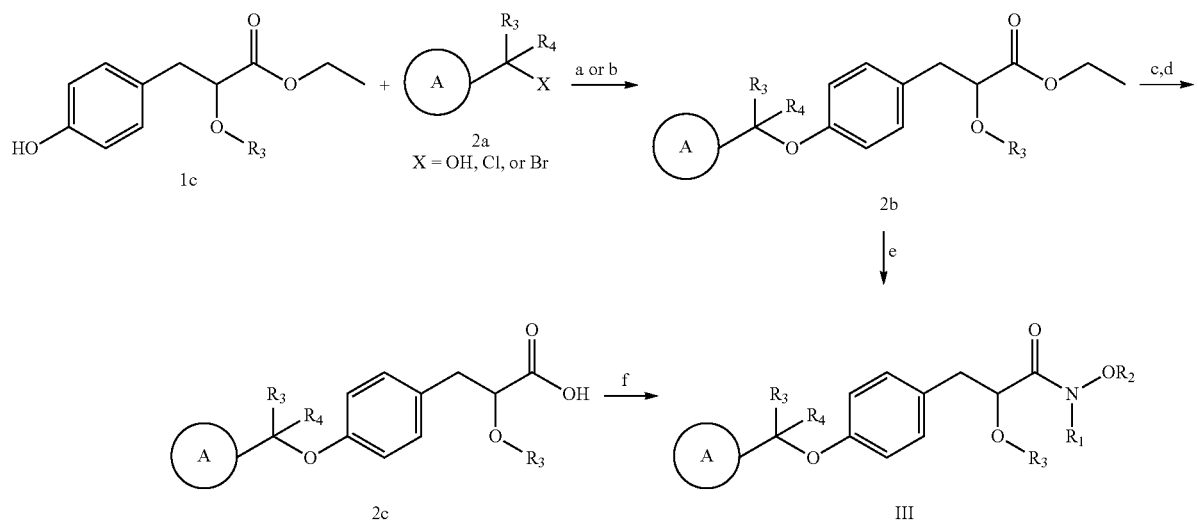

1c

2a
X = OH, Cl, or Br

2b

2c

III a) (X = OH) R$_1$P, RO$_2$CN═NCO$_2$R
b) (C = Cl or Br) K$_2$CO$_3$, acetone or Cs$_2$CO$_3$, DMF
c) aq. NaOH or aq. KOH or aq. LiOH
d) aq. HCl
e) R$_1$NHOR$_2$, i-PrMgCl
f) R$_1$HNOR$_2$ or H$_2$NOR$_2$ or R$_1$NHOH, HATU, Et$_3$N In Scheme 2, intermediates 1c and 2a are coupled under basic conditions, to generate intermediate 2b. Intermediate 2b is hydrolyzed to generate the carboxylic acid 2c, and carboxylic acid 2c undergoes amidation to generate the compound of Formula III. Intermediate 2b can also undergo amidation to generate the compound of Formula III.

Scheme 3:

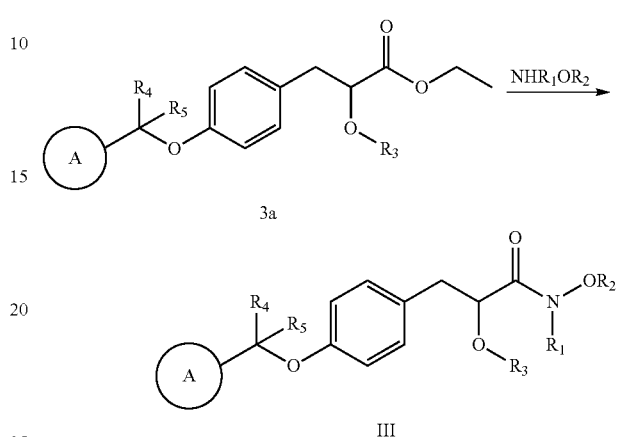

3a

III

In scheme 3, the ester 3a is directly converted to a compound of Formula III.

Scheme 4:

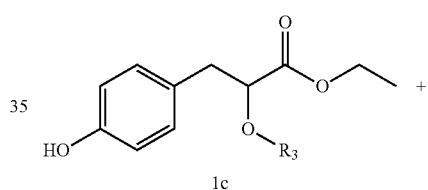

1c

51
-continued

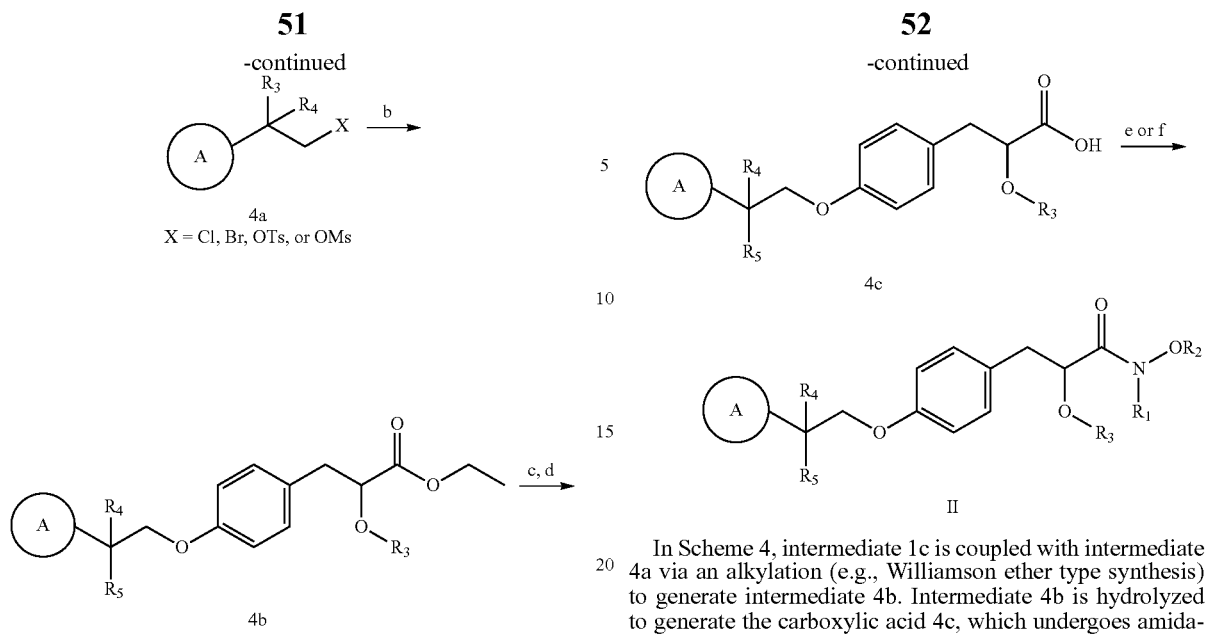

4a
X = Cl, Br, OTs, or OMs

4b

52
-continued

4c

II

In Scheme 4, intermediate 1c is coupled with intermediate 4a via an alkylation (e.g., Williamson ether type synthesis) to generate intermediate 4b. Intermediate 4b is hydrolyzed to generate the carboxylic acid 4c, which undergoes amidation to generate the compound of Formula II.

Scheme 5:

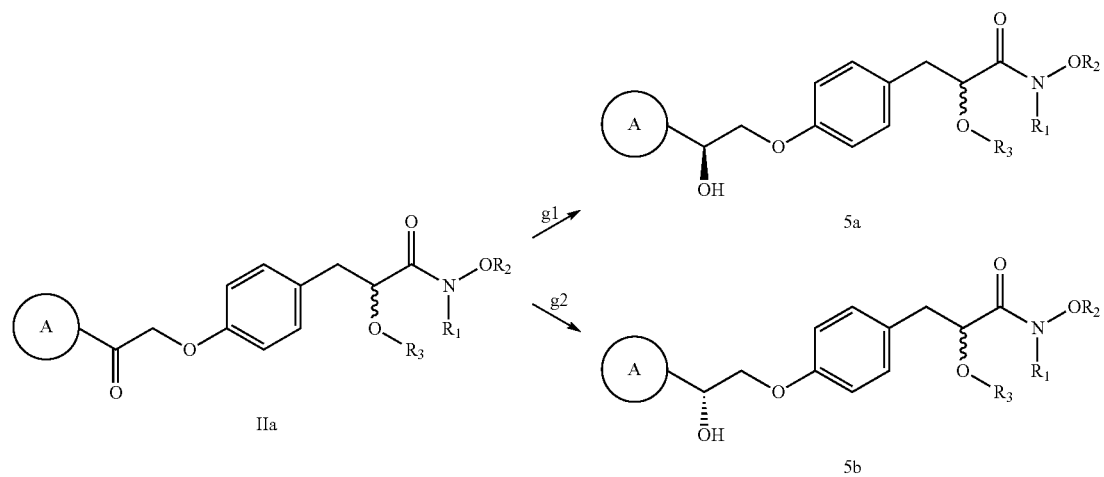

IIa

5a

5b g1) Noyori reduction with (1R,2R)-(-)-N-p-tosyl-1,2-diphenylethylenediamine ligand
g2) Noyori reduction with (1S,2S)-(+)-N-p-tosyl-1,2-diphenylethylenediamine ligand In scheme 5, the compound of Formula IIa undergoes a Noyori reduction to form either the compound of Formula 5a or the compound of Formula 5b.

Scheme 6:
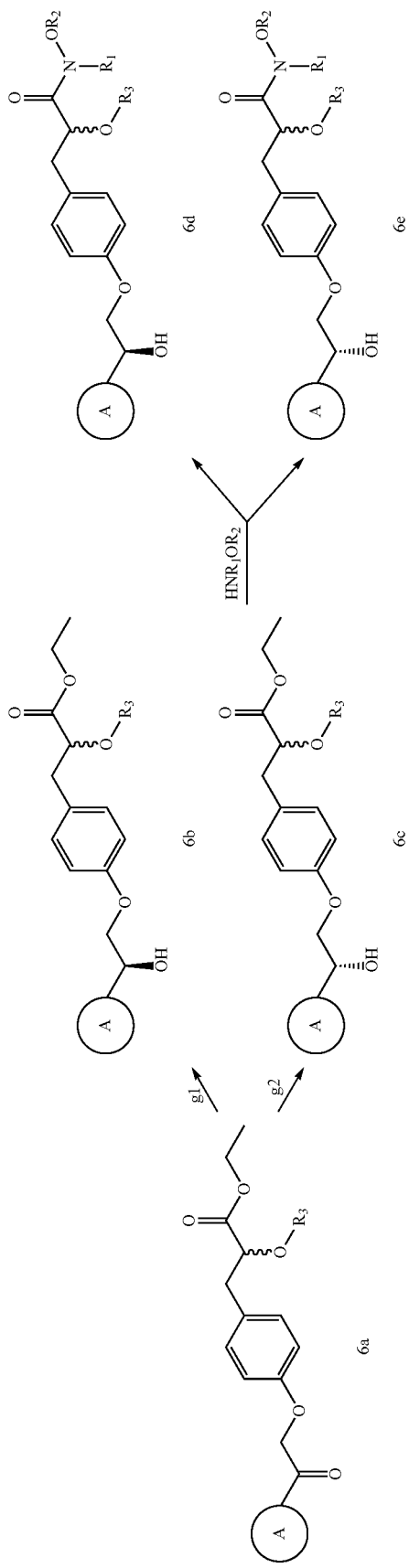
g1) Noyori reduction with (1R,2R)-(-)-N-p-tosyl-1,2-diphenylethylenediamine ligand
g2) Noyori reduction with (1S,2S)-(+)-N-p-tosyl-1,2-diphenylethylenediamine ligand In scheme 6, ester 6a undergoes Noyori reduction to generate intermediates 6b or 6c. Intermediates 6b or 6c undergo amidation to generate the compounds of Formula 6d or 6e, respectively.

VII. EXAMPLES

General Method for HPLC: Agilent 1100 HPLC. Agilent XDB C18 50×4.6 mm 1.8 micron column. Solvent A Water (0.1% TFA); Solvent B Acetonitrile (0.1% TFA), Gradient 5 min 95% A to 95% B; 1 min hold; 1 min recycle; then hold 0.5 min; UV detection.

Example 1

Ethyl (2S)-2-ethoxy-3-(4-hydroxyphenyl)propanoate

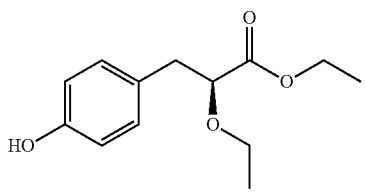 [SMILES: CCOC(=O)[C@H](Cc1ccc(O)cc1)OCC]

Ethyl (2S)-3-[4-(benzyloxy)phenyl]-2-hydroxypropanoate (8.00 g, 26.6 mmol) (prepared as per: Aikins, J. A.; Haurez, M.; Rizzo, J. R.; Van Hoeck, J-P.; Brione, W.; Kestemont, J-P.; Stevens, C.; Lemair, X.; Stephenson, G. A.; Marlot, E.; Forst, M.; Houpis, I. N. *J. Org. Chem.* 2005, 70, 4695-4705) was dissolved in methylene chloride (120 mL) and N,N,N',N'-tetramethyl-1,8 naphthalenediamine (7.14 g, 33.3 mmol) was added followed by triethyloxonium tetrafluoroborate (6.32 g, 33.3 mmol). The reaction mixture was stirred at RT and monitored by HPLC until the starting material was consumed. The reaction mixture was filtered through a pad of silica gel and filter cake was washed with EtOAc (250 mL). The combined filtrates were concentrated in vacuo to give an oil (2S)-3-[4-(benzyloxy)phenyl]-2-ethoxypropanoate (6.45 g), which was used without additional purification.

Ethyl (2S)-3-[4-(benzyloxy)phenyl]-2-ethoxypropanoate (6.45 g, 19.6 mmol) was dissolved in ethanol (300 mL). 10% Palladium on carbon (10% Palladium:carbon black, 4.50 g, 4.23 mmol) was added and the reaction vessel was placed under a balloon atmosphere of hydrogen. The mixture was stirred at RT and monitored by HPLC for consumption of SM. Once complete, the reaction atmosphere was exchanged for nitrogen and stirred for 15 mins. The insolubles were removed via filtration through Celite. The filter cake was washed with EtOAc (300 mL). The combined filtrate was concentrated in vacuo to give a ethyl (2S)-2-ethoxy-3-(4-hydroxyphenyl)propanoate (4.32 g as an oil which was utilized without further purification.

$^1$H NMR (400 MHz, CHLOROFORM-d) δ ppm 1.18 (t, J=7.05 Hz, 3 H), 1.24 (t, J=7.15 Hz, 3 H), 2.96 (d, J=6.63 Hz, 2 H), 3.39 (m, 1 H), 3.62 (m 1 H), 4.02 (t, J=6.63 Hz, 1 H), 4.18 (q, J=7.05 Hz, 2 H), 6.33 (s, 1 H), 6.75 (d, J=8.50 Hz, 2 H), 7.08 (d, J=8.50 Hz, 2 H)

Example 2

Ethyl (2R)-2-ethoxy-3-(4-hydroxyphenyl)propanoate

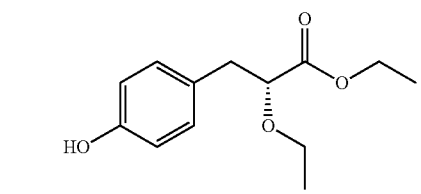 [SMILES: CCOC(=O)[C@@H](Cc1ccc(O)cc1)OCC]

Ethyl (2R)-3-[4-(benzyloxy)phenyl]-2-hydroxypropanoate (8.00 g, 49.8 mmol) (prepared as per: Parmenon, C.; Guillard, J.; Caignard, D-H.; Hennuyer, N.; Staels, B.; Audinot-Bouchez, V.; Boutin, J-A.; Dacquet, C.; Ktorza, A.; Viaud-Massuard, M-C. *Bioorg. Med. Chem. Lett.* 2008, 18, 1617-1622) was dissolved in methylene chloride (250 mL) and N,N,N',N'-tetramethyl-1,8 naphthalenediamine (13.34 g, 62.25 mmol) was added followed by triethyloxonium tetrafluoroborate (11.81 g, 62.25 mmol). The reaction mixture was stirred at RT and monitored by HPLC till the starting material was consumed. The reaction mixture was filtered through a pad of silica gel and filter cake was washed with EtOAc (500 mL). The combined filtrates were concentrated in vacuo to give an oil (2R)-3-[4-(benzyloxy)phenyl]-2-ethoxypropanoate (12.27 g), which was used without additional purification.

A stirring mixture of ethyl (2R)-3-[4-(benzyloxy)phenyl]-2-ethoxypropanoate (9.82 g, 29.9 mmol) and 10% palladium on carbon (4.00 g, 37.6 mmol) in EtOH (150 ml) was left to stir under hydrogen (balloon) overnight. At which point HPLC/MS shows that the reaction is complete. The mixture was filtered through a pad of celite, the filter cake was rinsed with EtOAc (350 mL) and the combined filtrates were evaporated in vacuo to give a light tan oil (6.55 g), which was utilized without further purification.

$^1$H NMR (400 MHz, CHLOROFORM-d) δ ppm 1.20 (t, J=7.00 Hz, 3 H), 1.22 (t, J=7.13 Hz, 3 H), 2.96 (d, J=6.63 Hz, 2 H), 3.39 (m, 1 H), 3.62 (m 1 H), 4.02 (t, J=6.63 Hz, 1 H), 4.18 (q, J=7.00 Hz, 2 H), 6.32 (s, 1 H), 6.76 (d, J=8.50 Hz, 2 H), 7.06 (d, J=8.50 Hz, 2 H)

Example 3

(2S)-2-ethoxy-N-hydroxy-3-{4-[(3-iodobenzyl)oxy]phenyl}propanamide (Compound No. 7)

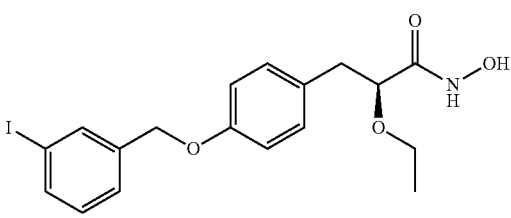 [SMILES: CCO[C@@H](Cc1ccc(OCc2cccc(I)c2)cc1)C(=O)NO]

To ethyl (2S)-2-ethoxy-3-(4-hydroxyphenyl)propanoate (395 mg, 1.66 mmol), dissolved in tetrahydrofuran (8.0 mL), was added (3-iodophenyl)methanol (504 mg, 2.16 mmol). Then tributylphosphine (0.620 mL, 2.49 mmol) and diisopropyl azodicarboxylate (0.490 mL, 2.49 mmol) were added sequentially. The mixture was allowed to stir at RT for 6 hours. The reaction mixture was adsorbed onto silica gel and chromatographed using a CombiFlash Rf instrument (12 g Gold silica gel column, eluting with 0-50% EtOAc/hex, collecting @ 254 nm). Fractions containing product were combined and evaporated in vacuo to give ethyl (2S)-2-ethoxy-3-{4-[(3-iodobenzyl)oxy]phenyl}propanoate (422 mg) as a colorless oil which was used without further purification.

To ethyl (2S)-2-ethoxy-3-{4-[(3-iodobenzyl)oxy] phenyl}propanoate (422 mg, 0.928 mmol) hydroxylamine hydrochloride (0.822 g, 11.8 mmol) was suspended in methanol (5 mL) and the reaction mixture was cooled in an ice/water bath. Potassium hydroxide (0.995 g, 17.7 mmol) in methanol (2.35 mL, 58.1 mmol) was added over 5 minutes to this cooled reaction mixture. Immediately, a thick precipitate formed. The reaction mixture was stirred in the ice/water bath for 30 min. The precipitate was removed via filtration and the filtrate was used as a hydroxylamine solution in MeOH. (2S)-2-Ethoxy-3-{4-[(3-iodobenzyl)oxy] phenyl}propanoic acid (90 mg, 0.2 mmol) was dissolved in methanol (1 mL, 30 mmol) and cooled in an ice/water bath. 4 mL of hydroxylamine in MeOH was added and the reaction was left to stir at RT for 6 hours. The mixture was concentrated in vacuo and the crude residue was dissolved in MeOH and 6M aq. HCl was added until the pH of the mixture was adjusted to pH=1. Evaporated in vacuo and the crude residue was purified on CombiFlash Rf instrument using 15.5 g C18Aq Gold column (0.1% TFA in MeCN: 0.1% TFA in Water gradient). Fractions collected on 214 nM to give (2S)-2-ethoxy-N-hydroxy-3-{4-[(3-iodobenzyl)oxy] phenyl}propanamide (Compound No. 7) (30 mg) as a white solid.

$^1$H NMR (300 MHz, MeOD) δ ppm 1.11 (t, J=7.03 Hz, 3 H), 1.69 (brs, 1 H), 2.87 (d, J=7.54 Hz, 1 H), 2.97 (m, 1 H), 3.03 (m, 1 H), 3.36 (m, 1 H), 3.51 (m, 1 H), 3.84 (dd, J=7.50, 5.08 Hz, 1 H), 5.02 (m, 2 H), 6.88 (m, 2 H), 7.08-7.21 (3 H), 7.43 (dd, J=7.64, 0.56 Hz, 1 H), 7.66 (d, J=8.29 Hz, 1 H), 7.80 (s, 1 H).

HPLC retention Time: 3.921 min
LCMS: 442.0 (M+H)+; 464.0 (M+Na)+

Example 4

Ethyl (2S)-2-ethoxy-3-[4-(pyridin-2-ylmethoxy) phenyl]propanoate

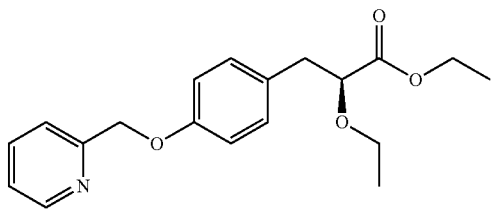 [SMILES: CCOC(=O)[C@H](Cc1ccc(OCc2ccccn2)cc1)OCC]

Ethyl (2S)-2-ethoxy-3-(4-hydroxyphenyl)propanoate (0.200 g, 0.839 mmol) was dissolved in N,N-dimethylformamide (4 mL, 50 mmol). Cesium carbonate (0.615 g, 1.89 mmol) was added followed by 2-(bromomethyl)pyridine hydrobromide (0.234 g, 0.923 mmol). The reaction mixture was stirred at RT and monitored by HPLC. Once the reaction is interpreted to be complete, it was diluted with water (25 mL) and extracted with E60 (3×25 mL). The combined organics were washed with brine (50 mL), dried (Na$_2$SO$_4$), and concentrated in vacuo. The crude product was purified by flash silica gel chromatography on the CombiFlash RF instrument (12 g Gold Silica gel column, acetone:hexane gradient, 220 nM collection wavelength). Fractions identified using HPLC, collected and concentrated in vacuo to give ethyl (2S)-2-ethoxy-3-[4-(pyridin-2-ylmethoxy)phenyl]propanoate (0.085 g) as a clear, colorless oil.

$^1$H NMR (300 MHz, CHLOROFORM-d) δ ppm 1.10-1.28 (6 H), 2.96 (d, J=6.6 Hz, 2 H), 3.34 (m, 1 H), 3.60 (m, 1 H), 3.98 (t, J=6.7 Hz, 1 H), 4.17 (q, J=7.1 Hz, 2 H), 5.20 (s, 2 H), 6.91 (d, J=8.7 Hz, 2 H), 7.17 (d, J=8.7 Hz, 2 H), 7.23 (m, 1 H), 7.53 (d, J=7.8 Hz, 1 H), 7.72 (td, J=7.7, 1.77 Hz, 1 H), 8.61 (dd, J=4.8, 0.8 Hz, 1 H).

HPLC retention Time: 3.050 min.
LCMS: 352.2 (M+Na)+, 330.2 (M−H)−

Example 5

(2S)-2-ethoxy-N-hydroxy-3-[4-(pyridin-2-ylmethoxy)phenyl]propanamide hydrogen chloride
(Compound No. 1)

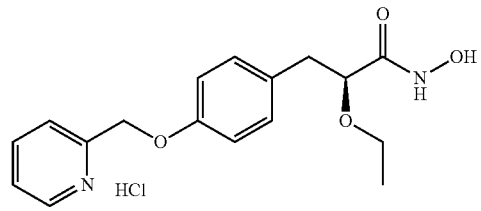 [SMILES: CCO[C@@H](Cc1ccc(OCc2ccccn2)cc1)C(=O)NO ; Cl]

Hydroxylamine hydrochloride (4.70 g, 67.6 mmol) was dissolved/suspended in methanol (24 mL) and the reaction mixture was cooled in an ice/water bath. Potassium hydroxide (5.71 g, 102 mmol) in methanol (14 mL, 340 mmol) was then added over 5 minutes. A thick precipitate is formed. The reaction mixture is stirred in the ice/water bath for 30 mins. The precipitate was then removed via filtration and the filtrate is used as a hydroxylamine solution in MeOH. Ethyl (2S)-2-ethoxy-3-[4-(pyridin-2-ylmethoxy)phenyl]propanoate (0.0994 g, 0.302 mmol) was dissolved in methanol (2 mL) and cooled in an ice/water bath and 4 mL of the aforementioned hydroxylamine in MeOH solution was added. The reaction mixture was stirred and monitored by HPLC. After 4 hours the reaction was interpreted to be complete and concentrated in vacuo. The crude material was diluted with water (50 mL) and the pH was adjusted to neutral (pH=7.0) with 1N aq. HCl. The solution was extracted with EtOAc (50 mL). The EtOAc layer is extracted with 1N aq. HCl (1×50 mL). Combined acidic aqueous layers were concentrated in vacuo and were purified on CombiFlash Rf instrument using 15.5 g C18Aq Gold column (0.1% TFA in MeCN:0.1% TFA in Water gradient). Fractions collected on 214 nM, identified by HPLC, pooled and concentrated in the presence of HCl (2×) to give (2S)-2-ethoxy-N-hydroxy-3-[4-(pyridin-2-ylmethoxy)phenyl]propanamide hydrogen chloride (Compound No. 1) (0.082 g) after lyophilization.

$^1$H NMR (300 MHz, METHANOL-d4) δ ppm 1.12 (t, J=7.03 Hz, 3 H), 2.89 (m, 1 H), 3.01 (m, 1 H), 3.34 (m, 1 H), 3.54 (dq, J=9.28, 7.03 Hz, 1 H), 3.87 (dd, J=7.64, 5.03 Hz, 1 H), 5.44 (s, 2 H), 7.03 (d, J=8.66 Hz, 2 H), 7.24 (d, J=8.66 Hz, 2 H), 7.92 (m, 1 H), 8.06 (d, J=8.01 Hz, 1 H), 8.49 (td, J=7.87, 1.40 Hz, 1 H), 8.80 (d, J=5.49 Hz, 1 H).

HPLC retention Time: 1.980 min

LCMS: 317.2 (M+H)+; 315.2 (M−H)−

Example 6

Ethyl (2S)-2-ethoxy-3-{4-[(4-methoxypyridin-2-yl)methoxy]phenyl}propanoate

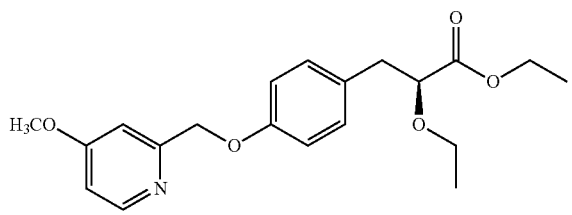 [SMILES: CCOC(=O)[C@H](Cc1ccc(OCc2cc(OC)ccn2)cc1)OCC]

In a round bottom flask, ethyl (2S)-2-ethoxy-3-(4-hydroxyphenyl)propanoate (0.1084 g, 0.4549 mmol) was dissolved in tetrahydrofuran (5.00 mL) and (4-methoxypyridin-2-yl)methanol (0.278 g, 2.00 mmol) was added. Tributylphosphine (390 uL, 1.6 mmol) and diisopropyl azodicarboxylate (310 uL, 1.6 mmol) were then added sequentially to the abovementioned solution. After 10 mins, the reaction is interpreted to be complete by HPLC-MS analysis. The reaction mixture is concentrated in vacuo and purified by CombiFlash Rf (C18aq Gold 30 g column, 0.1% TFA in MeCN: 0.1% TFA in water gradient, fractions collected on 214 nM). The appropriate fractions (HPLC-MS) were combined and reduced in volume to 10 mL of water. The aqueous solution is made basic with saturated sodium bicarbonate and extracted with ether (3×10 mL). The organic layer is dried over $Na_2SO_4$, filtered and concentrated in vacuo to give ethyl (2S)-2-ethoxy-3-{4-[(4-methoxypyridin-2-yl)methoxy]phenyl}propanoate (11.2 mg; 6.9%;) as an oil.

$^1$H NMR (300 MHz, CHLOROFORM-d) δ ppm 1.18 (t, J=7.0 Hz, 3 H), 1.23 (t, J=7.1 Hz, 3 H), 2.93-3.00 (m, 2 H), 3.36 (m, 1 H), 3.62 (m, 1 H), 3.91 (s, 3 H), 3.98 (t, J=6.7 Hz, 1 H), 4.17 (q, J=7.1 Hz, 2 H), 5.24 (s, 2 H), 6.83 (dd, J=5.8, 2.3 Hz, 1 H), 6.93 (d, J=8.8 Hz, 2 H), 7.14 (d, J=2.3 Hz, 1 H), 7.18 (d, J=8.8 Hz, 2 H), 8.43 (d, J=5.9 Hz, 1 H).

HPLC retention Time: 3.128 min

LCMS: 360.0 (M+H)+

Example 7

(2S)-2-ethoxy-3-{4-[(4-methoxypyridin-2-yl)methoxy]phenyl}propanoic acid hydrochloride

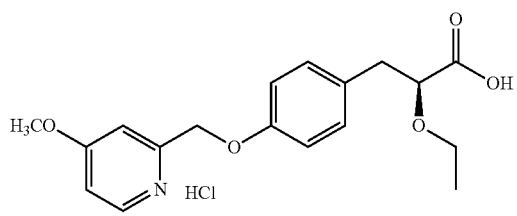 [SMILES: CCO[C@@H](Cc1ccc(OCc2cc(OC)ccn2)cc1)C(=O)O ; Cl]

In a round bottom flask, ethyl (2S)-2-ethoxy-3-{4-[(4-methoxypyridin-2-yl)methoxy]phenyl}propanoate (0.075 g, 0.21 mmol) was dissolved in acetonitrile (10 mL) and water (10 mL) was added. To this mixture 2M sodium hydroxide in water (2 mL, 4 mmol) was added and the reaction was stirred at RT for 4 hours. The mixture was concentrated in vacuo to remove volatile organics and the crude aqueous layer is acidified (pH=1 with 1N aq. HCl) and injected directly onto the CombiFlash Rf unit for purification (C18Aq Gold 30 g column, 0.1% TFA in MeCN:0.1% TFA in water gradient, collecting on 214 nM). Appropriate fractions were identified by HPLC-MS and were combined and concentrated in vacuo and salt swapped to HCl to give (2S)-2-ethoxy-3-{4-[(4-methoxypyridin-2-yl)methoxy]phenyl}propanoic acid hydrochloride (0.062 g; 81%) as a viscous oil.

$^1$H NMR (300 MHz, METHANOL-$d_4$) δ ppm 1.12 (t, J=7.0 Hz, 3 H), 2.91 (m, 1 H), 3.04 (m, 1 H), 3.35 (m, 1 H), 3.62 (m, 1 H), 4.03 (dd, J=8.0, 4.6 Hz, 1 H), 4.18 (s, 3 H), 5.42 (s, 2 H), 7.04 (d, J=8.6 Hz, 2 H), 7.26 (d, J=8.5 Hz, 2 H), 7.51 (dd, J=7.0, 2.5 Hz, 1 H), 7.65 (d, J=2.3 Hz, 1 H), 8.62 (d, J=7.0 Hz, 1 H).

HPLC retention Time: 2.402 min

LCMS: 332.3 (M+H)+

Example 8

(2S)-2-ethoxy-N-hydroxy-3-{4-[(4-methoxypyridin-2-yl)methoxy]phenyl}propanamide hydrochloride (Compound No. 3)

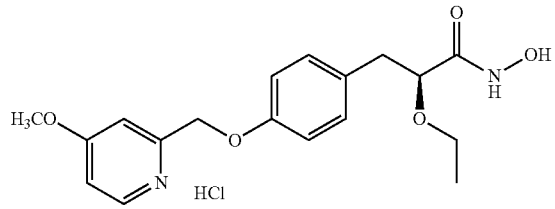 [SMILES: CCO[C@@H](Cc1ccc(OCc2cc(OC)ccn2)cc1)C(=O)NO ; Cl]

Hydroxylamine hydrochloride (1.17 g, 16.9 mmol) was dissolved/suspended in Methanol (6.0 mL). The reaction mixture was cooled in an ice/water bath. Potassium hydroxide (1.42 g, 25.3 mmol) in methanol (3.5 mL) was added over 5 minutes. Immediately a thick precipitate is formed. The reaction mixture is stirred in the ice/water bath for 30 mins. The precipitate was then removed via filtration and the filtrate is used as a hydroxylamine solution in MeOH. Ethyl (2S)-2-ethoxy-3-{4-[(4-methoxypyridin-2-yl)methoxy]phenyl}propanoate (0.108 g, 0.302 mmol) was dissolved in methanol (2 mL) and cooled in an ice/water bath. 4 mL of the aforementioned hydroxylamine in MeOH solution was added. The reaction mixture was stirred at this temperature and monitored by HPLC. After the reaction was interpreted to be complete (4 hours, HPLC-MS) it was concentrated in vacuo, diluted with water (4 mL) and the pH is adjusted to neutral with 1N aq. HCl. The mixture was extracted with EtOAc (2×5 mL) and the EtOAc layer was extracted with 1N HCl (1×10 mL). The acidic aqueous layer was purified on CombiFlash Rf instrument using 15.5 g C18Aq Gold column (0.1% TFA in MeCN:0.1% TFA in water gradient). Fractions were collected on 214 nM and were identified by HPLC-MS, pooled and stripped down in the presence of HCl (2×) to give (2S)-2-ethoxy-N-hydroxy-3-{4-[(4-methoxypyridin-2-yl)methoxy]phenyl}propanamide hydrochloride (Compound No. 3) (0.0514 g) as an oil.

$^1$H NMR (300 MHz, METHANOL-d4) δ ppm 1.12 (t, J=6.98 Hz, 3 H), 2.88 (m, 1 H), 3.02 (m, 1 H), 3.36 (m, 1

H), 3.55 (m, 1 H), 3.89 (dd, J=7.59, 4.98 Hz, 1 H), 4.18 (s, 3 H), 5.41 (s, 2 H), 7.04 (d, J=8.66 Hz, 2 H), 7.25 (d, J=8.66 Hz, 2 H), 7.51 (dd, J=6.98, 2.70 Hz, 1 H), 7.65 (d, J=2.70 Hz, 1 H), 8.62 (d, J=6.99 Hz, 1 H).

HPLC retention Time: 2.158 min

LCMS: 369.0 (M+Na)+; 347.0 (M+H)+; 345.0 (M–H)–

Example 9

(2S)-2-ethoxy-N-methoxy-3-{4-[(4-methoxypyridin-2-yl)methoxy]phenyl}-N-methylpropanamide (Compound No. 4)

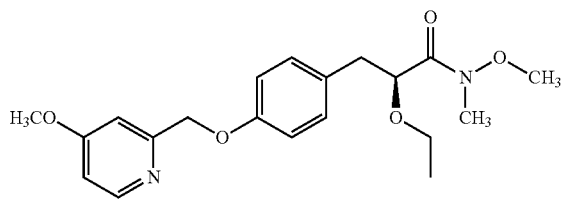 [SMILES: CCO[C@@H](Cc1ccc(OCc2cc(OC)ccn2)cc1)C(=O)N(C)OC]

Ethyl (2S)-2-ethoxy-3-{4-[(4-methoxypyridin-2-yl)methoxy]phenyl}propanoate (100 mg, 0.3 mmol) was dissolved in tetrahydrofuran (4 mL) and N,O-dimethylhydroxylamine hydrochloride (81 mg, 0.83 mmol) was added and the reaction mixture was cooled in an ice/water bath. To this mixture was added isopropylmagnesium chloride lithium chloride complex in tetrahydrofuran (2.6 mL, 1.3 M, 3.3 mmol) and the reaction was monitored by HPLC. When the reaction interpreted to be complete (2 h) it was quenched with water (25 mL), and extracted with EtOAc (25 mL). The organic phase was dried over $Na_2SO_4$, filtered and concentrated in vacuo. The crude material was purified by chroimatography on a CombiFlash Rf instrument (4 g Gold column, acetone:hexane gradient, collecting at 225 nM). Fractions were identified by HPLC-MS, combined, and concentrated in vacuo to afford the desired product (2S)-2-ethoxy-N-methoxy-3-{4-[(4-methoxypyridin-2-yl)methoxy]phenyl}-N-methylpropanamide (Compound No. 4) (0.012 g) as a clear, colorless oil.

$^1$H NMR (300 MHz, CHLOROFORM-d) δ ppm 1.19 (t, J=6.98 Hz, 3 H), 2.91-3.00 (2 H), 3.18 (s, 3 H), 3.36 (m, 1 H), 3.49-3.65 (4 H), 3.87 (s, 3 H), 4.38 (t, J=6.33 Hz, 1 H), 5.15 (s, 2 H), 6.76 (dd, J=5.82, 2.56 Hz, 1 H), 6.92 (d, J=8.66 Hz, 2 H), 7.07 (d, J=2.42 Hz, 1 H), 7.20 (d, J=8.57 Hz, 2 H), 8.42 (d, J=5.77 Hz, 1 H).

HPLC retention Time: 2.622 min

LCMS: 397.0 (M+Na)+; 375.1 (M+H)+

Example 10

(2S)-2-ethoxy-N-methoxy-3-{4-[(4-methoxypyridin-2-yl)methoxy]phenyl}propanamide hydrochloride (Compound No. 5)

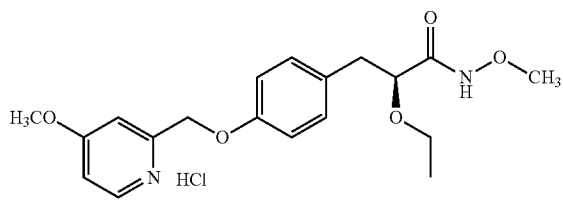 [SMILES: CCO[C@@H](Cc1ccc(OCc2cc(OC)ccn2)cc1)C(=O)NOC ; Cl]

The sodium salt of (2S)-2-ethoxy-3-{4-[(4-methoxypyridin-2-yl)methoxy]phenyl}propanoic acid (60 mg, 0.2 mmol) was suspended in acetonitrile (0.500 mL) and triethylamine (50 uL, 0.4 mmol) was added followed by methoxylamine hydrochloride (18.1 mg, 0.217 mmol) and N,N,N',N'-tetramethyl-O-(7-azabenzotriazol-1-yl)uronium hexafluorophosphate (82.3 mg, 0.216 mmol). The reaction mixture was monitored by HPLC. After the reaction was judged to be complete (2 h) it was diluted with water (5 mL) and 6N HCl (1.0 mL) was added. The aqueous solution was purified by CombiFlash Rf (C18aq 15.5 g Gold column, 0.1% TFA in MeCN: 0.1% TFA in water gradient, collecting at 214 nM). Appropriate fractions were identified with HPLC-MS, pooled and concentrated using a lyopholizer in the presence of conc HCl to give (2S)-2-ethoxy-N-methoxy-3-{4-[(4-methoxypyridin-2-yl)methoxy]phenyl}propanamide (Compound No. 5) (0.0242 g) as a fluffy, white solid.

$^1$H NMR (300 MHz, METHANOL-d4) δ ppm 1.15 (t, J=6.98 Hz, 3 H), 2.91 (m, 1 H), 3.03 (m, 1 H), 3.41 (m, 1 H), 3.49-3.62 (4 H), 3.90 (dd, J=7.08, 5.22 Hz, 1 H), 4.18 (s, 3 H), 5.43 (s, 2 H), 7.05 (d, J=8.75 Hz, 2 H), 7.25 (d, J=8.75 Hz, 2 H), 7.51 (dd, J=6.98, 2.79 Hz, 1 H), 7.66 (d, J=2.70 Hz, 1 H), 8.63 (d, J=6.98 Hz, 1 H).

HPLC retention Time: 2.343 min

LCMS: 383.1 (M+Na)+; 361.1 (M+H)+

Example 11

(2S)-2-ethoxy-N-hydroxy-3-{4-[(4-methoxypyridin-2-yl)methoxy]phenyl}-N-methylpropanamide hydrochloride (Compound No. 6)

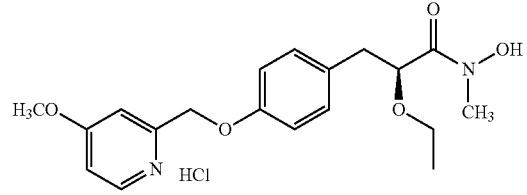 [SMILES: CCO[C@@H](Cc1ccc(OCc2cc(OC)ccn2)cc1)C(=O)N(C)O ; Cl]

The sodium salt of (2S)-2-ethoxy-3-{4-[(4-methoxypyridin-2-yl)methoxy]phenyl}propanoic acid (52 mg, 0.15 mmol) was suspended in acetonitrile (0.50 mL) and triethylamine (50 uL, 0.4 mmol) was added followed by N-methyl-hydroxylamine hydrochloride (21 mg, 0.25 mmol) and N,N,N',N'-tetramethyl-O-(7-azabenzotriazol-1-yl)uronium hexafluorophosphate (72 mg, 0.19 mmol). The reaction mixture was stirred at RT, for 2 hours, then water (2.0 mL) was added followed by 6N aq. HCl (0.5 mL). The aqueous solution was purified by CombiFlash Rf (C18aq Gold 15.5 g column, 0.1% TFA in MeCN: 0.1% TFA in water gradient, collecting at 214 nM). Appropriate fractions were identified by HPLC-MS, pooled, treated with 6N aq. HCl (0.5 mL) and lyophilized to give (2S)-2-ethoxy-N-hydroxy-3-{4-[(4-methoxypyridin-2-yl)methoxy]phenyl}-N-methylpropanamide hydrochloride (Compound No. 6) (0.012 g) as a white solid.

$^1$H NMR (300 MHz, METHANOL-d4) δ ppm 1.15 (t, J=6.98 Hz, 3 H), 2.85-3.09 (2 H), 3.41 (dq, J=9.38, 6.99 Hz, 1 H), 3.49-3.62 (4 H), 3.90 (dd, J=7.08, 5.22 Hz, 1 H), 4.18 (s, 3 H), 5.42 (s, 2 H), 7.05 (d, J=8.75 Hz, 2 H), 7.25 (d, J=8.75 Hz, 2 H), 7.51 (dd, J=6.98, 2.79 Hz, 1 H), 7.66 (d, J=2.70 Hz, 1 H), 8.63 (d, J=6.98 Hz, 1 H).

HPLC retention Time: 2.347 min

LCMS: 383.1 (M+Na)+; 361.1 (M+H)+

Example 12

Ethyl (2R)-2-ethoxy-3-{4-[2-(3-methoxyphenyl)-2-oxoethoxy]phenyl}propanoate

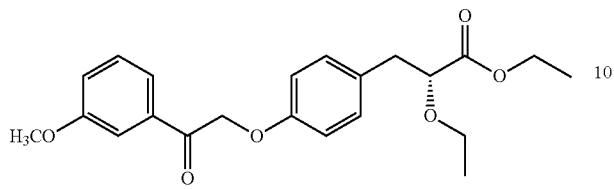

To a stirring solution of ethyl (2R)-2-ethoxy-3-(4-hydroxyphenyl)propanoate (205 mg, 0.860 mmol) in acetone (5 ml) was added a solution of 2-bromo-3'-methoxyacetophenone (220 mg, 0.95 mmol) in acetone (2.0 mL) followed by solid potassium carbonate (140 mg, 1.0 mmol). The mixture was stirred at RT overnight then was cast into water (50 mL) and extracted with EtOAc (2×25 mL). The combined organic phases were dried (Na$_2$SO$_4$), filtered and evaporated in vacuo to afford ethyl (2R)-2-ethoxy-3-{4-[2-(3-methoxyphenyl)-2-oxoethoxy]phenyl}propanoate (0.234 g) as a clear, colorless oil.

$^1$H NMR (400 MHz, CHLOROFORM-d) δ ppm 1.14-1.28 (6 H), 2.96 (d, J=6.63 Hz, 2 H), 3.36 (m, 1 H), 3.61 (m, 1 H), 3.88 (s, 3 H), 3.98 (t, J=6.63 Hz, 1 H), 4.18 (q, J=7.05 Hz, 2 H), 5.26 (s, 2 H), 7.14-7.22 (2 H), 7.36-7.45 (2 H), 7.51-7.56 (2 H), 7.59 (m, 1 H) 7.59 (d, J=7.67 Hz, 1 H).

HPLC retention Time: 4.533 min

LCMS: 409.2 (M+Na)+.

Example 13

(2R)-2-Ethoxy-3-{4-[2-(3-methoxyphenyl)-2-oxoethoxy]phenyl}propanoic acid

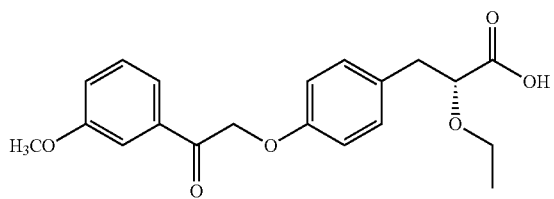 [SMILES: CCO[C@H](Cc1ccc(OCC(=O)c2cccc(OC)c2)cc1)C(=O)O]

To a stirring solution of ethyl (2R)-2-ethoxy-3-{4-[2-(3-methoxyphenyl)-2-oxoethoxy]phenyl}propanoate (70 mg, 0.2 mmol) in MeOH (2 ml) was added 2M aq. LiOH until pH ca. 10 was achieved. After 3 hours, HPLC indicates that the reaction is complete, water (5 mL) was added and 6M aq. HCl was added dropwise until pH was adjusted to ca. 3-4. The solution was extracted with EtOAc (2×10 mL), and the combined extracts were dried (Na$_2$SO$_4$), filtered and evaporated in vacuo to give the crude product as a yellow oil. The crude material was purified by silica gel chromatography eluting with 0-5% acetone/DCM. Fractions containing product were identified by HPLC-MS, pooled and evaporated in vacuo to afford (2R)-2-ethoxy-3-{4-[2-(3-methoxyphenyl)-2-oxoethoxy]phenyl}propanoic acid (38 mg) as a clear, colorless oil.

$^1$H NMR (400 MHz, CHLOROFORM-d) δ ppm 1.19 (t, J=7.05 Hz, 3 H), 2.96 (m, 1 H), 3.11 (m, 1 H), 3.46 (m, 1 H), 3.61 (m, 1 H), 3.91 (s, 3 H), 4.06 (dd, J=7.57, 4.25 Hz, 1 H), 5.27 (s, 2 H), 6.89 (d, J=8.71 Hz, 2 H), 7.18 (m, 2 H), 7.43 (t, J=7.98 Hz, 1 H), 7.52-7.66 (3 H).

Retention Time: 3.768 min

LCMS: 359.2 (M+H)+; 357.2 (M−H)−.

Example 14

(2R)-2-ethoxy-N-methoxy-3-{4-[2-(3-methoxyphenyl)-2-oxoethoxy]phenyl}propanamide (Compound No. 8)

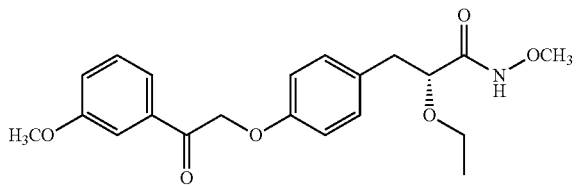 [SMILES: CCO[C@H](Cc1ccc(OCC(=O)c2cccc(OC)c2)cc1)C(=O)NOC]

To a stirring solution of (2R)-2-ethoxy-3-{4-[2-(3-methoxyphenyl)-2-oxoethoxy]phenyl}propanoic acid (400 mg, 1 mmol) in N,N-dimethylformamide (3 mL) was added N,N,N',N'-tetramethyl-O-(7-azabenzotriazol-1-yl)uronium hexafluorophosphate (53 mg, 1.40 mmol), N,N-diisopropylethylamine (0.583 mL, 3.35 mmol,) and methoxyammonium chloride (118 mg, 1.40 mmol). The resulting mixture was allowed to stir at RT overnight. The reaction was diluted with water (25 mL), extracted with EtOAc (2×25 mL) and the combined organic phases were dried (Na$_2$SO$_4$), filtered and evaporated in vacuo to give the crude product as a yellow oil. The crude product was purified by chromatography on a reverse-phase combi-flash column (C18aq Gold 15.5 g column) with 0-70% 0.1% TFA in MeCN: 0.1% TFA in water gradient, collecting @ 214 nm. Appropriate fractions were identified by HPLC-MS, pooled and partitioned between saturated NaHCO$_3$ and EtOAc. The organic phase was dried (Na$_2$SO$_4$), filtered and evaporated in vacuo to give (2R)-2-ethoxy-N-methoxy-3-{4-[2-(3-methoxyphenyl)-2-oxoethoxy]phenyl}propanamide (Compound No. 8) (54 mg) as an amber oil.

$^1$H NMR (300 MHz, CHLOROFORM-d) δ ppm 1.15 (t, J=6.98 Hz, 3 H), 2.89 (m, 1 H), 3.11 (m, 1 H), 3.65 (s, 3 H), 3.88 (s, 3 H), 3.99 (dd, J=6.66, 3.86 Hz, 1 H), 6.88 (m, 2 H), 7.10-7.23 (3 H), 7.42 (t, J=7.96 Hz, 1 H), 7.50-7.62 (2 H), 8.80 (s, 1 H).

HPLC retention Time: 2.270 min

LCMS: 388.1 (M+H)+; 386.1 (M−H)−

Example 15

(2R)-2-ethoxy-N-methoxy-3-{4-[2-(3-methoxyphenyl)-2-oxoethoxy]phenyl}-N-methylpropanamide (Compound No. 11)

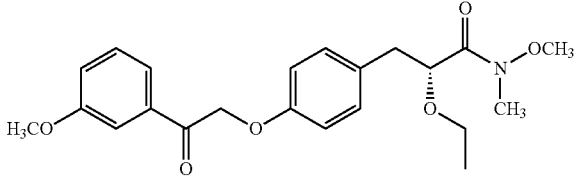 [SMILES: CCO[C@H](Cc1ccc(OCC(=O)c2cccc(OC)c2)cc1)C(=O)N(C)OC]

To a stirring solution of (2R)-2-ethoxy-3-{4-[2-(3-methoxyphenyl)-2-oxoethoxy]phenyl}propanoic acid (140 mg, 0.39 mmol) in N,N-dimethylformamide (5 mL) was added N,N,N',N'-tetramethyl-O-(7-azabenzotriazol-1-yl)uronium hexafluorophosphate (186 mg, 0.488 mmol), N,N-diisopropylethylamine (0.204 mL, 1.17 mmol) and N,O-dimethylhydroxylamine hydrochloride (47.6 mg, 0.488 mmol). The mixture was allowed to stir at RT overnight, then was purified by chromatography on a 30 g C18Aq gold reverse-phase combi-flash column eluting with 0-70% 0.1% TFA in MeCN: 0.1% TFA in water gradient, collecting @ 214 nm. Appropriate fractions were identified by HPLC-MS were combined and concentrated in vacuo to give 2R)-2-ethoxy-N-methoxy-3-{4-[2-(3-methoxyphenyl)-2-oxoethoxy]phenyl}-N-methylpropanamide (Compound No. 11) (65 mg, 41%) as a yellow oil.

$^1$H NMR (300 MHz, CHLOROFORM-d) δ ppm 1.18 (t, J=6.98 Hz, 3 H), 2.95 (d, J=6.61 Hz, 2 H), 3.13-3.23 (3 H), 3.34 (dd, J=8.89, 7.03 Hz, 1 H), 3.46-3.60 (4 H), 3.88 (s, 3 H), 4.37 (br. s., 1 H), 5.26 (s, 2 H), 6.87 (m, 2 H), 7.12-7.31 (3 H), 7.42 (t, J=7.96 Hz, 1 H), 7.48-7.63 (2 H).

HPLC retention Time: 3.734 min
LCMS: 402.2 (M+H)+

Example 16

(2R)-2-ethoxy-3-{4-[(2S)-2-hydroxy-2-(3-methoxyphenyl)ethoxy]phenyl}-N-methoxypropanamide (Compound No. 18)

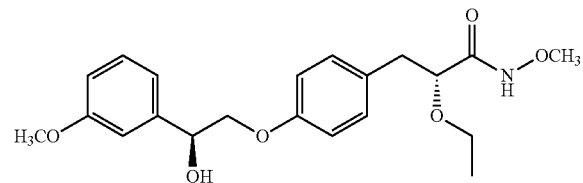 [SMILES: CCO[C@H](Cc1ccc(OC[C@@H](O)c2cccc(OC)c2)cc1)C(=O)NOC]

A stirring mixture of dichloro(p-cymene)ruthenium(II) dimer (1.2 mg, 0.0000020 mol) and (1R,2R)-(−)-N-p-Tosyl-1,2-diphenylethylenediamine (1.4 mg, 0.0000039 mol) and triethylamine (0.05 ml) in isopropanol (5 ml) was refluxed for one hour. The mixture was allowed to cool to RT and evaporated in vacuo. To the resulting dark brown solid was added DMF (5 ml), (2R)-2-ethoxy-N-methoxy-3-{4-[2-(3-methoxyphenyl)-2-oxoethoxy]phenyl}propanamide (84 mg, 0.00022 mol) and formic acid-triethylamine complex, 5:3 (0.5 g). After stirring for 4 hours at RT, the reaction was quenched with saturated aq. NaHCO$_3$ (10 mL) and was partitioned between saturated NaHCO$_3$ (10 mL) and EtOAc (25 mL). The aq. phase was extracted with EtOAc (15 mL) and the combined organic phases were washed with brine (2×25 mL), dried (Na$_2$SO$_4$), filtered and evaporated in vacuo. The resulting crude product was purified by chromatography on a 15.5 g C18Aq Gold combiflash column eluting with 0-60% 0.1% TFA in MeCN: 0.1% TFA in water gradient, collecting @ 214 nm. Appropriate fractions were identified by HPLC-MS, were pooled and evaporated in vacuo to give (2R)-2-ethoxy-3-{4-[(2S)-2-hydroxy-2-(3-methoxyphenyl)ethoxy]phenyl}-N-methoxypropanamide (Compound No. 18) (27 mg) as a pale pink oil.

$^1$H NMR (300 MHz, CHLOROFORM-d) δ ppm 1.16 (t, J=6.98 Hz, 3 H), 2.90 (m, 1 H), 3.11 (m, 1 H), 3.33-3.60 (2 H), 3.67 (s, 3 H), 3.84 (s, 3 H), 3.93-4.22 (5 H), 5.11 (dd, J=8.66, 3.07 Hz, 1 H), 6.72-6.96 (3 H), 7.02 (m, 2 H), 7.15 (d, J=8.57 Hz, 1 H), 7.31 (m, 1 H), 8.91 (br. s., 1 H).

HPLC retention Time: 3.156 min
LCMS: 390.2 (M+H)+

Example 17

Ethyl (2R)-2-ethoxy-3-{4-[(2S)-2-hydroxy-2-(3-methoxyphenyl)ethoxy]phenyl}propanoate

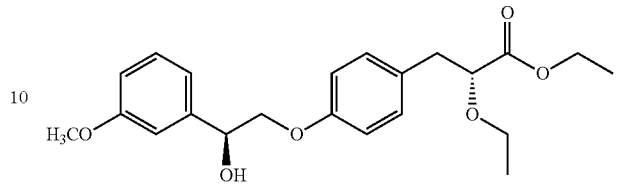

A stirring mixture of dichloro(p-cymene)ruthenium(II) dimer (1.6 mg, 0.0026 mmol and (1R,2R)-(−)-N-p-tosyl-1,2-diphenylethylenediamine (1.9 mg, 0.0052 mmol) and triethylamine (0.05 ml) in isopropanol (5 ml) was refluxed for one hour. The mixture was allowed to cool to RT and evaporated in vacuo. To the resulting dark brown solid was added DMF (5 ml), ethyl (2R)-2-ethoxy-3-{4-[2-(3-methoxyphenyl)-2-oxoethoxy]phenyl}propanoate (112 mg, 0.290 mmol) and formic acid trietylamine complex, 5:3 (1.5 ml). After two hours the reaction was complete as judged by HPLC. The reaction was quenched by the addition of MeOH (1 ml) and stirred for 5 min. The reaction mixture was evaporated in vacuo on the high vac rotovap. The brown residue was partitioned between DCM (25 mL) and saturated aqueous NaHCO$_3$ (25 mL) and the aq. phase was extracted with DCM (25 mL). The combined organic phases were washed with brine (50 mL), dried (Na$_2$SO$_4$), filtered and evaporated in vacuo. The resulting brown oil was chromatographed on a small MM column eluting with 0-10% ether/DCM. Fractions containing desired product were identified by HPLC-MS, pooled and evaporated in vacuo to give 110 mg of ethyl (2R)-2-ethoxy-3-{4-[(2S)-2-hydroxy-2-(3-methoxyphenyl)ethoxy]phenyl}propanoate as a pale pink oil.

$^1$H NMR (400 MHz, CHLOROFORM-d) δ ppm 1.17 (t, J=7.05 Hz, 3 H), 1.24 (t, J=7.05 Hz, 3 H), 2.80 (s, 1 H), 2.96 (m, 2 H), 3.35 (m, 1 H), 3.60 (m, 1 H), 3.84 (s, 3 H), 3.93-4.03 (2 H), 4.10 (dd, J=9.54, 3.11 Hz, 1 H), 4.18 (q, J=7.05 Hz, 2 H), 5.10 (dd, J=8.71, 2.28 Hz, 1 H), 6.80-6.92 (3 H), 6.98-7.06 (2 H), 7.17 (d, J=8.71 Hz, 2 H), 7.31 (t, J=7.98 Hz, 1 H).

HPLC retention time: 4.297 min.
LCMS: 383.2 (M+Na)$^+$; 359.3 (M−H)$^-$

Example 18

(2R)-2-ethoxy-N-hydroxy-3-{4-[(2S)-2-hydroxy-2-(3-methoxyphenyl)ethoxy]phenyl}propanamide (Compound No. 2)

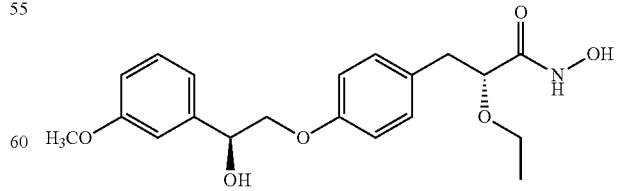

Hydroxylamine hydrochloride (1.17 g, 16.9 mmol) was dissolved/suspended in methanol (6.11 mL, 151 mmol). The reaction mixture was cooled in an ice/water bath. Potassium hydroxide (1.42 g, 25.3 mmol) in methanol (3.36 mL, 83.0 mmol) was added slowly at first then all in one portion.

Immediately a thick precipitate is formed. The reaction mixture is stirred in the ice/water bath for 30 mins. The precipitate was then removed via filtration and the filtrate is used as a hydroxylamine solution in MeOH. To a stirring solution of ethyl (2R)-2-ethoxy-3-{4-[(2S)-2-hydroxy-2-(3-methoxyphenyl)ethoxy]phenyl}propanoate (100 mg, 0.2 mmol) in MeOH (2 ml) was added the aforementioned hydroxylamine solution in MeOH (1 ml). After stirring overnight, the reaction mixture was evaporated in vacuo. The resulting solid was treated with a small volume of 1M HCl and then dissolved in DMF. Chromatographed on a 15 g C18aq Gold column, eluting with 0-70% 0.1% TFA in MeCN: 0.1% TFA in water gradient, collecting @ 254 nm. Fractions containing product were combined and neutralized with saturated NaHCO3 then extracted with EtOAc. Combined extracts dried (Na$_2$SO$_4$), filtered and evaporated in vacuo to give (45 mg) of the title compound (Compound No. 2) as a pale yellow oil.

$^1$H NMR (300 MHz, MeOD) δ ppm 1.12 (t, J=6.98 Hz, 3 H) 2.78-2.90 (m, 1 H) 2.91-3.02 (m, 1 H) 3.36 (s, 3 H) 3.52 (dd, J=9.31, 6.98 Hz, 1 H) 3.77-3.89 (m, 4 H) 3.95-4.11 (m, 1 H) 4.99 (dd, J=6.89, 4.75 Hz, 1 H) 6.79-6.92 (m, 3 H) 6.99-7.07 (m, 2 H) 7.15 (d, J=8.66 Hz, 2 H) 7.28 (t, J=7.82 Hz, 1 H)

Retention Time: 2.937 min
LCMS: 376.2 (M+H)+

Example 19

(2R)-2-ethoxy-3-{4-[(2R)-2-hydroxy-2-(3-methoxyphenyl)ethoxy]phenyl}-N-methoxypropanamide (Compound No. 19)

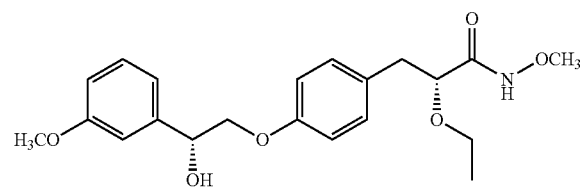 [SMILES: CCO[C@H](Cc1ccc(OC[C@H](O)c2cccc(OC)c2)cc1)C(=O)NOC]

A mixture of dichloro(p-cymene)ruthenium(II) dimer (0.91 mg, 0.0015 mmol), (1S,2S)-(+)-N-p-tosyl-1,2-diphenylethylenediamine (1.1 mg, 0.0029 mmol) and triethylamine (0.002 mL, 0.01 mmol) in isopropyl alcohol (0.6 mL) was refluxed for 30 minutes. The reaction mixture was allowed to cool to RT and then evaporated in vacuo. To the resulting brown residue was added a solution of (2R)-2-ethoxy-N-methoxy-3-{4-[2-(3-methoxyphenyl)-2-oxoethoxy]phenyl}propanamide (64 mg, 0.16, mol) in DMF (2 ml) followed by formic acid-triethylamine complex (0.062 g, 0.42 mmol). The mixture was allowed to stir at RT overnight, then was quenched with saturated NaHCO$_3$ (2 mL) then partitioned between saturated NaHCO$_3$ (10 mL) and EtOAc (10 mL); the aq. phase was extracted with EtOAc (10 mL) and the combined organic phases were washed with brine (25 mL), dried (Na$_2$SO$_4$), filtered and concentrated in vacuo. The crude product was purified by chromatography on a 15.5 g C18Aq Gold column eluting with 0-50% 0.1% TFA in MeCN: 0.1% TFA in water gradient, collecting @ 214 nm. Appropriate fractions were identified by HPLC-MS, pooled and concentrated in vacuo to afford the (2R)-2-ethoxy-3-{4-[(2R)-2-hydroxy-2-(3-methoxyphenyl)ethoxy] phenyl}-N-methoxypropanamide (Compound No. 19) (25 mg) as a pale yellow oil.

$^1$H NMR (300 MHz, CHLOROFORM-d) δ ppm 1.16 (t, J=7.03 Hz, 3 H), 2.93 (m, 2 H), 3.10 (m, 2 H), 3.46 (m, 2 H), 3.68 (s, 3 H), 3.84 (s, 3 H), 3.94-4.04 (2 H) 4.11 (m, 1 H), 5.11 (dd, J=8.75, 2.98 Hz, 3 H), 6.77-6.95 (3 H), 7.03 (m, 2 H), 7.16 (d, J=8.57 Hz, 2 H), 7.32 (t, J=8.06 Hz, 1 H), 8.84 (s, 1 H).

HPLC retention Time: 3.150 min
LCMS: 390.2 (M+H)+; 388.1 (M−H)−

Example 20

Ethyl (2S)-2-ethoxy-3-{4-[2-(3-methoxyphenyl)-2-oxoethoxy]phenyl}propanoate

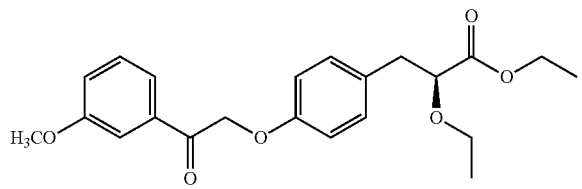 [SMILES: CCOC(=O)[C@H](Cc1ccc(OCC(=O)c2cccc(OC)c2)cc1)OCC]

To a stirring solution of ethyl (2S)-2-ethoxy-3-(4-hydroxyphenyl)propanoate (560 mg, 2.4 mmol), in acetone (5.0 mL), was added a solution 2-bromo-3'-methoxyacetophenone (590 mg, 2.6 mmol), in acetone (2 ml). This was followed by the addition of solid potassium carbonate (390 mg, 2.8 mmol) in one portion. The mixture was allowed to stir at RT overnight. The reaction mixture was cast into water (25 mL) was extracted with EtOAc (2×25 mL) and the combined organic phases were dried (Na$_2$SO$_4$), filtered and evaporated in vacuo. The resulting yellow oil was purified by chromatography a flash column, eluting with 0-20% acetone/DCM. Fractions containing product were identified by HPLC-MS, combined and evaporated in vacuo to give ethyl (2S)-2-ethoxy-3-{4-[2-(3-methoxyphenyl)-2-oxoethoxy]phenyl}propanoate (347 mg, 38%) as a clear, colorless oil.

$^1$H NMR (400 MHz, CHLOROFORM-d) δ ppm 1.09-1.28 (6 H), 2.94 (d, J=6.43 Hz, 2 H), 3.34 (m, 1 H), 3.61 (m, 1 H), 3.85 (s, 3 H), 3.96 (t, J=6.63 Hz, 1 H), 4.15 (q, J=7.26 Hz, 2 H), 5.24 (s, 2 H), 6.85 (m, 2 H), 7.10-7.21 (3 H), 7.39 (t, J=7.88 Hz, 1 H), 7.56 (d, J=7.88 Hz, 2 H).

HPLC retention Time: 4.582 min
LCMS: 409.1 (M+Na)+

Example 21

(2S)-2-ethoxy-3-{4-[2-(3-methoxyphenyl)-2-oxoethoxy]phenyl}propanoic acid

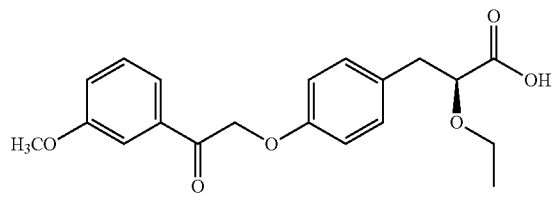 [SMILES: CCO[C@@H](Cc1ccc(OCC(=O)c2cccc(OC)c2)cc1)C(=O)O]

To a stirring solution of ethyl (2S)-2-ethoxy-3-{4-[2-(3-methoxyphenyl)-2-oxoethoxy]phenyl}propanoate (70 mg, 0.2 mmol) in MeOH (2 ml) was added 2M aq. LiOH until pH ca. 10 was achieved. After 3 hours water (15 mL) was added, then 6M aq. HCl was added dropwise until pH ca. 3-4 was realized. The mixture was extracted with EtOAc (2×15 mL), and the combined extracts were dried (Na₂SO₄), filtered and evaporated in vacuo. The resulting yellow oil was purified by flash chromatography eluting with 0-5% acetone/DCM. Fractions containing product were identified by HPLC-MS, combined and evaporated in vacuo to afford (2S)-2-ethoxy-3-{4-[2-(3-methoxyphenyl)-2-oxoethoxy]phenyl}propanoic acid (38 mg, 60%) as a clear, colorless oil.

$^1$H NMR (400 MHz, CHLOROFORM-d) δ ppm 1.19 (t, J=7.05 Hz, 3 H), 2.96 (m, 1 H), 3.11 (m, 1 H), 3.46 (m, 1 H), 3.61 (m, 1 H), 3.91 (s, 3 H), 4.06 (dd, J=7.57, 4.25 Hz, 1 H), 5.27 (s, 2 H), 6.89 (d, J=8.71 Hz, 2 H), 7.18 (m, 2 H), 7.43 (t, J=7.98 Hz, 1 H), 7.52-7.66 (3 H).

HPLC retention Time: 3.761 min

LCMS: 359.3 (M+H)⁺; 357.3 (M−H)⁻.

Example 22

(2S)-2-ethoxy-N-methoxy-3-{4-[2-(3-methoxyphenyl)-2-oxoethoxy]phenyl}Propanamide (Compound No. 13)

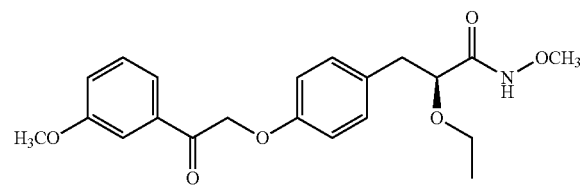 [SMILES: CCO[C@@H](Cc1ccc(OCC(=O)c2cccc(OC)c2)cc1)C(=O)NOC]

(2S)-2-ethoxy-3-{4-[2-(3-methoxyphenyl)-2-oxoethoxy]phenyl}propanoic acid (0.438 g, 1.22 mmol) was dissolved in N,N-Dimethylformamide (5.00 mL). N,N-diisopropylethylamine (639 uL, 3.67 mmol) was added followed by N,N,N',N'-tetramethyl-O-(7-azabenzotriazol-1-yl)uronium hexafluorophosphate (0.558 g, 1.47 mmol) and methoxylamine hydrochloride (0.204 g, 2.44 mmol). The reaction mixture was stirred at RT for 30 mins then was diluted with 1N aq. HCl (25 mL). The mixture was extracted with ether (2×25 mL). The combined organic phases were washed with brine (50 mL), dried over Na₂SO₄, filtered, and concentrated in vacuo. The crude product was purified by chromatography on a CombiFlash Rf instrument (12 g Gold Silica column, 0-100% EtOAc:hexane gradient, 254 nM collection wavelength). Appropriate fractions, identified by HPLC-MS were combined and concentrated to afford (2S)-2-ethoxy-N-methoxy-3-{4-[2-(3-methoxyphenyl)-2-oxoethoxy]phenyl}propanamide (0.410 g; 86.6%) as a clear, colorless oil.

$^1$H NMR (300 MHz, CHLOROFORM-d) δ ppm 1.16 (t, J=6.98 Hz, 3 H), 2.92 (m, 1 H), 3.11 (m, 1 H) 3.40-3.57 (2 H), 3.65 (s, 3 H), 3.88 (s, 3 H), 4.00 (dd, J=6.71, 3.82 Hz, 1 H), 5.26 (s, 2 H), 6.87 (d, J=8.66 Hz, 2 H), 7.11-7.21 (3 H), 7.42 (t, J=7.92 Hz, 1 H), 7.53 (m, 1 H), 7.58 (td, J=7.59, 1.28 Hz, 1 H), 8.79 (br. s., 1 H).

HPLC retention Time: 3.574 min

LCMS: 410.0 (M+Na)+; 388.0 (M+H)+; 386.0 (M−H)−

Example 23

(2S)-2-ethoxy-N-methoxy-3-{4-[2-(3-methoxyphenyl)-2-oxoethoxy]phenyl}-N-methylpropanamide (Compound No. 14)

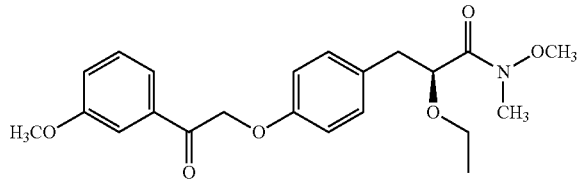 [SMILES: CCO[C@@H](Cc1ccc(OCC(=O)c2cccc(OC)c2)cc1)C(=O)N(C)OC]

(2S)-2-ethoxy-3-{4-[2-(3-methoxyphenyl)-2-oxoethoxy]phenyl}propanoic acid (0.472 g, 1.32 mmol) was dissolved in N,N-dimethylformamide (5.00 mL), then N,N-diisopropylethylamine (688 uL, 3.95 mmol) was added followed by N,N,N',N'-tetramethyl-O-(7-azabenzotriazol-1-yl)uronium hexafluorophosphate (0.601 g, 1.58 mmol), and N,O-dimethylhydroxylamine hydrochloride (0.257 g, 2.63 mmol). The reaction mixture was stirred at RT for 30 mins then diluted with 1N aq. HCl (25 mL), and extracted with ether (2×30 mL). The combined organics were washed with brine (30 mL), dried over Na₂SO₄, filtered and concentrated in vacuo. The resulting crude product was purified by cheomatography on a CombiFlash Rf instrument (12 g Gold silica gel column, 0-100% EtOAc:hexane gradient, 254 nM collection wavelength). Appropriate fractions were identified by HPLC-MS, combined and concentrated to afford (2S)-2-ethoxy-N-methoxy-3-{4-[2-(3-methoxyphenyl)-2-oxoethoxy]phenyl}-N-methylpropanamide (Compound No. 14) (0.481 g) as an ivory solid.

$^1$H NMR (300 MHz, CHLOROFORM-d) δ ppm 1.18 (t, J=6.98 Hz, 3 H), 2.90-2.99 (2 H), 3.18 (s, 3 H), 3.35 (m, 1 H), 3.48-3.60 (4 H), 3.88 (s, 3 H), 4.37 (t, J=6.47 Hz, 1 H), 5.26 (s, 2 H), 6.88 (d, J=8.75 Hz, 2 H), 7.14-7.23 (3 H), 7.42 (t, J=7.92 Hz, 1 H), 7.54 (dd, J=2.47, 1.54 Hz, 1 H), 7.58 (m, 1 H).

HPLC retention Time: 3.927 min

LCMS: 423.9 (M+Na)+; 402.0 (M+H)+

Example 24

(2S)-2-ethoxy-3-{4-[(2S)-2-hydroxy-2-(3-methoxyphenyl)ethoxy]phenyl}-N-methoxypropanamide (Compound No. 12)

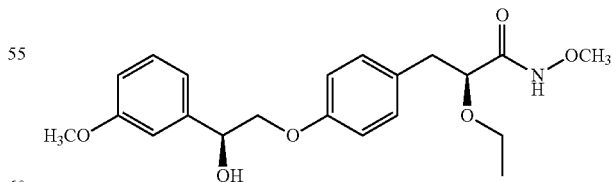

A stirring mixture of dichloro(p-cymene)ruthenium(II) dimer (1.5 mg, 0.0024 mmol) and (1R,2R)-(−)-N-p-tosyl-1,2-diphenylethylenediamine (1.7 mg, 0.0047 mmol) and triethylamine (0.05 ml) in isopropanol (5 ml) was refluxed for one hour. The mixture was allowed to cool to RT and evaporated in vacuo. To the resulting dark brown solid was added DMF (5 ml), (2S)-2-ethoxy-N-methoxy-3-{4-[2-(3-methoxyphenyl)-2-oxoethoxy]phenyl}propanamide (102 mg, 0.000263 mol) and formic acid:triethylamine complex (5:3, 0.5 g). After stirring for 4 hours at RT, the reaction mixture was quenched with saturated aqueous NaHCO$_3$ (5 mL) and partitioned between saturated NaHCO$_3$ (20 mL) and EtOAc (2×25 mL). The combined organic extracts were washed with brine (50 mL), dried (Na$_2$SO$_4$), filtered and concentrated in vacuo. The crude product was purified by chromatography on a CombiFlash Rf instrument using a 15 g C18Aq Gold column eluting with 0.1% TFA in MeCN: 0.1%1TA in water gradient collecting fractions at 214 nm. Fractions identified by HPLC-MS were pooled and evaporated in vacuo to give 59 mg (58%) of (2S)-2-ethoxy-3-{4-[(2S)-2-hydroxy-2-(3-methoxyphenyl)ethoxy]phenyl}-N-methoxypropanamide (Compound No. 12) as a clear, colorless oil.

$^1$H NMR (300 MHz, CHLOROFORM-d) δ ppm 1.17 (t, J=6.98 Hz, 3 H), 2.89 (m, 1 H), 3.12 (m, 1 H), 3.31-3.57 (5 H), 3.85 (s, 3 H), 3.95-4.22 (3 H), 5.11 (dd, J=8.75, 3.17 Hz, 1 H), 6.77-6.93 (3 H), 7.03 (m, 2 H), 7.16 (d, J=8.66 Hz, 2 H), 7.34 (m, 1 H), 8.89 (br s., 1 H).

HPLC retention Time: 3.153 min

LCMS: 388.1 (M–H)–

Example 25

(2S)-2-ethoxy-3-{4-[(2S)-2-hydroxy-2-(3-methoxyphenyl)ethoxy]phenyl}-N-methoxypropanamide (Compound No. 17)

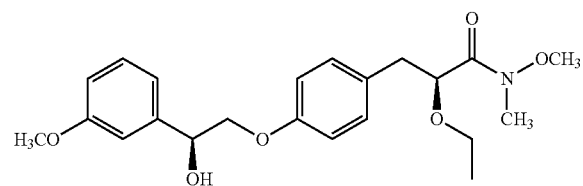

A stirring mixture of dichloro(p-cymene)ruthenium(II) dimer (1.8 mg, 00030 mmol) and (1R,2R)-(–)-N-p-tosyl-1,2-diphenylethylenediamine (2.1 mg, 0.0058 mmol) and triethylamine (0.05 ml) in isopropanol (5 ml) was refluxed for one hour. The mixture was allowed to cool to RT and evaporated in vacuo. To the resulting dark brown solid was added DMF (5 ml), (2S)-2-ethoxy-N-methoxy-3-{4-[2-(3-methoxyphenyl)-2-oxoethoxy]phenyl}-N-methylpropanamide (130 mg, 0.32 mmol) and formic acid trietylamine complex, 5:3 (0.5 g). After stirring for 4 hours at RT, HPLC showed the reaction to be complete. And it was quenched with saturated aq. NaHCO$_3$ (5 mL). Partitioned between saturated aq. NaHCO$_3$ (20 mL) and EtOAc (2×25 mL). The combined organic phases were washed with brine (50 mL), dried (Na$_2$SO$_4$), filtered and concentrated in vacuo. The crude product was purified by chromatography on a 15.5 g C18Aq Gold combiflash column eluting with 0-60% 0.1% TFA in MeCN:0.1% TFA in water gradient, collecting @ 214 nm. Appropriate fractions were identified by HPLC=MS, combined and evaporated in vacuo to give 44 mg of (2S)-2-ethoxy-3-{4-[(2S)-2-hydroxy-2-(3-methoxyphenyl)ethoxy]phenyl}-N-methoxypropanamide (Compound No. 17) as a pale pink oil.

$^1$H NMR (300 MHz, CHLOROFORM-d) δ 1.17 (t, J=6.98 Hz, 3 H), 2.95 (d, J=6.71 Hz, 2 H), 3.20 (s, 3 H), 3.33 (m, 1 H), 3.47-3.60 (4 H), 3.84 (s, 3 H), 3.99 (t, J=9.17 Hz, 1 H), 4.10 (m, 1 H), 4.38 (brs., 1 H), 5.11 (dd, J=8.75, 2.98 Hz, 1 H), 6.80-6.93 (3 H), 7.03 (m, 2 H), 7.17 (d, J=8.57 Hz, 2 H), 7.31 (t, J=8.10 Hz, 1 H).

HPLC retention Time: 3.471 min

LCMS: 404.2 (M+H)+

Example 26

(2S)-2-ethoxy-3-{4-[(2R)-2-hydroxy-2-(3-methoxyphenyl)ethoxy]phenyl}-N-methoxypropanamide (Compound No. 15)

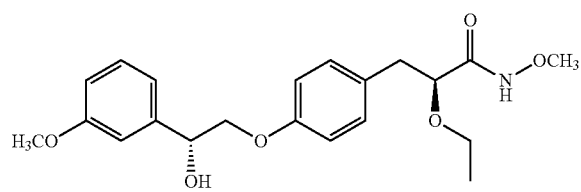 [SMILES: CCO[C@@H](Cc1ccc(OC[C@H](O)c2cccc(OC)c2)cc1)C(=O)NOC]

To a solution of (2S)-2-ethoxy-N-methoxy-3-{4-[2-(3-methoxyphenyl)-2-oxoethoxy]phenyl}propanamide (172 mg, 0.444 mmol) in N,N-dimethylformamide (1.00 mL) was added formic acid-triethylamine complex (189 uL, 5:3, 1.33 mmol), followed by (S,S)-Ts-DENEB (28.9 mg, 0.0444 mmol). The reaction stirred and monitored by HPLC for 4 hours, then was quenched with saturated aq. NaHCO$_3$ (1 mL) and the mixture was purified by direct injection onto CombiFlash instrument (C18Aq Gold Column 15.5 g, 0.1% TFA in MeCN:0.1% TFA in water gradient, 214 nM collection). Desired fractions were identified by HPLC-MS pooled and concentrated in vacuo. The resulting oil was azeotroped from acetonitrile until no more water present was observed then was dried in vacuo to give (2S)-2-ethoxy-3-{4-[(2R)-2-hydroxy-2-(3-methoxyphenyl)ethoxy]phenyl}-N-methoxypropanamide (Compound No. 15) (0.064 g) as a pale yellow oil.

$^1$H NMR (300 MHz, CHLOROFORM-d) δ ppm 1.17 (t, J=6.98 Hz, 3 H), 2.92 (m, 1 H), 3.11 (m, 1 H), 3.50 (m, 2 H), 3.67 (s, 3 H), 3.85 (s, 3 H), 3.95-4.15 (3 H), 5.11 (dd, J=8.66, 3.17 Hz, 1 H), 6.80-6.94 (3 H), 7.03 (m, 2 H), 7.16 (d, J=8.66 Hz, 2 H), 7.31 (d, J=8.20 Hz, 1 H), 8.88 (br. s., 1 H).

HPLC retention Time: 3.279 min

LCMS: 412.1 (M+Na)+; 388.1 (M–H)–

Example 27

(2S)-2-Ethoxy-3-{4-[(2R)-2-hydroxy-2-(3-methoxyphenyl)ethoxy]phenyl}-N-methoxy-N-methylpropanamide (Compound No. 16)

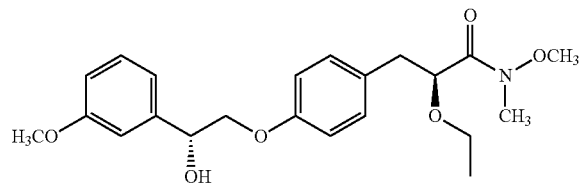 [SMILES: CCO[C@@H](Cc1ccc(OC[C@H](O)c2cccc(OC)c2)cc1)C(=O)N(C)OC]

(2S)-2-ethoxy-N-methoxy-3-{4-[2-(3-methoxyphenyl)-2-oxoethoxy]phenyl}-N-methylpropanamide (65 mg, 0.16 mmol) was dissolved in N,N-dimethylformamide (0.500 mL), (S,S)-Ts-DENEB (11 mg, 0.017 mmol) was added followed by formic acid triethylamine complex (70 uL, 0.5 mmol). The reaction mixture was stirred and monitored by HPLC and after 4 hours was judged to be complete. The reaction was stopped quenched by adding saturated aq. NaHCO$_3$ (0.5 L) and was purified by direct injection onto a CombiFlash Rf instrument (C18Aq gold column 15.5 g, 0.1% TFA in MeCN:0.1% TFA in water gradient, collecting on 214 nM). Appropriate fractions were identified by HPLC-MS, combined and concentrated in vacuo to afford (2S)-2-Ethoxy-3-{4-[(2R)-2-hydroxy-2-(3-methoxyphenyl)ethoxy]phenyl}-N-methoxy-N-methylpropanamide (Compound No. 16) (0.042 g) as a pale yellow oil.

$^1$H NMR (300 MHz, CHLOROFORM-d) δ ppm 1.17 (t, J=6.98 Hz, 3 H), 2.96 (m, 2 H), 3.22 (s, 3 H), 3.34 (m, 1 H), 3.52 (m, 1 H), 3.60 (s, 3 H), 3.85 (s, 3 H), 4.01 (t, J=9.22 Hz, 1 H), 4.12 (m, 1 H), 4.40 (t, J=5.96 Hz, 1 H), 5.13 (dd, J=8.80, 3.03 Hz, 1 H), 6.80-6.93 (3 H), 7.03 (m, 2 H), 7.17 (d, J=8.66 Hz, 2 H), 7.31 (d, J=8.10 Hz, 1 H).

HPLC retention Time: 3.618 min
LCMS: 426.1 (M+Na)+; 404.0 (M+H)+

Example 28

(2S)-2-ethoxy-3-(4-{[4-(methylsulfonyl)benzyl]oxy}phenyl)propanoic acid

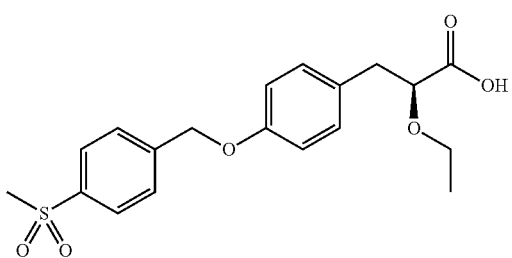 [SMILES: CCO[C@@H](Cc1ccc(OCc2ccc(S(C)(=O)=O)cc2)cc1)C(=O)O]

Ethyl (2S)-2-ethoxy-3-(4-hydroxyphenyl)propanoate (0.100 g, 0.420 mmol) was dissolved in tetrahydrofuran (3 mL) and [4-(methylsulfonyl)phenyl]methanol (109 mg, 0.585 mmol) was added. The reaction mixture was stirred at rt, then triphenylphosphine (165 mg, 0.630 mmol) is added followed by diisopropyl azodicarboxylate (130 uL, 0.66 mmol). After 4 hours the mixture was diluted with hexane (15 mL) to precipitate phenylphoshine oxide. The filtrate was diluted with EtOAc (20 mL), washed with 1N aq. HCl (25 mL), saturated aqueous sodium bicarbonate (25 mL), and brine (25 mL). The organic phase was dried over Na$_2$SO$_4$, filtered and concentrated in vacuo. The resulting crude product was purified by CombiFlash Rf (12 g Gold Silica gel column, acetone:hexane gradient, 220 nM collection). Appropriate fractions were identified by HPLC-MS, pooled, and concentrated in vacuo to give ethyl (2S)-2-ethoxy-3-(4-{[4-(methylsulfonyl)benzyl]oxy}phenyl)propanoate (0.170 g) which was taken forward without additional examination.

Ethyl (2S)-2-ethoxy-3-(4-{[4-(methylsulfonyl)benzyl]oxy}phenyl)propanoate (0.170 g, 0.418 mmol), prepared as described above, was dissolved in ethanol (2 mL) and sodium hydroxide in water (2 M, 1 mL, 2 mmol) was added and the reaction mixture was stirred at it and monitored by HPLC. When the reaction was interpreted to be complete (3 h) it was concentrated to provide a paste which was dissolved in water (20 mL). The aq. Phase was washed with EtOAc (2×20 mL), acidified to pH=1 with 1N aq. HCl and extracted with ether (2×25 mL). The combined ether extracts were dried over Na$_2$SO$_4$, filtered and concentrated in vacuo. The resulting crude oil was purified using CombiFlash Rf instrument (4 g Silica gel column, Acetone:hexane gradient, collecting at 225 nM). Appropriate fractions were identified by HPLC-MS, pooled, and concentrated in vacuo to give (2S)-2-ethoxy-3-(4-{[4-(methylsulfonyl)benzyl]oxy}phenyl)propanoic acid (0.021 g) as an ivory solid.

$^1$H NMR (400 MHz, CHLOROFORM-d) δ ppm 1.19 (t, J=7.0 Hz, 3 H), 2.97 (m, 1 H), 3.03-3.14 (4 H), 3.47 (m, 1 H), 3.62 (m, 1 H), 4.07 (dd, J=7.5, 4.4 Hz, 1 H), 5.15 (s, 2 H), 6.90 (d, J=8.5 Hz, 2 H), 7.19 (d, J=8.5 Hz, 2 H), 7.64 (d, J=8.3 Hz, 2 H), 7.97 (d, J=8.3 Hz, 2 H).

HPLC retention Time: 3.449 min
LCMS: 401.3 (M+Na)$^+$, 379.2 (M+H)$^+$, 377.2 (M−H)$^−$ Example 29

(2S)-2-ethoxy-N-methoxy-3-(4-{[4-(methylsulfonyl)benzyl]oxy}phenyl) propanamide (Compound No. 9)

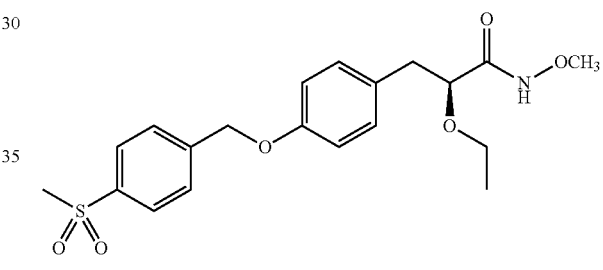

To a stirring solution of (2S)-2-ethoxy-3-(4-{[4-(methylsulfonyl)benzyl]oxy}phenyl)propanoic acid (80 mg, 0.2 mmol) in N,N-dimethylformamide (0.6 mL) was added N,N,N',N'-tetramethyl-O-(7-azabenzotriazol-1-yl)uronium hexafluorophosphate (100 mg, 0.264 mmol), N,N-diisopropylethylamine (0.110 mL, 0.634 mmol), and methoxyammonium chloride (22.3 mg, 0.264 mmol). The mixture was allowed to stir at RT overnight. The mixture was cast into water (15 mL), was extracted with EtOAc (2×15 mL) and the combined organic phases were dried (Na$_2$SO$_4$), filtered and concentrated in vacuo. The crude product was purified by chromatography on a reverse-phase combi-flash column eluting with 0-70% CH$_3$CN/water, collecting @ 214 nm. Appropriate fractions were identified by HPLC-MS, combined and concentrated in vacuo to afford (2S)-2-ethoxy-N-methoxy-3-(4-{[4-(methylsulfonyl)benzyl]oxy}phenyl) propanamide (Compound No. 9) (50 mg) as a clear, colorless oil.

$^1$H NMR (300 MHz, CHLOROFORM-d) δ ppm 1.16 (t, J=6.98 Hz, 3 H), 2.90 (m, 1 H), 3.01-3.19 (4 H), 3.33-3.59 (2 H), 3.67 (s, 3 H), 4.01 (dd, J=6.52, 3.91 Hz, 1 H), 5.15 (s, 2 H), 6.89 (d, J=8.57 Hz, 2 H), 7.18 (d, J=8.57 Hz, 2 H), 7.64 (d, J=8.29 Hz, 2 H), 7.97 (d, J=8.38 Hz, 2 H), 8.88 (br. s., 1 H).

Retention Time: 3.090 min
LCMS: 408.0 (M+H)+

Example 30

(2S)-2-ethoxy-N-methoxy-3-(4-{2-[4-(methylsulfonyl)phenyl]ethoxy}phenyl) propanamide (Compound No. 10)

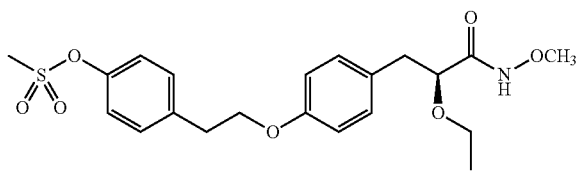 [SMILES: CCO[C@@H](Cc1ccc(OCCc2ccc(OS(C)(=O)=O)cc2)cc1)C(=O)NOC]

To a stirring solution of tesaglitazar (Aurora Building blocks, A08.473.376) (200 mg, 0.5 mmol) in N,N-dimethylformamide (2 mL) was added N,N,N',N'-tetramethyl-O-(7-azabenzotriazol-1-yl)uronium hexafluorophosphate (242 mg, 0.637 mmol), N,N-diisopropylethylamine (0.266 mL, 1.53 mmol) and methoxyammonium chloride (53.8 mg, 0.637 mmol). The mixture was allowed to stir at re overnight. The reaction mixture was cast into water (25 mL), was extracted with EtOAc (2×50 mL), and the combined organic phases were dried ($Na_2SO_4$), filtered and concentrated in vacuo. The crude product was purified by chromatography on a reverse-phase combi-flash column eluting with 0-70% $CH_3CN$/water, collecting @ 214 nm. Appropriate fractions were identified by HPLC-MS, pooled, and partitioned between saturated $NaHCO_3$ (150 mL) and EtOAc (2×100 mL). The combined organic phases were dried ($Na_2SO_4$), filtered and concentrated in vacuo to give (2S)-2-ethoxy-N-methoxy-3-(4-{2-[4-(methylsulfonyl)phenyl]ethoxy}phenyl) propanamide (Compound No. 10) (54 mg) as a pale yellow oil.

$^1$H NMR (300 MHz, CHLOROFORM-d) δ ppm 1.16 (t, J=6.98 Hz, 3 H), 2.92 (m, 1 H), 3.05-3.13 (3 H), 3.15 (s, 3 H), 3.50 (q, J=7.05 Hz, 2 H), 3.66 (s, 3 H), 4.05 (dd, J=6.43, 3.91 Hz, 1 H), 4.15 (t, J=6.75 Hz, 2 H), 6.82 (m, 2 H), 7.14 (d, J=8.57 Hz, 2 H), 7.20-7.27 (m, 2 H), 7.30-7.39 (m, 2 H), 8.91 (br. s., 1 H).

HPLC retention Time: 3.559 min
LCMS: 438.0 (M+H)+

Example 31

Assays

Assays useful for evaluating the biological properties of compounds of Formula I may be assayed using the following assay methods.

Assays for Measuring Reduced PPARγ Receptor Activation.

Whereas activation of the PPARγ receptor is generally believed to be a selection criteria to select for molecules that may have anti-diabetic and insulin sensitizing pharmacology, this invention finds that activation of this receptor should be a negative selection criterion. Molecules will be chosen from this chemical space because they have reduced, not just selective, activation of PPARγ. The optimal compounds have at least a 10-fold reduced potency as compared to pioglitazone and less than 50% of the full activation produced by rosiglitazone in assays conducted in vitro for transactivation of the PPARγ receptor. The assays are conducted by first evaluation of the direct interactions of the molecules with the ligand binding domain of PPARγ. This can be performed with a commercial interaction kit that measures the direct interaction by florescence using rosiglitazone as a positive control.

PPARγ binding is measured by a TR-FRET competitive binding assay using Invitrogen LanthaScreen™ TR-FRET PPARγ Competitive Binding Assay (Invitrogen #4894). This assay uses a terbium-labeled anti-GST antibody to label the GST tagged human PPARγ ligand binding domain (LBD). A fluorescent small molecule pan-PPAR ligand tracer binds to the LBD causing energy transfer from the antibody to the ligand resulting in a high TR-FRET ratio. Competition binding by PPARγ ligands displace the tracer from the LBD causing a lower FRET signal between the antibody and tracer. The TR-FRET ratio is determined by reading the fluorescence emission at 490 and 520 nm using a Synergy2 plate reader (BioTek).

The ability of compounds of the present invention to bind to PPARγ may also be measured using a commercial binding assay (Invitrogen Corporation, Carlsbad, Calif.) that measures the test compounds ability to bind with PPAR-LBD/Fluormone PPAR Green complex. These assays are performed on three occasions with each assay using duplicate wells at each concentration of tested compound. The data are mean and SEM of the values obtained from the three experiments. Rosiglitazone or pioglitazone may be used as the positive control in each experiment. Compounds were added at the concentrations shown, which ranged from 0.1-100 micromolar.

PPARγ activation in intact cells may be measured by a cell reporter assay using Invitrogen GeneBLAzer PPARγ Assay (Invitrogen #1419). This reporter assay uses the human PPARγ ligand binding domain (LBD) fused to the GAL4 DNA binding domain (DBD) stably transfected into HEK 293H cells containing a stably expressed beta-lactamase reporter gene under the control of an upstream activator sequence. When a PPARγ agonist binds to the LBD of the GAL4/PPAR fusion protein, the protein binds to the upstream activator sequence activating the expression of beta-lactamase. Following a 16 hour incubation with the agonists the cells are loaded with a FRET substrate for 2 hours and fluorescence emission FRET ratios are obtained at 460 and 530 nm in a Synergy2 plate reader (BioTek).

In addition to showing the reduced activation of the PPARγ receptor in vitro, the compounds will not produce significant activation of the receptor in animals. Compounds dosed to full effect for insulin sensitizing actions in vivo (see below) will be not increase activation of PPARγ in the liver as measured by the expression of a P2, a biomarker for ectopic adipogenesis in the liver [Matsusue K, Haluzik M, LambertG, Yim S-H, Oksana Gavrilova O, Ward J M, Brewer B, Reitman M L, Gonzalez F J. (2003) Liver-specific disruption of PPAR in leptin-deficient mice improves fatty liver but aggravates diabetic phenotypes. J. Clin. Invest.; 111: 737] in contrast to pioglitazone and rosiglitazone, which do increase a P2 expression under these conditions.

Glucose, Insulin, and Triglyceride in Diabetic KKAy Mice Treated with Exemplary Compounds of the Present Invention.

The insulin sensitizing and antidiabetic pharmacology are measured in the $KKA^Y$ mice as previously reported [Hofmann, C., Lomez, K., and Colca, J. R. (1991). Glucose transport deficiency corrected by treatment with the oral anti-hyperglycemic agent Pioglitazone. Endocrinology, 129: 1915-1925.]. Compounds are formulated in 1% sodium carboxy methylcellulose, and 0.01% tween 20 and dosed daily by oral gavage. After 4 days of once daily treatment, blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Compounds were formulated by suspension and orally dosed to KKA$^Y$ mice at 93 mg/kg for 4 days. The compounds were first dissolved in DMSO and then placed into aqueous suspension containing 7-10% DMSO, 1% sodium methylcarboxycellulose, and 0.01% Tween 20. On the fifth day, the mice were fasted and blood samples were obtained approximately 18 hours after the last dose. The parameters were measured by standard assay methods. Data are mean and SEM N=6-12 mice.

BAT Differentiation.

Precursors of BAT are isolated from the interscapular adipose pad of either normal or diabetic mice and cultured in vitro as described below based on the modifications recited in Petrovic N, Shabalina I G, Timmons J A, Cannon B, Nedergaard J. Am. J. Physiol. Endocrinol. Metab. 295: E287-E296, 2008, hereby incorporated by reference.

The brown fat pads are pooled and minced, digested for 45 minutes in isolation buffer containing 0.15% (wt/vol) collagenase. The cell suspension is filtered through a 100 μm nylon filter and centrifuged at 200×g for 5 minutes. The pellet containing the preadipocytes is resuspended in 1.2 ml/animal of DMEM containing 10% FBS, 10 mM HEPES, 25 μg/ml sodium ascorbate, 100 U/ml penicillin, and 100 μg/ml streptomycin. The resuspended preadipocytes are distributed into 6 well plates and grown at 37° C. in an atmosphere of 10% $CO_2$ in air with 80% humidity. The medium is changed on the first day and then every second day until confluent.

Cells are then treated with the compounds or compound salts being assayed for BAT differentiation. This treatment can occur simultaneously with, after, or before strategies to increase intracellular cyclic nucleotides. The development of the BAT phenotype is assessed by direct measure of the uncoupling protein 1 (UCP1), which is emblematic of brown adipose cells.

Following treatment of the cells, the growth medium is aspirated, rinsed with PBS, and lysed with KHM buffer containing 1% Igepal CA-630, and a protease inhibitor cocktail. The lysate is centrifuged at 8,000×g for 5 minutes (4° C.), the supernatant containing the cell lysate is collected and total protein analyzed using the BCA method. 20 μg/lane of cell lysate is run on 10-20% Tris glycine gels under reducing conditions and the proteins transferred to PVDF membranes. Western blotting is conducted using UCP1 polyclonal 1° antibody, an HRP conjugated 2° antibody, and imaged using enhanced chemiluminescence reagents and imaging film. Densitometry is conducted on the scanned films using ImageJ software and analyzed using GraphPad Prism software.

Mitochondrial Membrane Competitive Binding Crosslinking Assay

A photoaffinity crosslinker was synthesized by coupling a carboxylic acid analog of pioglitazone to a p-azido-benzyl group containing ethylamine as in Amer. J. Physiol 256: E252-E260. The crosslinker was iodinated carrier free using a modification of the Iodogen (Pierce) procedure and purified using open column chromatography (PerkinElmer). Specific crosslinking is defined as labeling that is prevented by the presence of competing drug. Competitive binding assays are conducted in 50 mM Tris, pH 8.0. All crosslinking reactions are conducted in triplicate using 8 concentrations of competitor ranging from 0-25 uM. Each crosslinking reaction tube contains 20 ug of crude mitochondrial enriched rat liver membranes, 0.1 uCi of 125I-MSDC-1101, and ± competitor drug with a final concentration of 1% DMSO. The binding assay reaction is nutated at room temperature in the dark for 20 minutes and stopped by exposure to 180,000 μJoules. Following crosslinking, the membranes are pelleted at 20,000×g for 5 minutes, the pellet is resuspended in Laemmli sample buffer containing 1% BME and run on 10-20% Tricine gels. Following electrophoresis the gels are dried under vacuum and exposed to Kodak BioMax MS film at −80° C. The density of the resulting specifically labeled autoradiography bands are quantitated using ImageJ software (NIH) and $IC_{50}$ values determined by non-linear analysis using GraphPad Prism™.

Data for each of the assays performed on compound of Formula I is provided below in Table 2:

TABLE 2

Assay Data for compounds of Formula I.

| Compound | PPARγ $IC_{50}$ (μM) | BAT[1] (3 mM) | BAT[1] (10 mM) | Glucose[2] (mean T/C) | Triglycerides[2] (mean T/C) | Insulin[2] (T/C) |
|---|---|---|---|---|---|---|
| Mitoglitazone | 26.6 | — | — | — | — | — |
| Rosiglitazone | 0.125 | — | — | — | — | — |
| 1 | 58.9 | 1.06 | 1.18 | — | — | — |
| 2 | >100 | 0.91 | 1.01 | — | — | — |
| 3 | >250 | 0.85 | 0.95 | — | — | — |
| 4 | 27.7 | 0.92 | 1.0 | — | — | — |
| 5 | >250 | 0.94 | 1.0 | 0.97 | — | — |
| 6 | >195 | 0.2 | 0.83 | 0.55 | — | — |
| 7 | 11.8 | 0.87 | 0.94 | — | — | — |
| 8 | 98.5 | 0.7 | 1.0 | — | — | — |
| 9 | >250 | 0.4 | 0.63 | — | — | — |
| 10 | 7.9 | 1.12 | 1.19 | — | — | — |
| 11 | 30.5 | 0.83 | 0.9 | — | — | — |
| 12 | 164.3 | 1.11 | 1.16 | 0.49 | — | — |
| 13 | 61.4 | 1.16 | 1.0 | 0.59 | — | — |
| 14 | >250 | 0.99 | 1.04 | 0.76 | — | — |
| 15 | >200 | 0.73 | 0.98 | — | — | — |
| 16 | 190.8 | 0.73 | 0.92 | — | — | — |
| 17 | 27.7 | 0.56 | 0.53 | — | — | — |
| 18 | >250 | 0.71 | 0.76 | — | — | — |
| 19 | >250 | 0.35 | 0.69 | — | — | — |
| 20 | 10.9 | 0.82 | 0.84 | — | — | — |
| 21 | 3.7 | 0.8 | 0.87 | — | — | — |

[1]This data is provided as T/C wherein the control compound is 5-(4-(2-(5-ethylpyridin-2-yl)-2-oxoethoxy)benzyl)thiazolidine-2,4-dione for each of the concentrations tested.
[2]T/C data is test compound activity that is normalized with respect to the vehicle activity.

It is noted that "-", in Table 2, indicates that no data is available.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula II:

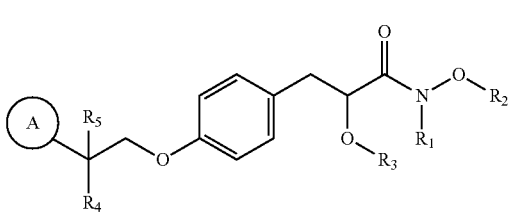

or a pharmaceutically acceptable salt thereof, wherein:
Each of $R_1$ and $R_2$ is independently selected from —H, —$C_{1-6}$alkyl, aryl, 5-10 membered heteroaryl, —$C_{3-6}$cycloaliphatic, 3-8 membered heterocycloaliphatic, —$CH_2$-aryl, —$CH_2$-5-10membered heteroaryl, —$CH_2$—$C_{3-6}$cycloaliphatic, —$CH_2$-3-8 membered heterocycloaliphatic, each of which is optionally substituted with 1-3 groups selected from halo, —OH, or phenyl,
or $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S;
$R_3$ is —$C_{1-6}$alkyl optionally substituted with 1-3 groups selected from halo, —OH, or phenyl;
each of $R_4$ and $R_5$ is independently selected from —H, —OH, —$NH_2$, —$NHC(O)R_7$, —$NHC(O)OR_7$, —$NHS(O)_2R_7$, —$C(O)R_7$, —$C(O)OR_7$, —$CH_2OR_7$, —$CH_2N(R_7)_2$, —$C_{1-6}$alkyl, each of which is optionally substituted with 1-3 groups selected from halo or —OH,
or $R_4$ and $R_5$ together form oxo or =N—O—$R_7$;
Ring A is a 5-8 membered saturated, partially unsaturated, or fully unsaturated ring having 0-3 heteroatoms independently selected from N, O, or S, wherein ring A is optionally substituted with 1-3 of $R_6$;
each $R_6$ is independently halo, —H, —CN, —$OR_7$, —$NO_2$, —$C_{1-6}$ alkyl, aryl, 5-10 membered heteroaryl, —$S(O)_2R_7$, or —$C(O)R_7$, each of which is optionally substituted with 1-3 groups selected from halo or —OH; and
each $R_7$ is independently —H, —$C_{1-6}$alkyl, —$C_{3-8}$ cycloalkyl, or phenyl.

2. The compound of claim 1, wherein $R_1$ is —H or —$C_{1-6}$alkyl.

3. The compound of claim 1, wherein $R_2$ is —H, —$C_{1-6}$ alkyl, aryl, 5-10membered heteroaryl, —$C_{3-6}$cycloaliphatic, or 3-8 membered heterocycloaliphatic, each of which is optionally substituted with 1-3 groups selected from halo, —OH, or phenyl.

4. The compound of claim 3, wherein $R_2$ is —H or —$C_{1-6}$alkyl.

5. The compound of claim 1, wherein $R_1$ and $R_2$ together with the atoms to which they are attached form an optionally substituted 5-8 membered saturated or partially unsaturated heterocyclic ring that includes an N atom, an O atom, and up to 1 additional heteroatom selected from N, O, or S.

6. The compound of claim 1, wherein $R_3$ is —$C_{1-3}$ alkyl optionally substituted with 1-3 groups selected from halo, —OH, or phenyl.

7. The compound of claim 1, wherein one of $R_4$ and $R_5$ is H and the other is independently selected from —H or —OH, or $R_4$ and $R_5$ together form oxo.

8. The compound of claim 1, wherein ring A is a 6-membered, saturated, partially unsaturated, or fully unsaturated ring having 0-3 heteroatoms independently selected from N, O, and S, optionally substituted with 1-3 of $R_6$.

9. The compound of claim 1, wherein the compound of Formula II is a compound of Formula IIa:

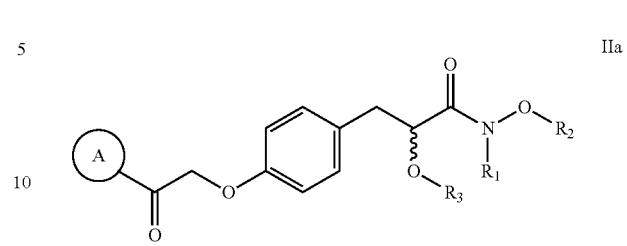

or a pharmaceutically acceptable salt thereof.

10. The compound of claim 1, wherein the compound of Formula II is a compound of Formula IIa-1:

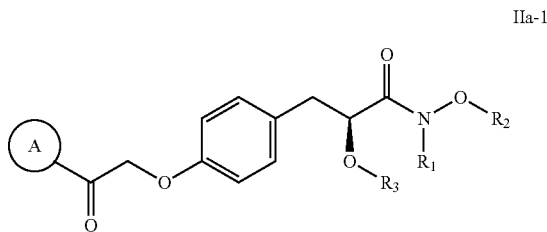

or a pharmaceutically acceptable salt thereof.

11. The compound of claim 1, wherein the compound of Formula II is a compound of Formula IIb:

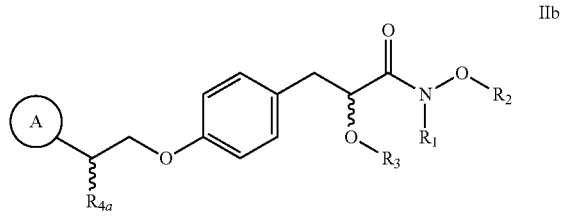

or a pharmaceutically acceptable salt thereof, wherein
$R_{4a}$ is independently selected from —OH, —$NH_2$, —$NHC(O)R_7$, —$NHC(O)OR_7$, —$NHS(O)_2R_7$, —$C(O)R_7$, —$C(O)OR_7$, —$CH_2OR_7$, —$CH_2N(R_7)_2$, —$C_{1-6}$ alkyl, each of which is optionally substituted with 1-3 groups selected from halo or —OH.

12. The compound of claim 11, wherein $R_{4a}$ is —OH.

13. The compound of claim 1, wherein the compound of Formula H is a compound of Formula IIb-1:

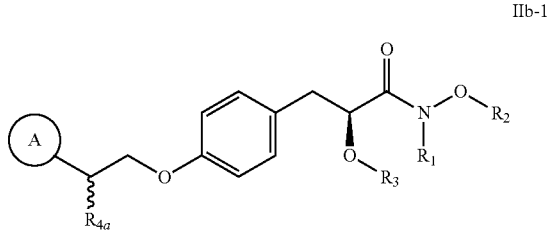

or a pharmaceutically acceptable salt thereof, wherein
$R_{4a}$ is independently selected from —OH, —$NH_2$, —$NHC(O)R_7$, —$NHC(O)OR_7$, —$NHS(O)_2R_7$, —$C(O)R_7$, —$C(O)OR_7$, —$CH_2OR_7$, —$CH_2N(R_7)_2$, —$C_{1-6}$alkyl, each of which is optionally substituted with 1-3 groups selected from halo or —OH.

14. The compound of claim 13, wherein $R_{4a}$ is —OH.

15. The compound of claim 13, wherein the compound of Formula IIb-1 is a compound of Formula IIb-1a, IIb-1b, IIb-1c, or IIb-1d:

IIb-1a
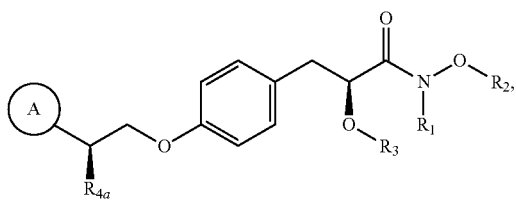

IIb-1b
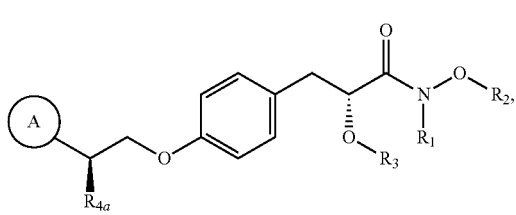

IIb-1c
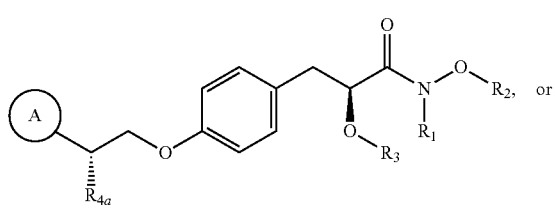

IIb-1d
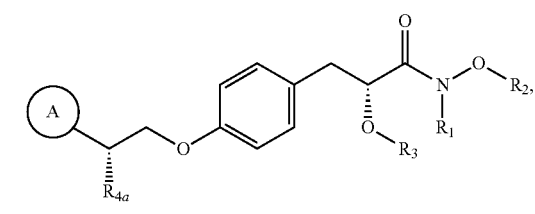

or a pharmaceutically acceptable salt thereof.

16. The compound of claim 1, wherein the compound of Formula II is a compound of Formula IIb-2:

IIb-2
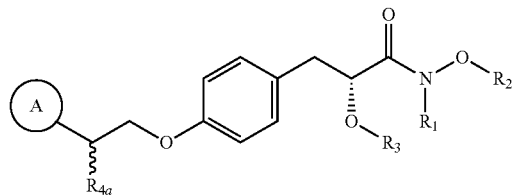

or a pharmaceutically acceptable salt thereof, wherein $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

17. The compound of claim 16, wherein $R_{4a}$ is —OH.

18. The compound of claim 1, wherein the compound of Formula II is a compound of Formula IIb-3:

IIb-3
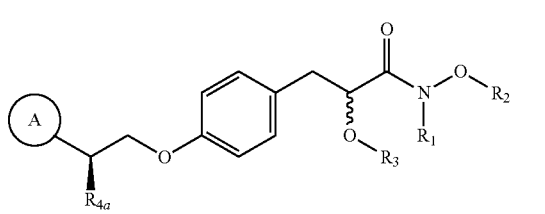

or a pharmaceutically acceptable salt thereof, wherein $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$alkyl, each of which is optionally substituted with 1-3 groups selected from halo or —OH.

19. The compound of claim 18, wherein $R_{4a}$ is —OH.

20. The compound of claim 1, wherein the compound of Formula II is a compound of Formula IIb-4:

IIb-4
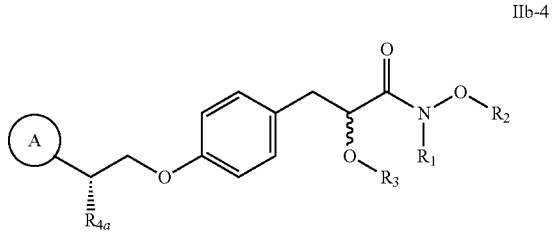

or a pharmaceutically acceptable salt thereof, wherein $R_{4a}$ is independently selected from —OH, —NH$_2$, —NHC(O)R$_7$, —NHC(O)OR$_7$, —NHS(O)$_2$R$_7$, —C(O)R$_7$, —C(O)OR$_7$, —CH$_2$OR$_7$, —CH$_2$N(R$_7$)$_2$, —C$_{1-6}$ alkyl, each of which is optionally substituted with 1-3 groups selected from halo or —OH.

21. The compound of claim 20, wherein $R_{4a}$ is —OH.

22. A compound selected from

| Compound | Structure |
|---|---|
| 2 | 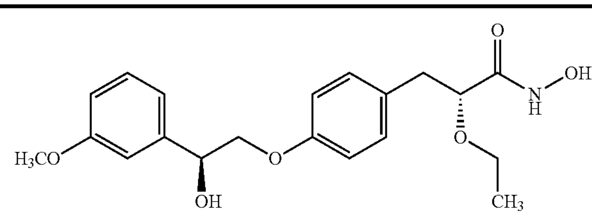 |

-continued

| Compound | Structure |
|---|---|
| 8 | 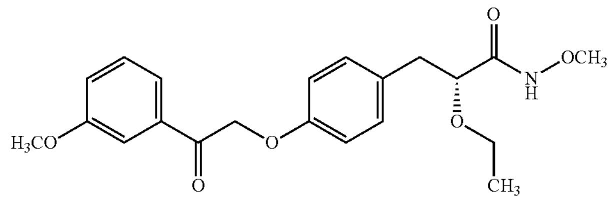 [SMILES: CCO[C@H](Cc1ccc(OCC(=O)c2cccc(OC)c2)cc1)C(=O)NOC] |
| 10 | 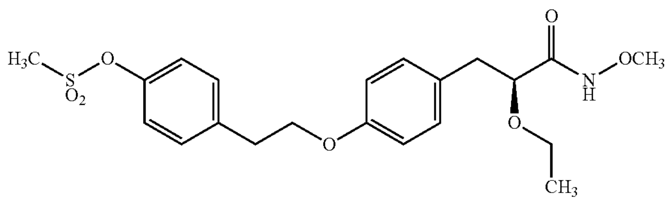 [SMILES: CCO[C@@H](Cc1ccc(OCCc2ccc(OS(C)(=O)=O)cc2)cc1)C(=O)NOC] |
| 11 | 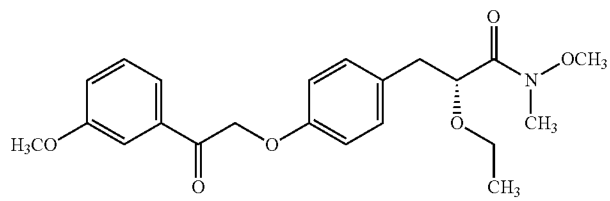 [SMILES: CCO[C@H](Cc1ccc(OCC(=O)c2cccc(OC)c2)cc1)C(=O)N(C)OC] |
| 12 | 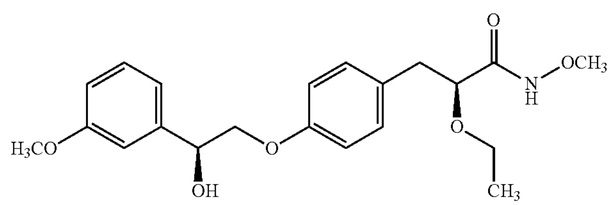 [SMILES: CCO[C@@H](Cc1ccc(OC[C@@H](O)c2cccc(OC)c2)cc1)C(=O)NOC] |
| 13 | 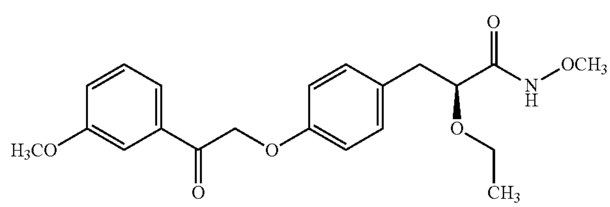 [SMILES: CCO[C@@H](Cc1ccc(OCC(=O)c2cccc(OC)c2)cc1)C(=O)NOC] |
| 14 | 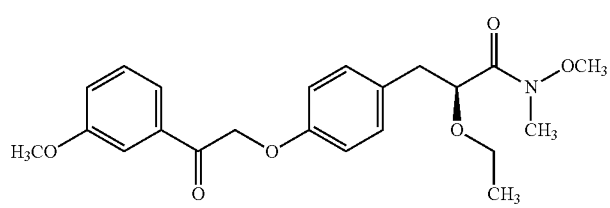 [SMILES: CCO[C@@H](Cc1ccc(OCC(=O)c2cccc(OC)c2)cc1)C(=O)N(C)OC] |
| 15 | 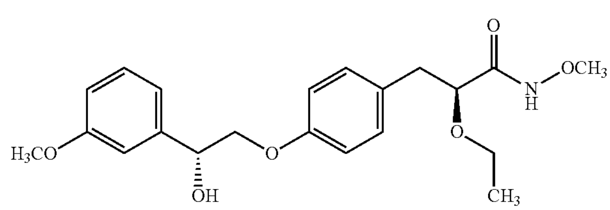 [SMILES: CCO[C@@H](Cc1ccc(OC[C@H](O)c2cccc(OC)c2)cc1)C(=O)NOC] |

| Compound | Structure |
|---|---|
| 16 | 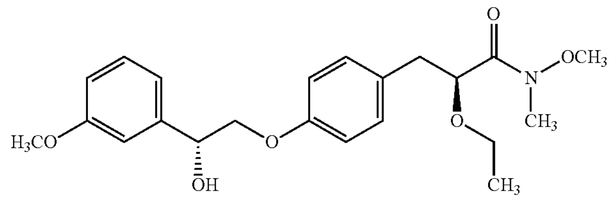 [SMILES: CCO[C@@H](Cc1ccc(OC[C@H](O)c2cccc(OC)c2)cc1)C(=O)N(C)OC] |
| 17 | 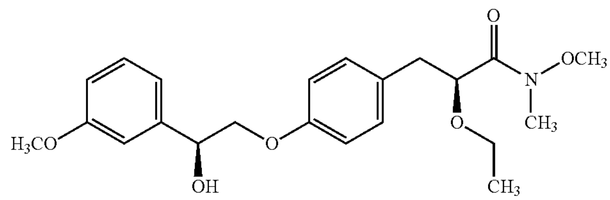 |
| 18 | 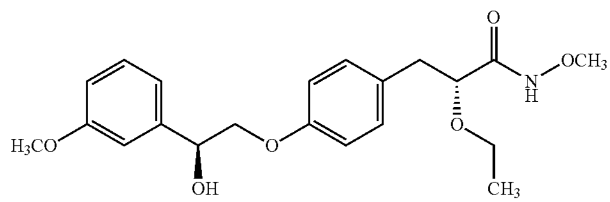 |
| 19 | 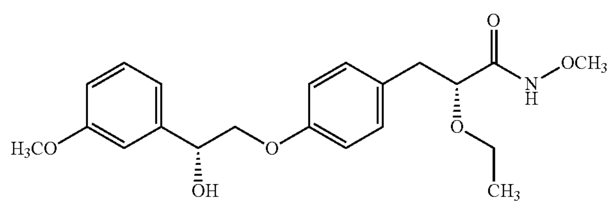 [SMILES: CCO[C@H](Cc1ccc(OC[C@H](O)c2cccc(OC)c2)cc1)C(=O)NOC] |
| 20 | 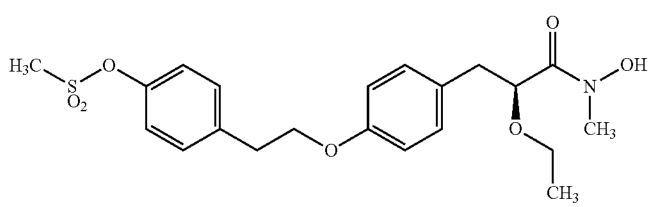 [SMILES: CCO[C@@H](Cc1ccc(OCCc2ccc(OS(C)(=O)=O)cc2)cc1)C(=O)N(C)O] |
| 21 | 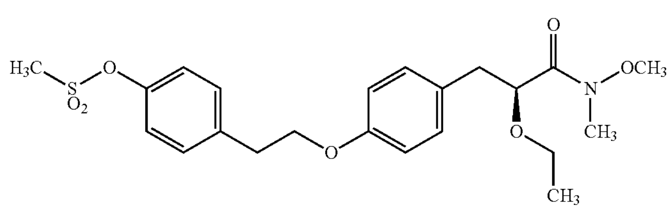 [SMILES: CCO[C@@H](Cc1ccc(OCCc2ccc(OS(C)(=O)=O)cc2)cc1)C(=O)N(C)OC] |

23. A pharmaceutical composition comprising a compound of claim 1 or a pharmaceutically acceptable salt thereof.

* * * * *